US008685664B2

(12) United States Patent
Demuth et al.

(10) Patent No.: US 8,685,664 B2
(45) Date of Patent: Apr. 1, 2014

(54) USE OF INHIBTORS OF GLUTAMINYL CYCLASES FOR TREATMENT AND PREVENTION OF DISEASE

(75) Inventors: Hans-Ulrich Demuth, Halle/Saale (DE); Torsten Hoffmann, Halle/Saale (DE); Andre Johannes Niestroj, Sennewitz (DE); Stephan Schilling, Halle/Saale (DE); Ulrich Heiser, Halle/Saale (DE)

(73) Assignee: Probiodrug AG, Halle/Saale (DE)

( * ) Notice: Subject to any disclaimer, the term of this patent is extended or adjusted under 35 U.S.C. 154(b) by 677 days.

(21) Appl. No.: 12/101,497

(22) Filed: Apr. 11, 2008

(65) Prior Publication Data

US 2008/0286810 A1 Nov. 20, 2008

Related U.S. Application Data

(62) Division of application No. 10/839,017, filed on May 5, 2004, now Pat. No. 7,381,537.

(60) Provisional application No. 60/468,014, filed on May 5, 2003, provisional application No. 60/468,043, filed on May 5, 2003, provisional application No. 60/512,038, filed on Oct. 15, 2003.

(51) Int. Cl.
| | | |
|---|---|---|
| C12Q 1/48 | (2006.01) | |
| C12Q 1/00 | (2006.01) | |
| C12N 9/10 | (2006.01) | |
| C07H 21/04 | (2006.01) | |
| A61K 38/00 | (2006.01) | |

(52) U.S. Cl.
USPC ............... 435/15; 435/193; 435/4; 536/23.2; 530/324

(58) Field of Classification Search
None
See application file for complete search history.

(56) References Cited

U.S. PATENT DOCUMENTS

| | | | |
|---|---|---|---|
| 5,552,426 A | 9/1996 | Lunn et al. | |
| 7,381,537 B2 | 6/2008 | Demuth et al. | |
| 8,129,160 B2 * | 3/2012 | Schilling et al. | 435/183 |

FOREIGN PATENT DOCUMENTS

| | | |
|---|---|---|
| EP | 1262552 A1 | 12/2002 |
| WO | 9320061 | 10/1993 |
| WO | 9941224 | 8/1999 |
| WO | 0134594 | 5/2001 |
| WO | 0213821 | 2/2002 |
| WO | 02092103 | 11/2002 |
| WO | 03040174 | 5/2003 |
| WO | 2004089366 | 10/2004 |
| WO | 2004098625 | 11/2004 |

OTHER PUBLICATIONS

Yu et al. Substrate and Inhibitor Specificity of Glutamine Cyclotransferase (QC). Biol. Chem. Hoppe-Seyler, vol. 377, pp. 395-398, Jun. 1996.*
Misquitta et al. Characterization of the inhibition of glutaminyl cyclase by imidazole derivatives. FASEB Journal, (Mar. 20, 2002) vol. 16, No. 4, pp. A157. print. Meeting Info.: Annual Meeting of the Professio.: Annual Meeting of the Professional Research Scientists on Experimental Biology. New Orleans, Louisiana, USA. Apr. 20-24, 2002.*
Schilling et al. Identification of human glutaminyl cyclase as a metal-loenzyme. Potent inhibition by imidazole derivatives and heterocyclic chelators. J. Biol. Chem.2003, 278, 49773-49779.*
Misquitta et al. Inhibition studies of glutaminyl cyclase. FASEB Journal, (Mar. 8, 2001-) vol. 15, No. 5, pp. A1159.*
Bateman et al., Evidence for histidines in human pituitary glutaminyl cyclase, Biochemistry, 2001, 40:11246-11250.
Boeckers et al., Glutaminyl-cyclase expression in the bovine/porcine hypothalamus and pituitary, J Neurondocrinol, 1995, 7:445-453.
Booth et al., Human glutaminyl cyclase and bacterial zinc aminopeptidase share a common fold and active site, BMC Biology, 2004, 2:2.
Borchelt et al., Familial Alzheimer's disease-linked presenilin 1 variants elevate A(beta)1-42/1-40 ration in vitro and in vivo, Neuron, 1996, 17:1005-1013.
Busby et al., An enzyme(s) that converts glutaminyl-peptides into pyroglutamyl-peptides, J Biol Chem, 1987, 262:8532-8536.
Citron et al., Mutant presenilins of Alzheimer's disease increase production of 42-residue amyloid (beta)-protein in both transfected cells and transgenic mice, Nat Med, 1997, 3:67-72.
Consalvo et al., A rapid fluorometric assay for N-terminal glutaminyl cyclase activity using high-performance liquid chromatography, Anal Biochem, 1988, 175:131-138.
Dahl et al., Carica papaya glutamine cyclotransferase belongs to a novel plant enzyme subfamily: cloning and characterization of the recombinant enzyme, Protein Expr Purif, 2000, 20:27-36.
El Moussaoui et al., Revisiting the enzymes stored in the laticifers of Carica papaya in the context of their possible participation in the plant defence mechanism, Cell Mol Life Sci, 2001,58:556-570.
Fischer and Spiess, Identification of a mammalian glutaminyl cyclase converting glutaminyl into pyroglutaminyl peptides, PNAS, 1987, 84:3628-3632.
Funato et al., 1998, Quantitation of amyloid (beta)-protein (A(beta)) in the cortex during aging and in Alzheimer's disease, Am J Pathol, 1987, 152:983-992.
Garden et al., 1999, Formation of N-pyroglutamyl peptides from N-glu and N-gln precursors in Aplysia neurons, J Neurochem 72:676-681.
Geddes et al., N-terminus truncated (beta)-amyloid peptides and C-terminus truncated secreted forms of amyloid precursor protein: distinct roles in the pathogenesis of Alzheimer's disease, Neurobiol Aging, 1999, 20:75-79.

(Continued)

*Primary Examiner* — Yong Pak
(74) *Attorney, Agent, or Firm* — Dentons US LLP

(57) ABSTRACT

Novel physiological substrates of mammalian glutaminyl cyclase (QC, EC 2.3.2.5), new effectors of QC, methods for screening for such effectors, and the use of such effectors and pharmaceutical compositions comprising such effectors for the treatment of conditions that can be treated by modulation of QC-activity. Preferred compositions additionally comprise inhibitors of DP IV or DP IV-like enzymes for the treatment or alleviation of conditions that can be treated by modulation of QC- and DP IV-activity.

16 Claims, 23 Drawing Sheets

(56) References Cited

OTHER PUBLICATIONS

Glenner et al., Alzheimer's disease: initial report of the purification and characterization of a novel cerebrovascular amyloid protein, Biochem Biophys Res Comm, 1984,120:885-890.
Gololobov et al., 1996, Substrate and inhibitor specificity of glutamine cyclotransferase (QC), Biol Chem, 377:395-398.
Haass and Selkoe, Cellular processing of (beta)-amyloid precursor protein and the genesis of amyloid (beta)-peptide, Cell, 1993, 75:1039-1042.
Harigaya et al, Amyloid (beta)-protein starting pyroglutamate at position 3 is a major component of the amyloid deposits in the Alzheimer's brain, BBRC, 2000, 276:422-427.
He et al., The A(beta) 3-pyroglutamyl and 11-pyroglutamyl peptides found in senile plaque have greater (beta)-sheet forming and aggregation propensities in vitro than full-length A(beta), Biochemistry, 1999, 38:10871-10877.
Hosoda et al.,Quantification of modified amyloid (beta) peptides in Alzheimer disease and Down Syndrome brains, J Neuropathol Exp Neurol, 1998, 57:1089-1095.
Itagaki et al., Relationship of microglia and astroctyes to amyloid deposits of Alzheimer disease, J Neuroimmunol, 1989, 24:173-182.
Iwatsubo et al., Full-length amyloid-(beta)(1-42(43)) and amino-terminally modified and truncated amyloid-(beta)42(43) deposit in diffuse plaques, Am J Pathol 1996, 149:1823-1830.
Kang et al., The precursor of Alzheimer's disease amyloid A4 protein resembles a cell-surface receptor, Nature, 1987, 325:733-736.
Kurbacher et al., Chemoprotection in anticancer therapy: the emerging role of amifostine (WR-2721), Anticancer Res, 1998, 18:2203-2210.
Lalowski et al., The "nonamyloidogenic" p3 fragment (Amyloid (beta)17-42) is a major constituent of Down's Syndrome cerebellar preamyloid, J Biol Chem, 1996, 27:33623-33631.
Lemere et al., The E280A presenilin 1 Alzheimer mutation produces increased A(beta)42 deposition and severe cerebellar pathology, Nat Med, 1996, 2:1146-1150.
Mann and Iwatsubo, Diffuse plaques in the cerebellum and corpus striatum in Down's syndrome contain amyloid (beta) protein (A(beta)) only in the form of A(beta)42(43), Neurodegen, 1996, 5:115-120.
Messer, Enzymatic cyclization of L-glutamine and L-glutaminyl peptides, Nature, 1963, 197:1299.
Misquitta et al., Characterization of the inhibition of glutaminyl cyclase by imidazole derivatives and phenanthrolines, FASEB Annual Meet, 2002.
Misquitta et al., Inhibition studies of glutaminyl cyclase, FASEB Journal, 2001.
Mori et al., Mass spectrometry of purified amyloid (beta) protein in Alzheimer's disease, J Biol Chem, 1992, 267:17082-17086.
Muggia et al., Phase I study of amifostine (A) as a cytoprotector of the gemcitabine/cisplatin (GP) combination, Eur J Cancer, 2001, 37:S71.
Pike et al., Amino-terminal deletions enhance aggregation of (beta)-amyloid peptides in vitro, Neurobiol Dis, 2001, 8:173-180.
Pohl et al., Primary structure and functional expression of a glutaminyl cyclase, PNAS, 1991, 88:10059-10063.
Poplin et al., Randomized clinical trial of mitomycin-C with or without pretreatment with WR-2721 in patients with advanced colorectal cancer Cancer Chemother Pharmacol, 1994, 33:415-419.
Russo et al., Heterogeneity of water-soluble amyloid (beta)-peptide in Alzheimer's disease and Down's syndrome brains, FEBS Let, 1997, 409:411-416.
Russo et al., Presenilin-1 mutations in Alzheimer's disease, Nature, 2000, 405:531-532.
Russo et al., Identification of amino-terminally and phosphotyrosine-modified carboxy-terminal fragments of the amyloid precursor protein in Alzheimer's disease and Down's Syndrome brain, Neurobiol Dis, 2001, 8:173-180.
Russo et al., Pyroglutamate-modified amyloid (beta)-peptides—A(beta)N3(pE)—strongly affect cultured neuron and astrocyte survival, J Neuro, 2002, Chem, 82:1480-1489.
Saido et al., Dominant and differential deposition of distinct (beta)-amyloid peptide species, A(beta)N3(pE), in senile plaques, Neuron, 1995, 14:457-466.
Saido, Involvement of polyglutamine endolysis followed by pyroglutamate formation in the pathogenesis of triplet repeat/polyglutamine-expansion diseases, Med Hypotheses, 2000, 54:427-429.
Schilling et al, Identification of human glutaminyl cyclase as a metalloenzyme, J Biol Chem, 2003, 278:49773-49779.
Schilling et al., Glutaminyl cyclases unfold glutamyl cyclase activity under mild acid conditions, FEBS Letters, 2004, 563:191-196.
Selkoe, Alzheimer's disease: genes, proteins and therapy, Neuroimmunol, 2001, 24:173-182.
Shirotani et al., Generation of amyloid (beta) peptide with pyroglutamate at position 3 in primary cortical neurons, Neurosci Lett, 2002, 327:25-28.
Simons et al., Amyloidogenic processing of the human amyloid precursor protein in primary cultures of rat hippocampal neurons, J Neurosci, 1996, 16:899-908.
Tekirian et al., N-terminal heterogeneity of parenchymal and cerebrovascular A(beta) deposits, J Neuropathol Exp Neurol, 1998, 57:76-94.
Tekirian et al., Toxicity of pyroglutaminated amyloid (beta)-peptides 3(pE)-40 and -42 is similar to that of A(beta)1-40 and -42, J Neurochem, 1999, 73:1584-1589.
Terry and Katzmann, Senile dementia of the Alzheimer type, Ann Neurol, 1983, 14:497-506.
Tsavaris et al., Amifostine, in a reduced dose, protects against severe diarrhea associated with weekly fluorouracil and folinic acid chemotherapy in advanced colorectal cancer: a pilot study, J Pain Sympt Managm, 2003, 26:849-854.

* cited by examiner

FIGURE 21

```
hQC     MAGGRHRRVVGTLHLLLVAALPWASRGVSPSASAWPEEKNYHQPAILNSSALRQIAEGT
SGAP    ------------------------------------------APDIPLANVKAHLTQLS
hGCP II ---------------------ANEYAYRRGIAEAVGLPSIPVHPIGYYDAQ-K
                                 *            :  :

hQC     SISEMWQNDLQPLLIERYPGSPGSYAARQHIMQRIQRLQADWVLEIDTFLSQTPYGYRSF
SGAP    TIAAN--NGGN------RAHGRPGYKASVDYVKAKLD--AAGYTTLQQFTSGGATGYNLI
hGCP II LLEKM--GGSAP---PDSSWRGSLKVPYNVGPGFTGNFSTQKVKMHIHSTNEVTRIYNVI
                                                  * hQC     SNIISTLNPTAKRHLVLACHYDSKYFSHWNNRVFVGATDSAVPCAMMLELAR---ALDKK
SGAP    ANWPG-GDP--NKVLMAGAHLDS--VSSG------AGINDNGSGSAAVLETAL---AVSRA
hGCP II GTLRGAVEP--DRYVILGGHRDS------W----VFGGIDPQSGAAVVHEIVRSFGTLKKE
                                                 *         :  :

hQC     LLSLKTVSDSKPDLSLQLIFFDGEEAFLHWSPQDSLYGSRHLAAKMASTPHPPGARGTSQ
SGAP    GY---Q-----PDKHLRFAWWGAEELGLIGS-----KFY-----VNNLPSADR---SK
hGCP II GW---R-----PRRTILFASWDAEEFGLLGS-----TEW-------AEENSR--LLQ
                  :  ::  :   ::**                * hQC     LHGMDLLVLLDLIGAPNPTFPNFF---PNSARWFERLQAIEHELH------ELGLLKDHSLEGR
SGAP    LAG----YLNFDMIGSPNPGYFVYDDDPVIEKTFKNYFAGLNVPT---EIETEGDGRSDHA
hGCP II ERG-VAYINADSSIEGNYTLRVDCT-PLMYSLVHNLTKELKSPDEGFEGKSLYESWTKKS
                                        * hQC     Y---FQNYSY----G-G------VIQDD-HIPFLRRGVP-VLHLIPSPFPEVWHTMDDNEE
SGAP    P---FKNWGVP--VG-G------LFTGAGYTKSAAQAQK-WGGTAGQAFDRCYHSSCDSLS
hGCP II PSPEFSGMPRISKLGSGNDFEVFQRLGIASGRARYTKNWETNKFSGYP-LYHSVVETYE
                                              :* hQC     NLDESTID-N-LNKILQVFVLEYLHL---         (SEQ ID NO: 36)
SGAP    NINDTALDRNSDAAAHAIWTLSSGTGEPPT        (SEQ ID NO: 37)
hGCP II -LVEKFYD--PMFKYHLTVAQVRGGMVFEL        (SEQ ID NO: 38)
         : :                  *
```

USE OF INHIBTORS OF GLUTAMINYL CYCLASES FOR TREATMENT AND PREVENTION OF DISEASE

CROSS-REFERENCE TO RELATED APPLICATIONS

The present application is a Divisional application of U.S. application Ser. No. 10/839,017, filed on May 5, 2004, which issued as U.S. Pat. No. 7,381,537 on Jun. 3, 2008, which claims priority to U.S. Provisional Application Ser. No. 60/468,014, filed on May 5, 2003; U.S. Provisional Application Ser. No. 60/468,043, filed on May 5, 2003; and U.S. Provisional Application Ser. No. 60/512,038, filed on Oct. 15, 2003. Each of the above applications are incorporated herein by reference in their entirety to the extent permitted by law. The present application also claims priority to all three Provisional applications.

INCORPORATION BY REFERENCE OF SEQUENCE LISTING

The Sequence Listing, which is a part of the present disclosure, includes a computer readable form and a written sequence listing comprising nucleotide and/or amino acid sequences of the present invention. The sequence listing information recorded in computer readable form is identical to the written sequence listing. The subject matter of the Sequence Listing is incorporated herein by reference in its entirety.

FIELD OF THE INVENTION

The invention relates to glutaminyl cyclase (QC, EC 2.3.2.5) that catalyzes the intramolecular cyclization of N-terminal glutamine residues into pyroglutamic acid (5-oxo-proline, pGlu*) under liberation of ammonia and the intramolecular cyclization of N-terminal glutamate residues into pyroglutamic acid under liberation of water.

The present invention identifies mammalian QCs as metalloenzymes, provides novel physiological substrates of QC in mammals and the use of effectors of QC and pharmaceutical compositions comprising effectors of QC for the treatment of conditions that can be treated by modulation of QC-activity. Additionally, it is shown that metal interaction is a useful approach for development of QC inhibitors.

In a preferred embodiment, the present invention provides the use of effectors of QC activity in combination with inhibitors of DP IV or DP IV-like enzymes for the treatment or alleviation of conditions that can be treated by modulation of QC- and/or DP IV-activity.

A screening method is also provided for the identification and selection of effectors of QC activity.

BACKGROUND

Glutaminyl cyclase (QC, EC 2.3.2.5) catalyzes the intramolecular cyclization of N-terminal glutamine residues into pyroglutamic acid (pGlu*) liberating ammonia. A QC was first isolated by Messer from the latex of the tropical plant *Carica papaya* in 1963 (Messer, M. 1963 *Nature* 4874, 1299). 24 years later, a corresponding enzymatic activity was discovered in animal pituitary (Busby, W. H. J. et al. 1987 *J Biol Chem* 262, 8532-8536; Fischer, W. H. and Spiess, J. 1987 *Proc Natl Acad Sci U S A* 84, 3628-3632). For the mammalian QC, the conversion of Gln into pGlu by QC could be shown for the precursors of TRH and GnRH (Busby, W. H. J. et al. 1987 *J Biol Chem* 262, 8532-8536; Fischer, W. H. and Spiess, J. 1987 *Proc Natl Acad Sci U S A* 84, 3628-3632). In addition, initial localization experiments of QC revealed a co-localization with its putative products of catalysis in bovine pituitary, further improving the suggested function in peptide hormone synthesis (Bockers, T. M. et al. 1995 *J Neuroendocrinol* 7, 445-453). In contrast, the physiological function of the plant QC is less clear. In case of the enzyme from *C. papaya*, a role in the plant defense against pathogenic microorganisms was suggested (El Moussaoui, A. et al. 2001 *Cell Mol Life Sci* 58, 556-570). Putative QCs from other plants were identified by sequence comparisons recently (Dahl, S. W. et al. 2000 *Protein Expr Purif* 20, 27-36) The physiological function of these enzymes, however, is still ambiguous.

The QCs known from plants and animals show a strict specificity for L-Glutamine in the N terminal position of the substrates and their kinetic behavior was found to obey the Michaelis-Menten equation (Pohl, T. et al. 1991 *Proc Natl Acad Sci U S A* 88, 10059-10063; Consalvo, A. P. et al. 1988 *Anal Biochem* 175, 131-138; Gololobov, M. Y. et al. 1996 *Biol Chem Hoppe Seyler* 377, 395-398). A comparison of the primary structures of the QCs from *C. papaya* and that of the highly conserved QC from mammals, however, did not reveal any sequence homology (Dahl, S. W. et al. 2000 *Protein Expr Purif* 20, 27-36). Whereas the plant QCs appear to belong to a new enzyme family (Dahl, S. W. et al. 2000 *Protein Expr Purif* 20, 27-36), the mammalian QCs were found to have a pronounced sequence homology to bacterial aminopeptidases (Bateman, R. C. et al. 2001 *Biochemistry* 40, 11246-11250), leading to the conclusion that the QCs from plants and animals have different evolutionary origins.

EP 02 011 349.4 discloses polynucletides encoding insect glutaminyl cyclase, as well as polypeptides encoded thereby. This application further provides host cells comprising expression vectors comprising polynucleotides of the invention. Isolated polypeptides and host cells comprising insect QC are useful in methods of screening for agents that reduce glutaminyl cyclase activity. Such agents are described as useful as pesticides.

Alzheimer's disease (AD) is characterized by abnormal accumulation of extracellular amyloidotic plaques closely associated with dystrophic neurones, reactive astrocytes and microglia (Terry, R. D. and Katzman, R. 1983 *Ann Neurol* 14, 497-506; Glenner, G. G. and Wong, C. W. 1984 *Biochem Biophys Res Comm* 120, 885-890; Intagaki, S. et al. 1989 *J Neuroimmunol* 24, 173-182; Funato, H. et al. 1998 *Am J Pathol* 152, 983-992; Selkoe, D. J. 2001 *Physiol Rev* 81, 741-766). Amyloid-β (Aβ) peptides are the primary components of senile plaques and are considered to be directly involved in the pathogenesis and progression of AD, a hypothesis supported by genetic studies (Glenner, G. G. and Wong, C. W. 1984 *Biochem Biophys Res Comm* 120, 885-890; Borchelt, D. R. et al. 1996 *Neuron* 17, 1005-1013; Lemere, C. A. et al. 1996 *Nat Med* 2, 1146-1150; Mann, D. M. and Iwatsubo, T. 1996 *Neurodegeneration* 5, 115-120; Citron, M. et al. 1997 *Nat Med* 3, 67-72; Selkoe, D. J. 2001 *Physiol Rev* 81, 741-766). Aβ is generated by proteolytic processing of the β-amyloid precursor protein (APP) (Kang, J. et al. 1987 *Nature* 325, 733-736; Selkoe, D. J. 1998 *Trends Cell Biol* 8, 447-453), which is sequentially cleaved by β-secretase at the N-terminus and by γ-secretase at the C-terminus of Aβ (Haass, C. and Selkoe, D. J. 1993 *Cell* 75, 1039-1042; Simons, M. et al. 1996 *J Neurosci* 16 899-908). In addition to the dominant Aβ peptides starting with L-Asp at the N-terminus (Aβ1-42/40), a great heterogeneity of N-terminally truncated forms occurs in senile plaques. Such shortened peptides are reported to be more neurotoxic in vitro and to aggregate more rapidly than the full-length isoforms (Pike, C. J. et al. 1995 *J Biol Chem* 270 23895-23898). N-truncated peptides are known to be overproduced in early onset familial AD (FAD) subjects (Saido, T. C. et al. 1995 *Neuron* 14, 457-466; Russo, C. et al. 2000 *Nature* 405, 531-532), to appear early and to increase with age in Down's syndrome (DS) brains (Russo, C. et al. 1997 *FEBS Lett* 409, 411-416, Russo, C. et al. 2001 *Neurobiol Dis* 8, 173-180; Tekirian, T. L. et al. 1998 *J Neuropathol Exp Neurol* 57, 76-94). Finally, their amount reflects the progressive severity of the disease (Russo, C. et al. 1997 *FEBS Lett* 409, 411-416). Additional post-translational processes may further modify the N-terminus by isomerization or racemization of the aspartate at position 1 and 7 and by cyclization of glutamate at residues 3 and 11. Pyroglutamate-containing isoforms at position 3 [pGlu$^3$] Aβ3-40/42] represent the prominent forms—approximately 50% of the total Aβ amount—of the N-truncated species in senile plaques (Mori, H. et al. 1992 *J Biol Chem* 267, 17082-17086, Saido, T. C. et al. 1995 *Neuron* 14, 457-466; Russo, C. et al. 1997 *FEBS Lett* 409, 411-416; Tekirian, T. L. et al. 1998 *J Neuropathol Exp Neurol* 57, 76-94; Geddes, J. W. et al. 1999 *Neurobiol Aging* 20, 75-79; Harigaya, Y. et al. 2000 *Biochem Biophys Res Commun* 276, 422-427) and they are also present in pre-amyloid lesions (Lalowski, M. et al. 1996 *J Biol Chem* 271, 33623-33631). The accumulation of AβN3(pE) peptides is likely due to the structural modification that enhances aggregation and confers resistance to most amino-peptidases (Saido, T. C. et al. 1995 *Neuron* 14, 457-466; Tekirian, T. L. et al. 1999 *J Neurochem* 73, 1584-1589). This evidence provides clues for a pivotal role of AβN3(pE) peptides in AD pathogenesis. However, relatively little is known about their neurotoxicity and aggregation properties (He, W. and Barrow, C. J. 1999 *Biochemistry* 38, 10871-10877; Tekirian, T. L. et al. 1999 *J Neurochem* 73, 1584-1589). Moreover, the action of these isoforms on glial cells and the glial response to these peptides are completely unknown, although activated glia is strictly associated to senile plaques and might actively contribute to the accumulation of amyloid deposits. In recent studies the toxicity, aggregation properties and catabolism of Aβ1-42, Aβ1-40, [pGluβ]Aβ3-42 and [pGluβ]Aβ3-40 peptides were investigated in neuronal and glial cell cultures, and it was shown that pyroglutamate modification exacerbates the toxic properties of Aβ-peptides and also inhibits their degradation by cultured astrocytes. Shirotani et al. investigated the generation of [pGluβ]Aβ peptides in primary cortical neurons infected by Sindbis virus in vitro. They constructed amyloid precursor protein complementary DNAs, which encoded a potential precursor for [pGluβ]Aβ by amino acid substitution and deletion. For one artificial precursor starting with a N-terminal glutamine residue instead of glutamate in the natural precursor, a spontaneous conversion or an enzymatic conversion by glutaminyl cyclase to pyroglutamate was suggested. The cyclization mechanism of N-terminal glutamate at position 3 in the natural precursor of [pGluβ]Aβ was not determined in vivo (Shirotani, K., Tsubuki, S., Lee, H. J., Maruyama, K., and Saido, T. C. (2002) *Neurosci Lett* 327, 25-28)

Dipeptidyl peptidase IV (DP IV) is a post-proline (to a lesser extent post-alanine, post-serine or post-glycine) cleaving serine protease found in various tissues of the body including kidney, liver, and intestine and cleaves N-terminal dipeptides from a peptide chain. Recently it was shown that DP IV plays an important role in neuropeptide metabolism, T-cell activation, attachment of cancer cells to the endothelium and the entry of HIV into lymphoid cells. See therefore WO 02/34242, WO 02/34243, WO 03/002595 and WO 03/002596.

It is known that DP IV inhibitors may be useful for the treatment of impaired glucose tolerance and diabetes mellitus (International Patent Application, Publication Number WO 99/61431, Pederson, R. A. et al. 1998 *Diabetes* 47, 1253-1258 and Pauly, R. P. et al. 1999 *Metabolism* 48, 385-389). In particular WO 99/61431 discloses DP IV inhibitors comprising an amino acid residue and a thiazolidine or pyrrolidine group, and salts thereof, especially L-threo-isoleucyl thiazolidine, L-allo-isoleucyl thiazolidine, L-threo-isoleucyl pyrrolidine, L-allo-isoleucyl thiazolidine, L-allo-isoleucyl pyrrolidine, and salts thereof.

Further examples of low molecular weight dipeptidyl peptidase IV inhibitors are agents such as tetrahydroisoquinolin-3-carboxamide derivatives, N-substituted 2-cyanopyroles and -pyrrolidines, N—(N'-substituted glycyl)-2-cyanopyrrolidines, N-(substituted glycyl)-thiazolidines, N-(substituted glycyl)-4-cyanothiazolidines, amino-acyl-borono-prolyl-inhibitors, cyclopropyl-fused pyrrolidines and heterocyclic compounds. Inhibitors of dipeptidyl peptidase IV are described in U.S. Pat. No. 6,380,398, U.S. Pat. No. 6,011,155; U.S. Pat. No. 6,107,317; U.S. Pat. No. 6,110,949; U.S. Pat. No. 6,124,305; U.S. Pat. No. 6,172,081; WO 95/15309, WO 99/61431, WO 99/67278, WO 99/67279, DE 198 34 591, WO 97/40832, DE 196 16 486 C 2, WO 98/19998, WO 00/07617, WO 99/38501, WO 99/46272, WO 99/38501, WO 01/68603, WO 01/40180, WO 01/81337, WO 01/81304, WO 01/55105, WO 02/02560 and WO 02/14271, WO 02/04610, WO 02/051836, WO 02/068420, WO 02/076450; WO 02/083128, WO 02/38541, WO 03/000180, WO 03/000181, WO 03/000250, WO 03/002530, WO 03/002531, WO 03/002553, WO 03/002593, WO 03/004496, WO 03/024942 and WO 03/024965, the teachings of which are herein incorporated by reference in their entirety, especially concerning these inhibitors, their definition, uses and their production.

SUMMARY OF THE INVENTION

The present invention provides novel physiological substrates of QC in mammals, Aβ3-40/42, [Gln$^3$]Aβ-40/42, [Glu$^{11}$]Aβ11-40/42, [Gln$^{11}$]Aβ1-40/42, [Gln$^1$]Gastrin, [Gln$^1$]Neurotensin, [Gln$^1$]FPP, [Gln$^1$]CCL 2, [Gln$^1$]CCL 7, [Gln$^1$]CCL 8, [Gln$^1$]CCL 16, [Gln$^1$]CCL 18, [Gln$^1$]Fractalkine, [Gln$^1$]Orexin A, [Gln$^3$]glucagon3-29 and [Gln$^5$]substance P5-11 and the use of effectors of QC and pharmaceutical compositions comprising effectors of QC for the treatment of conditions that can be treated by modulation of QC activity.

It was shown by inhibition studies that human QC is a metal-dependent transferase. QC apoenzyme could be reactivated most efficiently by zinc ions, and the metal-binding motif of zinc-dependent aminopeptidases is also present in human QC. Compounds interacting with the active-site bound metal are potent inhibitors.

Unexpectedly, it was shown that recombinant human QC as well as QC-activity from brain extracts catalyze both, the N-terminal glutaminyl as well as glutamate cyclization. Most striking is the finding, that cyclase-catalyzed Glu$^1$-conversion is favored around pH 6.0 while Gln$^1$-conversion to pGlu-derivatives occurs with a pH-optimum of around 8.0. Since the formation of pGlu-Aβ-related peptides can be suppressed by inhibition of recombinant human QC and QC activity from pig pituitary extracts, the enzyme QC is a target in drug development for treatment of Alzheimer's disease.

By administering effectors of QC activity to a mammal it can be possible to prevent or alleviate or treat conditions selected from Alzheimer's disease, Down Syndrome, ulcer disease and gastric cancer with or w/o *Heliobacter pylori* infections, pathogenic psychotic conditions, schizophrenia, infertility, neoplasia, inflammatory host responses, cancer, psoriasis, rheumatoid arthritis, atherosclerosis, impaired humoral and cell-mediated immune responses, leukocyte adhesion and migration processes in the endothelium, impaired food intake, sleep-wakefulness, impaired homeostatic regulation of energy metabolism, impaired autonomic function, impaired hormonal balance and impaired regulation of body fluids.

Further, by administration of effectors of QC activity to a mammal it can be possible to stimulate gastrointestinal tract cell proliferation, preferably proliferation of gastric mucosal cells, epithelial cells, acute acid secretion and the differentiation of acid producing parietal cells and histamine enterochromaffin-like cells.

Furthermore, by administration of effectors of QC activity to a mammal it can be possible to suppress the proliferation of myeloid progenitor cells.

In addition, administration of QC inhibitors can lead to suppression of male fertility.

In a preferred embodiment, the present invention provides the use of effectors of QC activity in combination with inhibitors of DP IV or DP IV-like enzymes for the treatment or alleviation of conditions that can be treated by modulation of QC- and/or DP IV-activity.

The present invention provides pharmaceutical compositions for parenteral, enteral or oral administration, comprising at least one effector of QC optionally in combination with customary carriers and/or excipients; or comprising at least one effector of QC in combination with at least one DP IV-inhibitor, optionally in combination with customary carriers and/or excipients.

Screening methods are also provided for the identification and selection of effectors of QC.

BRIEF DESCRIPTION OF THE DRAWINGS

Further understanding of these and other aspects of the present invention will be had by reference to the figures wherein:

FIG. 21 Sequence alignment of human QC (hQC) and other M28 family members of the metallopeptidase Clan MH. Multiple sequence alignment was performed using ClustalW at ch.EMBnet.org with default settings. The conservation of the zinc-ion ligating residues is shown for human QC (hQC; GenBank X71125), the Zn-dependent aminopeptidase from *Streptomyces griseus* (SGAP; Swiss-Prot P80561), and within the N-acetylated-alpha-linked acidic dipeptidase (NAALADase I) domain (residues 274-587) of the human Glutamate carboxypeptidase II (hGCP II; Swiss-Prot Q04609). The amino acids involved in metal binding are typed in bold and underlined. In case of human QC, these residues are the putative counterparts to the peptidases.

PEPTIDE SEQUENCES

Figure 1:
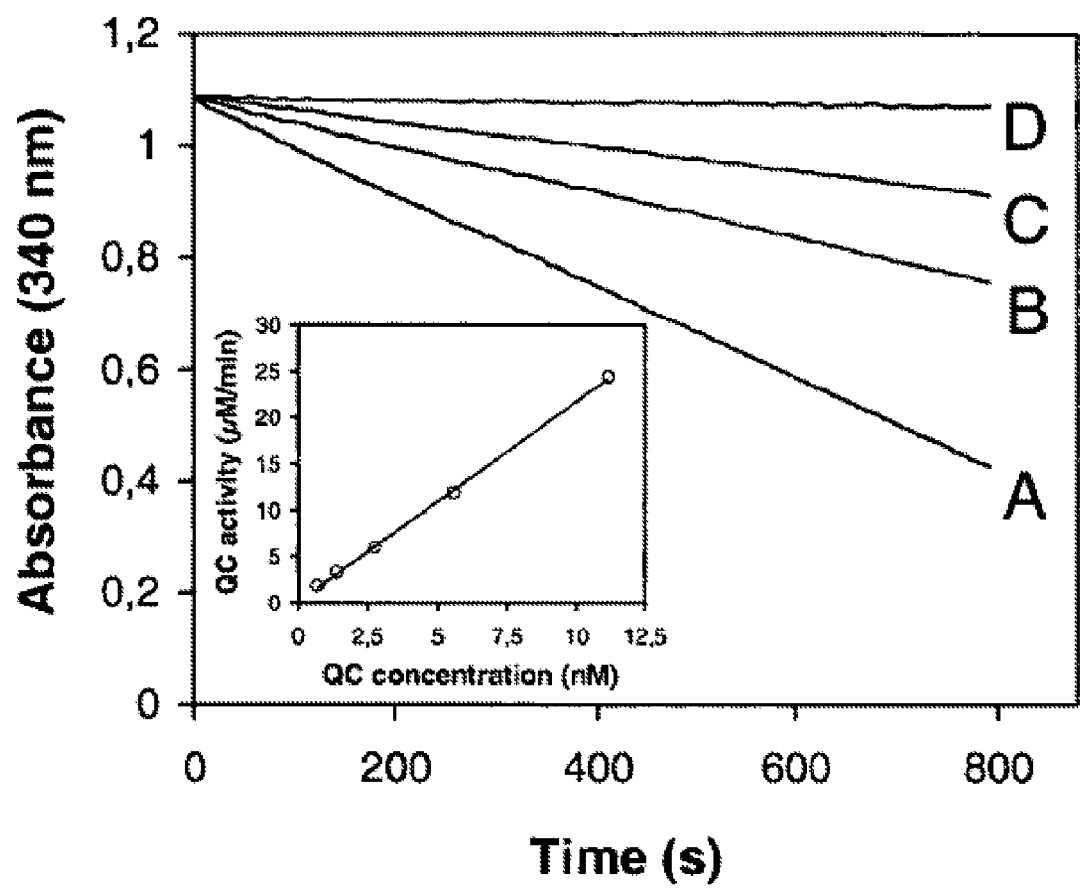
FIG. 1 shows progress curves of the cyclization of H-Gln-Ala-OH, catalyzed by human QC, monitoring the decrease in absorbance at 340 nm. The samples contained 0.3 mM NADH/H$^+$, 14 mM α-Ketoglutaric acid, 30 U/ml glutamic dehydrogenase and 1 mM H-Gln-Ala-OH. From curve A-D, varying concentrations of QC were applied: A, 10 mU/ml, B, 5 mU/ml, C, 2.5 mU/ml. In case of curve D, QC was omitted. A linear relationship was obtained between the QC concentration and the observed activity (inset).

The peptides mentioned and used herein have the following sequences:

```
Aβ1-42:                                    (SEQ ID NO: 39)
Asp-Ala-Glu-Phe-Arg-His-Asp-Ser-Gly-Tyr-Glu-Val-

His-His-Gln-Lys-Leu-Val-Phe-Phe-Ala-Glu-Asp-Val-

Gly-Ser-Asn-Lys-Gly-Ala-Ile-Ile-Gly-Leu-Met-Val-

Gly-Gly-Val-Val-lle-Ala

Aβ1-40:                                    (SEQ ID NO: 40)
Asp-Ala-Glu-Phe-Arg-His-Asp-Ser-Gly-Tyr-Glu-Val-

His-His-Gln-Lys-Leu-Val-Phe-Phe-Ala-Glu-Asp-Val-

Gly-Ser-Asn-Lys-Gly-Ala-Ile-Ile-Gly-Leu-Met-Val-

Gly-Gly-Val-Val

Aβ3-42:                                    (SEQ ID NO: 41)
Glu-Phe-Arg-His-Asp-Ser-Gly-Tyr-Glu-Val-His-His-

Gln-Lys-Leu-Val-Phe-Phe-Ala-Glu-Asp-Val-Gly-Ser-

Asn-Lys-Gly-Ala-Ile-Ile-Gly-Leu-Met-Val-Gly-Gly-

Val-Val-Ile-Ala

Aβ3-40:                                    (SEQ ID NO: 42)
Glu-Phe-Arg-His-Asp-Ser-Gly-Tyr-Glu-Val-His-His-

Gln-Lys-Leu-Val-Phe-Phe-Ala-Glu-Asp-Val-Gly-Ser-

Asn-Lys-Gly-Ala-Ile-Ile-Gly-Leu-Met-Val-Gly-Gly-

Val-Val

Aβ1-11a:                                   (SEQ ID NO: 43)
Asp-Ala-Glu-Phe-Arg-His-Asp-Ser-Gly-Tyr-Glu-NH₂

Aβ3-11a:                                   (SEQ ID NO: 44)
Glu-Phe-Arg-His-Asp-Ser-Gly-Tyr-Glu-NH₂

Aβ1-21a:                                   (SEQ ID NO: 45)
Asp-Ala-Glu-Phe-Arg-His-Asp-Ser-Gly-Tyr-Glu-Val-

His-His-Gln-Lys-Leu-Val-Phe-Phe-Ala-NH₂

Aβ3-21a:                                   (SEQ ID NO: 46)
Glu-Phe-Arg-His-Asp-Ser-Gly-Tyr-Glu-Val-His-His-

Gln-Lys-Leu-Val-Phe-Phe-Ala-NH₂
```

-continued

```
Gln³-Aβ3-40:                                    (SEQ ID NO: 47)
Gln-Phe-Arg-His-Asp-Ser-Gly-Tyr-Glu-Val-His-His-

Gln-Lys-Leu-Val-Phe-Phe-Ala-Glu-Asp-Val-Gly-Ser-

Asn-Lys-Gly-Ala-Ile-Ile-Gly-Leu-Met-Val-Gly-Gly-

Val-Val

Gln³-Aβ3-21a:                                   (SEQ ID NO: 48)
Gln-Phe-Arg-His-Asp-Ser-Gly-Tyr-Glu-Val-His-His-

Gln-Lys-Leu-Val-Phe-Phe-Ala-NH₂

Gln³-Aβ1-11a:                                   (SEQ ID NO: 49)
Asp-Ala-Gln-Phe-Arg-His-Asp-Ser-Gly-Tyr-Glu-NH₂

Gln³-Aβ3-11a:                                   (SEQ ID NO: 50)
Gln-Phe-Arg-His-Asp-Ser-Gly-Tyr-Glu-NH₂
```

DETAILED DESCRIPTION OF THE INVENTION

The present invention provides effectors of glutaminyl cyclase (QC) for
a) the treatment of diseases in mammals that can be treated by modulation of QC activity in vivo and/or
b) b) the modulation of physiological processes based on the action of pGlu-containing peptides caused by modulation of QC activity.

Furthermore, the present invention provides compounds for the inhibition of glutaminyl cyclase (QC, EC 2.3.2.5) and/or QC-like enzymes in a mammal and the use of inhibitors of QC activity for the treatment of pathological conditions related to QC activity.

The present invention also provides a new method for the treatment of Alzheimer's disease and Down Syndrome. The N-termini of amyloid β-peptides deposited in Alzheimer's disease and Down syndrome brain bear pyroglutamic acid. The pGlu formation is an important event in the development and progression in the disease, since the modified amyloid β-peptides show an enhanced tendency to β-amyloid aggregation and toxicity, likely worsening the onset and progression of the disease. (Russo, C. et al. 2002 *J Neurochem* 82, 1480-1489).

In contrast, in the natural Aβ-peptides (3-40/42), glutamic acid is present as an N-terminal amino acid. There is no enzymic conversion of Glu to pGlu known to date. Moreover, spontaneous cyclization of Glu-peptides to pGlu-peptides has not been observed as yet. Therefore one aspect of the present invention was to determine the role of QC in Alzheimer's disease and Down Syndrome. This aspect was addressed by the synthesis of Aβ3-11 and Aβ1-11, containing the amino acid glutamine instead of glutamic acid at position three, the determination of the substrate characteristics of these modified amyloid β-peptides against QC, DP IV and DP IV-like enzymes and aminopeptidases and the use of inhibitors of QC to prevent the formation of pGlu from a N-terminal glutaminyl residue of the amyloid β-derived peptides 1-11 and 3-11. The results are shown in example 8. The applied method is described in example 3.

To date, there are no hints indicating an involvement of QC in the progression of the disease, because glutamic acid is the N-terminal amino acid in Aβ (3-40/42, or 11-40/42). But, QC is the only known enzyme capable of forming pGlu at the N-terminus of peptides. Other aspects of the present invention concern the following findings and discoveries:

a) In a side reaction, QC catalyzes the cyclization of glutamic acid to pyroglutamic acid at very low rates,
b) Glutamic acid of APP or its subsequently formed amyloid-β-peptides is converted into glutamine post-translationally by an unknown enzymatic activity and in a second step, QC catalyzes the cyclization of glutamine into pyroglutamic acid after processing of the amyloid β-peptide N-terminus,
c) Glutamic acid is converted into glutamine post-translationally by a chemical catalysis or autocatalysis and subsequently, QC catalyzes the cyclization of glutamine to pyroglutamic acid after processing of the amyloid β-peptide N-terminus,
d) There are mutations in the APP gene, which encode the amyloid β-protein, leading to Gln instead of Glu in position 3. After translation and processing of the N-terminus, QC catalyzes the cyclization of glutamine to pyroglutamic acid,
e) Glutamine is incorporates into the nascent peptide chain of APP, due to a malfunction of an unknown enzymatic activity and subsequently, QC catalyzes the cyclization of N-terminally glutamine to pyroglutamic acid after processing of the amyloid β-peptide N-terminus.

QC is involved in the critical step in all five cases listed above, namely the formation of pyroglutamic acid that favors the aggregation of amyloid β-peptides. Thus, an inhibition of QC leads to a prevention of the precipitation of the plaque-forming Aβ3-40/41/43 or Aβ11-40/41/43, causing the onset and progression of Alzheimer's disease and Down Syndrome, independently of the mechanism by which cyclization occurs.

Glutamate is found in positions 3, 11 and 22 of the amyloid β-peptide. Among them the mutation from glutamic acid (E) to glutamine (Q) in position 22 (corresponding to amyloid precursor protein APP 693, Swissprot P05067) has been described as the so called Dutch type cerebroarterial amyloidosis mutation.

The β-amyloid peptides with a pyroglutamic acid residue in position 3, 11 and/or 22 have been described to be more cytotoxic and hydrophobic than Aβ1-40/42/43 (Saido T. C. 2000 *Medical Hypotheses* 54(3): 427-429).

The multiple N-terminal variations can be generated by the β-secretase enzyme β-site amyloid precursor protein-cleaving enzyme (BACE) at different sites (Huse J. T. et al. 2002 *J. Biol. Chem.* 277 (18): 16278-16284), and/or by aminopeptidase processing. In all cases, cyclization can take place according to a)-e) as described above.

So far, there was no experimental evidence supporting the enzymatic conversion of Glu1 peptides into pGlu-peptides by an unknown glutamyl cyclase (EC) corresponding to pathway a) (Garden, R. W., Moroz, T. P., Gleeson, J. M., Floyd, P. D., Li, L. J., Rubakhin, S. S., and Sweedler, J. V. (1999) *J Neurochem* 72, 676-681; Hosoda R. et al. (1998) *J Neuropathol Exp Neurol.* 57, 1089-1095). To date, no such enzyme activity has been identified, capable to cyclize Glu1-peptides which are protonated N-terminally and possess a negatively charged $Gl^{u1}$ γ-carboxylate moiety under mildly alkaline pH-conditions.

QC-activity against $Gln^1$-substrates is dramatically reduced below pH 7.0. In contrast, it appears that $Glu^1$-conversion can occur at acidic reaction conditions (Iwatsubo, T., Saido, T. C., Mann, D. M., Lee, V. M., and Trojanowski, J. Q. (1996) *Am J Pathol* 149, 1823-1830; Russo, C., Saido, T. C., DeBusk, L. M., Tabaton, M., Gambetti, P., and Teller, J. K. (1977) *FEBS Lett* 409, 411 416; Russo, C., Salis, S., Dolcini, V., Venezia, V., Song, X. H., Teller, J. K., and Schettini, G. (2001) *Neurobiol Dis* 8, 173-180; Tekirian, T. L., Saido, T. C., Markesbery, W. R., Russell, M. J., Wekstein, D. R., Patel, E., and Geddes, J. W. (1998) *J Neuropathol Exp Neurol.* 57, 76-94; Russo, C., Violani, E., Salis, S., Venezia, V., Dolcini, V., Damonte, G., Benatti, U., DArrigo, C., Patrone, E., Carlo, P., and Schettini, G. (2002) *J Neurochem* 82, 1480-1489; Hosoda, R., Saido, T. C., Otvos, L., Jr., Arai, T., Mann, D. M., Lee, V. M., Trojanowski, J. Q., and Iwatsubo, T. (1998) *J Neuropathol Exp Neurol.* 57, 1089-1095; Garden, R. W., Moroz, T. P., Gleeson, J. M., Floyd, P. D., Li, L. J., Rubakhin, S. S., and Sweedler, J. V. (1999) *J Neurochem* 72, 676-681).

According to the present invention it was investigated whether QC is able to recognize and to turnover amyloid-β derived peptides under mild acidic conditions. Therefore, the peptides [Gln³]Aβ1-11a, Aβ3-11a, [Gln³]Aβ3-11a, Aβ3-21a, [Gln³]Aβ3-21a and [Gln³]Aβ3-40 as potential substrates of the enzyme were synthesized and investigated. These sequences were chosen for mimicking natural N-terminally and C-terminally truncated [Glu³]Aβ peptides and [Gln³]Aβ peptides which could occur due to posttranslational Glu-amidation.

In the present invention it was shown that papaya and human QC catalyze both glutaminyl and glutamyl cyclization. Apparently, the primary physiological function of QC is to finish hormone maturation in endocrine cells by glutamine cyclization prior or during the hormone secretion process. Such secretory vesicles are known to be acidic in pH. Thus, a side activity of the enzyme in the narrow pH-range from 5.0 to 7.0 could be its newly discovered glutamyl cyclase activity transforming also Glu-Aβ peptides. However, due to the much slower occurring Glu-cyclization compared to Gln-conversion, it is questionable whether the glutamyl cyclization plays a significant physiological role. In the pathology of neurodegenerative disorders, however, the glutamyl cyclization is of relevance.

Figure 17:
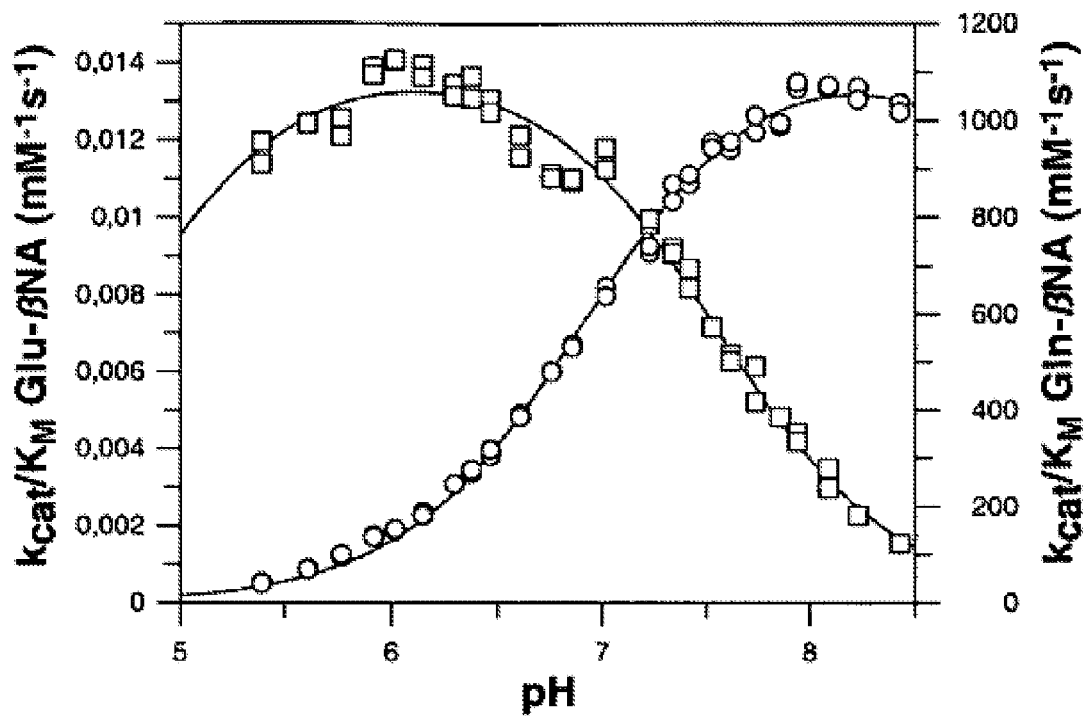
FIG. 17 shows the pH-dependence of the conversion of Gln-βNA (circles) and Glu-βNA (squares), determined under first-order rate-law conditions (S<<$K_M$). Substrate concentration was 0.01 mM and 0.25 mM, respectively. For both determinations, a three-component buffer system was applied consisting of 0.05 M acetic acid, 0.05 M pyrophosphoric acid and 0.05 M Tricine. All buffers were adjusted to equal conductivity by addition of NaCl, in order to avoid differences in ionic strength. The data were fitted to equations that account for two dissociating groups revealing $pK_a$-values of 6.91±0.02 and 9.5±0.1 for Gln-βNA and 4.6±0.1 and 7.55±0.02 for Glu-βNA. The pKa-values of the respective substrate amino groups, determined by titration, were 6.97±0.01 (Gln-βNA) and 7.57±0.05 (Glu-βNA). All determinations were carried out at 30° C.

Investigating the pH-dependency of this enzymatic reaction, we found that the unprotonated N-terminus was essential for the cyclization of Gln¹-peptides and accordingly that the $pK_a$-value of the substrate was identical to the $pK_a$ value for QC-catalysis (see FIG. 17). Thus, QC stabilizes the intramolecular nucleophilic attack of the unprotonated α-amino moiety on the γ-carbonyl carbon electrophilically activated by amidation (Scheme 1).

In contrast to the monovalent charge present on N-terminal glutamine containing peptides, the N-terminal Glu-residue in Glu-containing peptides is predominantly bivalently charged around neutral pH. Glutamate exhibits $pK_a$-values of about 4.2 and 7.5 for the γ-carboxylic and for the α-amino moiety, respectively. I.e. at neutral pH and above, although the α-amino nitrogen is in part or fully unprotonated and nucleophilic, the γ-carboxylic group is unprotonated, and so exercising no electrophilic carbonyl activity. Hence, intramolecular cyclization is impossible. However, in the pH-range of about 5.2-6.5, between their respective $pK_a$-values, the two functional groups are present both in non-ionized forms, in concentrations of about 1-10% (—NH²) or 10-1% (—COOH) of total N-terminal Glu-containing peptide. As a result, over a mildly acidic pH-range species of N-terminal Glu-peptides are present which carry both groups uncharged, and, therefore, it is possible that QC could stabilize the intermediate of intramolecular cyclization to pGlu-peptide. I.e. if the γ-carboxylic group is protonated, the carbonyl carbon is electrophilic enough to allow nucleophilic attack by the unprotonated α-amino group. At this pH the hydroxyl ion functions as a leaving group (Scheme 3). These assumptions are corroborated by the pH-dependence data obtained for the QC catalyzed conversion of Glu-βNA (see example 11). In contrast to glutamine conversion of Gln-βNA by QC, the pH-optimum of catalysis shifts to the acidic range around pH 6.0, i.e. the pH-range, in which substrate molecule species are simultaneously abundant carrying a protonated γ-carboxyl and unprotonated γ-amino group. Furthermore, the kinetically determined $pK_a$-value of 7.55±0.02 is in excellent agreement with that of the α-amino group of Glu-βNA, determined by titration (7.57±0.05).

Physiologically, at pH 6.0 the second-order rate constant (or specificity constant, $k_{cat}/K_M$) of the QC-catalyzed glutamate cyclization might be in the range of 8,000 fold slower than the one for glutamine cyclization (FIG. 17). However, the nonenzymatic turnover of both model substrates Glu-βNA and Gln-βNA is negligible, being conform with the observed negligible pGlu-peptide formation in the present invention. Hence, for the pGlu-formation by QC an acceleration of at least $10^8$ can be estimated from the ratio of the enzymatic versus non-enzymatic rate constants (comparing the second-order rate constants for the enzyme catalysis with the respective nonenzymatic cyclization first-order rate constants the catalytic proficiency factor is $10^9$-$10^{10}$ M$^{-1}$ for the Gln- and the Glu-conversion, respectively). The conclusion from these data is, that in vivo only an enzymatic path resulting pGlu-formations seems conceivable.

Figure 9:
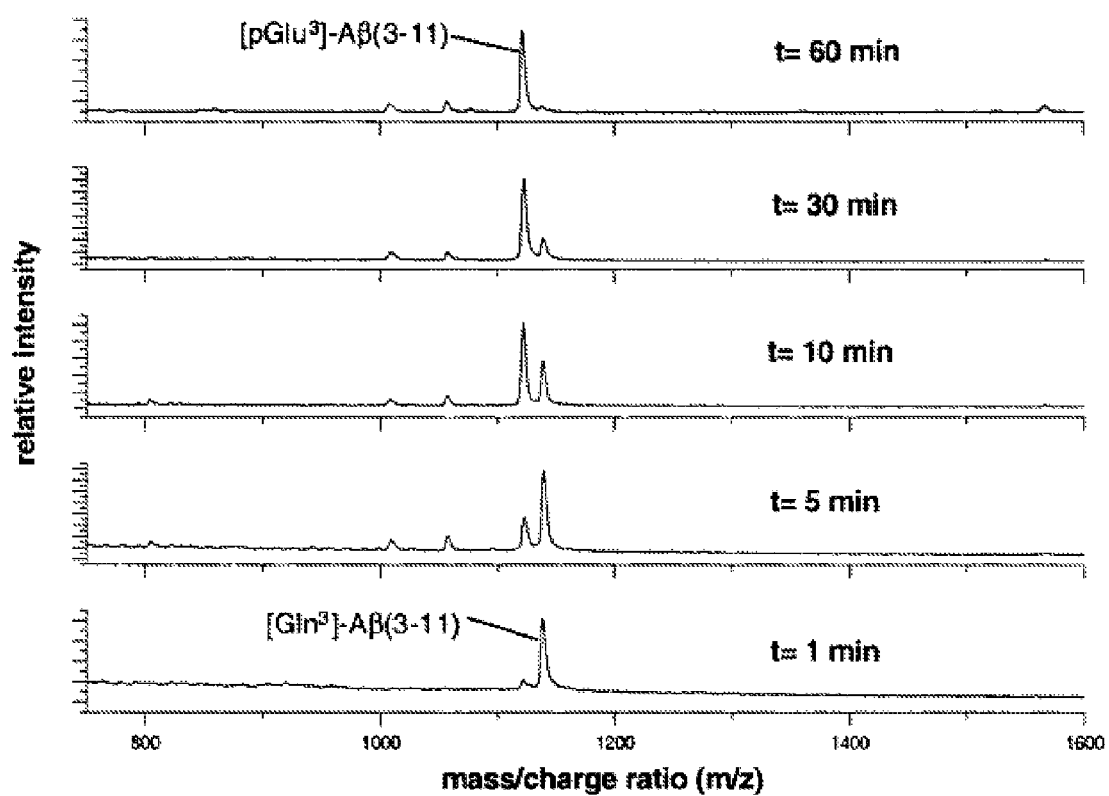
FIG. 9 shows the formation of [pGlu$^3$]Aβ3-11 from [Gln$^3$] Aβ3-11 catalyzed by QC. At the 30 times indicated, samples were removed from the assay tube, mixed with matrix solution (1:1 v/v) and subsequently the mass spectra recorded.
Figure 10:
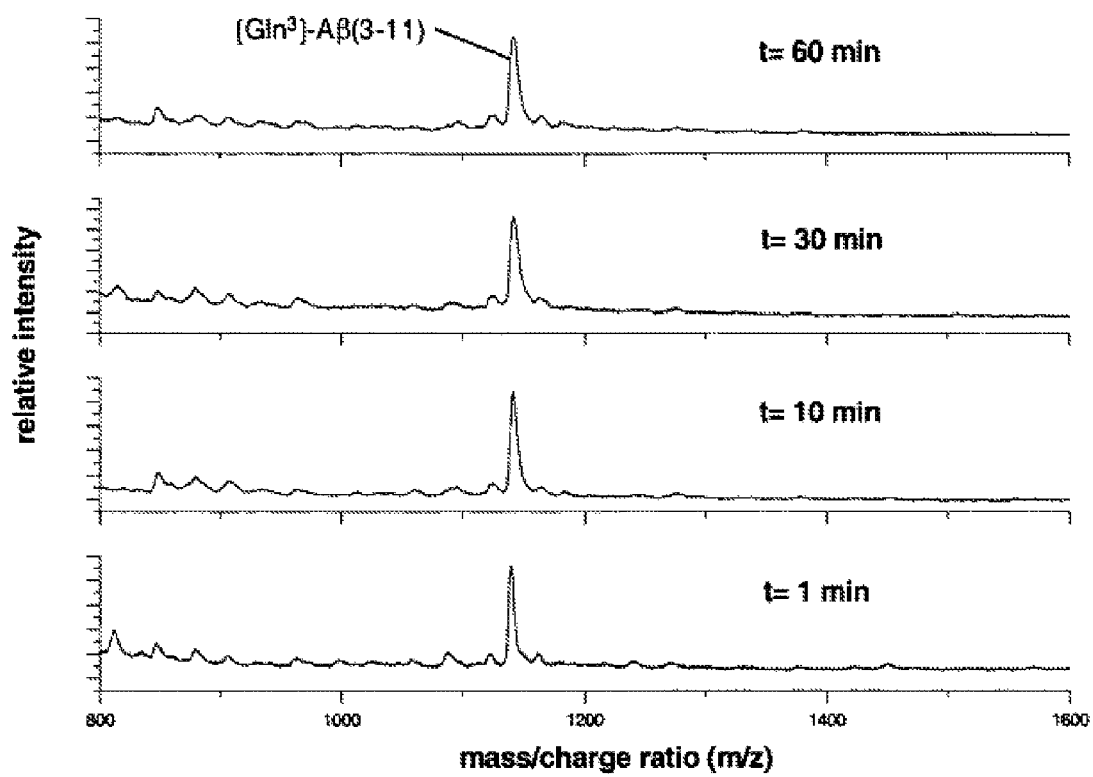
FIG. 10 shows the inhibition of the formation of [pGlu$^3$] Aβ3-11 from [Gln$^3$]Aβ3-11 by the QC-inhibitor 1,10-phenanthroline. At the times indicated from the assay tube, samples were removed, mixed with matrix solution (1:1 v/v) and subsequently the mass spectra recorded.

Since QC is highly abundant in the brain and taking into account the high turnover rate of 0.9 min$^{-1}$ recently found for the maturation of 30 μM of (Gln-)TRH-like peptide (Prokai, L., Prokai-Tatrai, K., Ouyang, X., Kim, H. S., Wu, W. M., Zharikova, A., and Bodor, N. (1999) *J Med Chem* 42, 4563-4571), one can predict a cyclization half-life of about 100 hours for an appropriate glutamate-substrate, similar reaction conditions provided. Moreover, given compartmentalization and localization of brain QC/EC in the secretory pathway, the actual in vivo enzyme and substrate concentrations and reaction conditions might be even more favorable for the enzymatic cyclization in the intact cell. And, if N-terminal Glu is transformed to Gln a much more rapid pGlu-formation mediated by QC could be expected. In vitro, both reactions were suppressed by applying inhibitors of QC/EC-activity (FIGS. 9, 10 and 15).

In summary, the present invention shows that human QC, which is highly abundant in the brain, is a likely catalyst to the formation of the amyloidogenic pGlu-Aβ peptides from Glu-Aβ and Gln-Aβ precursors which make up more than 50% of the plaque deposits found in Alzheimer's Disease. These findings identify QC/EC as a player in senile plaque formation and thus as a novel drug target in the treatment of Alzheimer's Disease.

In a second embodiment of the present invention, it was found that amyloid β-derived peptides are a substrate of dipeptidyl peptidase IV (DP IV) or DP IV-like enzymes, preferably dipeptidyl peptidase II (DPII). DP IV, DP II or other DP IV-like enzymes release a dipeptide from the N-terminus of the modified amyloid β-peptide (1-11) generating amyloid β-peptide (3-11) with glutamine as the N-terminal amino acid residue. The results are shown in example 8. Prior to cleavage by DP II, DPIV or other DP IV-like enzymes, the peptide bond between aspartic acid (residue 1 of amyloid β-peptide) and alanine (residue 2 of amyloid β-peptide) may be isomerised yielding an isoaspartyl residue as described in the literature (Kuo, Y.-M., Emmerling, M. R., Woods, A. S., Cotter, R. J., Roher, A. E. (1997) *BBRC* 237, 188-191; Shimizu, T., Watanabe, A., Ogawara, M., Mori, H. and Shirasawa, T. (2000) *Arch. Biochem. Biophys.* 381, 225-234).

These isoaspartyl residues render the amyloid β-peptide resistant against aminopeptidase degradation and consequently the core plaques contain high amounts of isoAsp¹-amyloid β-peptides, which suggests a reduced turnover at the N-terminus.

However, in the present invention it is demonstrated for the first time, that the N-terminal dipeptide H-isoAsp¹-Ala²-OH can be released by dipeptidyl peptidases especially under acidic conditions. Furthermore, it was shown that isomerization can precede also cleavage by β-secretase, and that isomerization may accelerate proteolytic processing, thus leading to liberation of an N-terminal isoaspartyl bond of isoAsp$^1$-amyloid β-peptides which subsequently is subject to turnover by DP II, DPIV or DP IV-like enzymes (Momand, J. and Clarke, S. (1987) *Biochemistry* 26, 7798-7805; Kuo, Y.-M., Emmerling, M. R., Woods, A. S., Cotter, R. J., Roher, A. E. (1997) *BBRC* 237, 188-191). Accordingly, inhibition of isoaspartyl formation may lead to the reduction of cleavage by β-secretase and, in turn, to a reduced formation of amyloid β-peptides. In addition, blockage of the isoAsp1-amyloid β-peptide turnover by inhibition of DP IT, DPIV or DP IV-like enzymes would prevent the exposure of [Glu$^3$]Aβ to QC/EC-catalyzed formation of [pGlu$^3$]Aβ.

In a third embodiment of the present invention, a combination of inhibitors of DP IV-activity and of inhibitors of QC can be used for the treatment of Alzheimer's disease and Down Syndrome.

The combined effect of DP IV and/or DP IV-like enzymes and of QC is illustrated as follows:
  a) DP IV and/or DP IV-like enzymes cleave Aβ1-40/42, a dipeptide comprising H-Asp-Ala-OH and Aβ3-40/42 are released,
  b) In a side reaction, QC catalyzes the cyclization of glutamic acid to pyroglutamic acid at very low rates,
  c) Glutamic acid is converted into glutamine at the N-terminus post translationally by an unknown enzymatic activity and subsequently, QC catalyzes the cyclization of glutamine into pyroglutamic acid after processing of the amyloid β-peptide N-terminus,
  d) Glutamic acid is converted into glutamine post-translationally by a chemical catalysis or autocatalysis and in a second step, QC catalyzes the cyclization of glutamine into pyroglutamic acid after processing of the amyloid β-peptide N terminus,
  e) There are mutations in the APP gene, which encode the amyloid β-protein, leading to Gln instead of Glu in position 3 of Aβ, After translation and processing of the N-terminus, QC catalyzes the cyclization of glutamine to pyroglutamic acid,
  f) Glutamine is incorporated into the nascent peptide chain of APP, due to a malfunction of an unknown enzymatic activity and subsequently, QC catalyzes the cyclization of N-terminally glutamine to pyroglutamic acid after processing of the amyloid β-peptide N-terminus, The N-terminal Gln-exposure to QC-activity can be also triggered by different peptidase activities. Aminopeptidases can remove sequentially Asp and Ala from the N-terminus of Aβ1-40/41/43, thus unmasking amino acid three that is prone to cyclization. Dipeptidyl peptidases, such as DP I, DP II, DP IV, DP 8, DP 9 and DP 10, remove the dipeptide Asp-Ala in one step. Hence, inhibition of aminopeptidase- or dipeptidylpeptidase-activity is useful to prevent the formation of A(β-40/41/43.

The combined effect of inhibitors of DP IV and/or DP IV-like enzymes and of activity lowering effectors of QC is illustrated in the following way:
  a) The inhibitors of DP IV and/or DP IV-like enzymes inhibit the conversion of Aβ1-40/42 to Aβ3-40/42.
  b) An N-terminal exposure of glutamic acid is thereby prevented and no conversion to glutamine, either by enzymatic or by chemical catalysis, subsequently leading to pyroglutamic acid formation, is possible.
  c) Inhibitors of QC prevent in addition the formation pyroglutamic acid from any residual modified Aβ3-40/42 molecules and those modified Aβ3-40/42 molecules, which are generated by mutations of the APP gene.

Within the present invention, a similar combined action of DP IV or DP IV-like enzymes and QC was demonstrated for further peptide hormones, such as glucagon, CC chemokines and substance P.

Glucagon is a 29-amino acid polypeptide released from pancreatic islet alpha-cells that acts to maintain euglycemia by stimulating hepatic glycogenolysis and gluconeogenesis. Despite its importance, there remains controversy about the mechanisms responsible for glucagon clearance in the body. Pospisilik et al. assessed the enzymatic metabolism of glucagon using sensitive mass spectrometric techniques to identify the molecular products. Incubation of glucagon with purified porcine dipeptidyl peptidase IV (DP IV) yielded sequential production of glucagon3-29 and glucagon5-29. In human serum, degradation to glucagon3-29 was rapidly followed by N-terminal cyclization of glucagon, preventing further DP IV-mediated hydrolysis. Bioassay of glucagon, following incubation with purified DP IV or normal rat serum demonstrated a significant loss of hyperglycemic activity, while a similar incubation in DP IV-deficient rat serum did not show any loss of glucagon bioactivity. Degradation, monitored by mass spectrometry and bioassay, was blocked by the specific DP IV inhibitor, isoleucyl thiazolidine. These results identify DP IV as a primary enzyme involved in the degradation and inactivation of glucagon. These findings have important implications for the determination of glucagon levels in human plasma (Pospisilik et al., *Regul Pept* 2001 Jan. 12; 96(3):133-41).

Human Monocyte Chemotactic Protein (MCP)-2 has originally been isolated from stimulated osteosarcoma cells as a chemokine coproduced with MCP-1 and MCP-3. Von Coillie et al. (Van Coillie, E. et al. 1998 *Biochemistry* 37, 12672-12680) cloned a 5'-end extended MCP-2 cDNA from a human testis cDNA library. It encoded a 76 residue MCP-2 protein, but differed from the reported bone marrow-derived MCP-2 cDNA sequence in codon 46, which coded for a Lys instead of a Gln. This MCP-2Lys46 variant, caused by a single nucleotide polymorphism (SNP), was biologically compared with MCP-2Gln46. The coding regions were sub-cloned into the bacterial expression vector pHEN1, and after transformation of *Escherichia coli*, the two MCP-2 protein variants were recovered from the periplasm. Edman degradation revealed a Gln residue at the NH2 terminus instead of a pGlu. rMCP-2Gln46 and rMCP-2Lys46 and the NH$^2$-terminal cyclic counterparts were tested on monocytic cells in calcium mobilization and chemotaxis assays. No significant difference in biological activity was observed between the rMCP-2Gln46 and rMCP-2Lys46 isoforms. However, for both MCP-2 variants the NH$^2$-terminal pyroglutamate 30 was shown to be essential for chemotaxis, but not for calcium mobilization. NH$^2$-terminal truncation of rMCP-2Lys46 by the serine protease CD26/dipeptidyl peptidase IV (CD26/DPP IV) resulted in the release of the NH$^2$-terminal Gln-Pro dipeptide, whereas synthetic MCP-2 with an amino-terminal pGlu remained unaffected. CD26/DPP IV-clipped rMCP-2Lys46(3-76) was almost completely inactive in both chemotaxis and signaling assays. These observations indicated that the NH2-terminal pGlu in MCP-2 is necessary for chemotactic activity but also that it protects the protein against degradation by CD26/DPP IV (van Coillie, E. et al. *Biochemistry* 1998 37, 12672-80).

Within the present invention, it was determined by LC/MS-analysis that the formation of the N-terminal pyroglutamate residue determined in glucagon3-29 (Pospisilik et al., 2001), and in MCP-2 isoforms (van Coillie et al., 1998), is catalyzed by QC.

In addition, it was proven by LC/MS-investigation that after N-terminal DP IV-catalyzed removal of the two dipeptides Lys-Pro and Arg-Pro from substance P the remaining [Gln$^5$]substanceP5-11 is transformed by QC to [pGlu$^5$]substanceP5-11.

DP IV inhibitors are disclosed in WO 99/61431. In particular, DP IV inhibitors are disclosed comprising an amino acid residue and a thiazolidine or pyrrolidine group, and salts thereof, especially L-threo-isoleucyl thiazolidine, L-allo-isoleucyl thiazolidine, L-threo-isoleucyl pyrrolidine, L-allo-isoleucyl thiazolidine, L-allo-isoleucyl pyrrolidine, and salts thereof.

Further examples of low molecular weight dipeptidyl peptidase IV inhibitors are agents such as tetrahydroisoquinolin-3-carboxamide derivatives, N-substituted 2-cyanopyroles and -pyrrolidines, N—(N'-substituted glycyl)-2-cyanopyrrolidines, N-(substituted glycyl)-thiazolidines, N-(substituted glycyl)-4-cyanothiazolidines, amino-acyl-borono-prolyl-inhibitors, cyclopropyl-fused pyrrolidines and heterocyclic compounds. Inhibitors of dipeptidyl peptidase IV are described in U.S. Pat. No. 6,380,398, U.S. Pat. No. 6,011,155; U.S. Pat. No. 6,107,317; U.S. Pat. No. 6,110,949; U.S. Pat. No. 6,124,305; U.S. Pat. No. 6,172,081; WO 95/15309, WO 99/61431, WO 99/67278, WO 99/67279, DE 198 34 591, WO 97/40832, DE 196 16 486 C 2, WO 98/19998, WO 00/07617, WO 99/38501, WO 99/46272, WO 99/38501, WO 01/68603, WO 01/40180, WO 01/81337, WO 01/81304, WO 01/55105, WO 02/02560 and WO 02/14271, WO 02/04610, WO 02/051836, WO 02/068420, WO 02/076450; WO 02/083128, WO 02/38541, WO 03/000180, WO 03/000181, WO 03/000250, WO 03/002530, WO 03/002531, WO 03/002553, WO 03/002593, WO 03/004496, WO 03/024942 and WO 03/024965, the teachings of which are herein incorporated by reference in their entirety, especially concerning these inhibitors, their definition, uses and their production.

Preferred for the use in combination with effectors of QC are DPIV inhibitors such as NVP DPP728A (1-[[[2-[{5-cyanopyridin-2-yl}amino]ethyl]amino]acetyl]-2-cyano-(S)-pyrrolidine) (Novartis) as disclosed by Hughes et al. 1999 *Biochemistry* 38 11597-11603, LAF-237 (1-[(3-hydroxyadamant-1-ylamino)-acetyl]-pyrrolidine-2(S)-carbonitrile); disclosed by Hughes et al., Meeting of the American Diabetes Association 2002, Abstract no. 272 (Novartis), TSL-225 (tryptophyl-1,2,3,4-tetrahydroisoquinoline-3-carboxylic acid), disclosed by Yamada et al. 1998 *Bioorg Med Chem Lett* 8, 1537-1540, 2-cyanopyrrolidides and 4-cyanopyrrolidides as disclosed by Asworth et al. 1996 *Bioorg Med Chem Lett* 6, 1163-1166 and 2745-2748, FE-999011, disclosed by Sudre et al. 2002 *Diabetes* 51, 1461-1469 (Ferring) and the compounds disclosed in WO 01/34594 (Guilford), employing dosages as set out in the above references.

More preferred DP IV inhibitors for the use in combination with effectors of QC are dipeptide compounds in which the amino acid is preferably selected from a natural amino acid, such as, for example, leucine, valine, glutamine, glutamic acid, proline, isoleucine, asparagines and aspartic acid. The dipeptide-like compounds used according to the invention exhibit at a concentration (of dipeptide compounds) of 10 µM, a reduction in the activity of plasma dipeptidyl peptidase IV or DPIV-analogous enzyme activities of at least 10%, especially of at least 40%. Frequently a reduction in activity of at least 60% or at least 70% is also desired in vivo. Preferred compounds may also exhibit a reduction in activity of a maximum of 20% or 30%.

Preferred dipeptide compounds are N-valyl prolyl, O-benzoyl hydroxylamine, alanyl pyrrolidine, isoleucyl thiazolidine like L-allo-isoleucyl thiazolidine, L-threo-isoleucyl pyrrolidine and salts thereof, especially the fumaric salts, and L-allo-isoleucyl pyrrolidine and salts thereof. Especially preferred compounds are glutaminyl pyrrolidine and glutaminyl thiazolidine, H-Asn-pyrrolidine, H-Asn-thiazolidine, H-Asp-pyrrolidine, H-Asp-thiazolidine, H-Asp(NHOH) pyrrolidine, H-Asp(NHOH)-thiazolidine, H-Glu-pyrrolidine, H-Glu-thiazolidine, H-Glu(NHOH)-pyrrolidine, H-Glu(NHOH)-thiazolidine, H-His-pyrrolidine, H-His-thiazolidine, H-Pro-pyrrolidine, H-Pro-thiazolidine, H-Ile-azididine, H-Ile-pyrrolidine, H-L-allo-Ile-thiazolidine, H-Val-pyrrolidine and H-Val-thiazolidine and pharmaceutically acceptable salts thereof. These compounds are described in WO 99161431 and EP 1 304 327.

Furthermore, the present invention provides for the use of effectors of QC in combination with substrate-like peptide compounds useful for competitive modulation of dipeptidyl peptidase IV catalysis. Preferred peptide compounds are 2-Amino octanoic acid-Pro-Ile, Abu-Pro-Ile, Aib-Pro-Ile, Aze-Pro-Ile, Cha-Pro-Ile, Ile-Hyp-Ile, Ile-Pro-allo-Ile, Ile-Pro-t-butyl-Gly, Ile-Pro-Val, Nle-Pro-Ile, Nva-Pro-Ile, Orn-Pro-Ile, Phe-Pro-Ile, Phg-Pro-Ile, Pip-Pro-Ile, Ser(Bzl)-Pro-Ile, Ser(P)-Pro-Ile, Ser-Pro-Ile, t-butyl-Gly-Pro-D-Val, t-butyl-Gly-Pro-Gly, t-butyl-Gly-Pro-Ile, t-butyl-Gly-Pro-Ile-amide, t-butyl-Gly-Pro-t-butyl-Gly, t-butyl-Gly-Pro-Val, Thr-Pro-Ile, Tic-Pro-Ile, Trp-Pro-Ile, Tyr(P)-Pro-Ile, Tyr-Pro-allo-Ile, Val-Pro-allo-Ile, Val-Pro-t-butyl-Gly, Val-Pro-Val and pharmaceutically acceptable salts thereof, wherein t-butyl-Gly is defined as

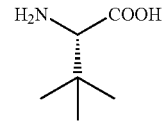

and Ser(Bzl) and Ser(P) are defined as benzyl-serine and phosphoryl-serine, respectively. Tyr(P) is defined as phosphoryl-tyrosine. These compounds are disclosed in WO 03/002593.

Further preferred DP IV-inhibitors, which can be used according to the present invention in combination with effectors of QC, are peptidylketones, e.g.
2-Methylcarbonyl-1-N-[(L)-Alanyl-(L)-Valinyl]-(2S)-pyrrolidine hydrobromide, 2-Methyl)carbonyl-1-N-[(L)-Valinyl-(L)-Prolyl-(L)-Valinyl]-(2S)-pyrrolidine hydrobromide,
2-[(Acetyl-oxy-methyl)carbonyl]-1-N-[(L)-Alanyl-(L)-Valinyl]-(2S)-pyrrolidine hydrobromide,
2-[Benzoyl-oxy-methyl)carbonyl]-1-N-[{(L)-Alanyl}-(L)-Valinyl]-(2S)-pyrrolidine hydrobromide,
2-{[(2,6-Dichlorbenzyl)thiomethyl]carbonyl}-1-N-[{(L)-Alanyl}-(L)-Valinyl]-(2S)-pyrrolidine,
2-[Benzoy-loxy-methyl)carbonyl]-1-N-[Glycyl-(L)-Valinyl]-(2S)-pyrrolidine hydrobromide,
2-[([1,3]-Thiazolethiazol-2-yl)carbonyl]-1-N-[{(L)-Alanyl}-(L)-Valinyl]-(2S)-pyrrolidine trifluoracetate,
2-[(Benzothiazolethiazol-2-yl)carbonyl]-1-N—[N-{(L)-Alanyl}-(L)-Valinyl]-(2S)-pyrrolidin trifluoracetate,
2-[(-Benzothiazolethiazol-2-yl)carbonyl]-1-N-[{(L)-Alanyl}-Glycyl]-(2S)-pyrrolidine trifluoracetate,
2-[(Pyridin-2-yl)carbonyl]-1-N—[N-{(L)-Alanyl}-(L)-Valinyl]-(2S)-pyrrolidine trifluoracetate
and other pharmaceutically acceptable salts thereof. These compounds are disclosed in WO 03/033524.

Further, according to the present invention substituted aminoketones can be used in combination with effectors of QC. Preferred substituted aminoketones are
1-cyclopentyl-3-methyl-1-oxo-2-pentanaminium chloride,
1-cyclopent-3-methyl-1-oxo-2-butanaminium chloride,
1-cyclopentyl-3,3-dimethyl-1-oxo-2-butanaminium chloride,
1-cyclohexyl-3,3-dimethyl-1-oxo-2-butanaminium chloride, 3-(cyclopentylcarbonyl)-1,2,3,4-tetrahydroisoquinolinium chloride,
N-(2-cyclopentyl-2-oxoethyl)cyclohexanaminium chloride
and other pharmaceutically acceptable salts thereof.

Among the rare group of proline-specific proteases, DP IV was originally believed to be the only membrane-bound enzyme specific for proline as the penultimate residue at the amino-terminus of the polypeptide chain. However, other molecules, even those structurally non-homologous with the DP IV but bearing corresponding enzyme activity, have been identified. DP IV-like enzymes, which have been identified so far, include e.g. fibroblast activation protein α, dipeptidyl peptidase IV β, dipeptidyl aminopeptidase-like protein, N-acetylated α-linked acidic dipeptidase, quiescent cell proline dipeptidase, dipeptidyl peptidase II, attractin and dipeptidyl peptidase IV related protein (DPP 8), DPL1 (DPX, DP6), DPL2 and DPP 9 described in review articles by Sedo & Malik (Sedo and Malik 2001, Biochim Biophys Acta, 36506, 1-10) and Abbott and Gorrell (Abbott, C. A. and Gorrell, M. D. 2002 In: Langner & Ansorge (ed.), Ectopeptidases. Kluwer Academic/Plenum Publishers, New York, 171-195). Recently, the cloning and characterization of dipeptidyl peptidase 10 (DPP 10) was reported (Qi, S.Y. et al., Biochemical Journal Immediate Publication. Published on 28 Mar. 2003 as manuscript BJ20021914).

Effectors, as that term is used herein, are defined as molecules that bind to enzymes and increase or decrease their activity in vitro and/or in vivo. Some enzymes have binding sites for small molecules that affect their catalytic activity; a stimulator molecule is called an activator. Enzymes may even have multiple sites for recognizing more than one activator or inhibitor. Enzymes can detect concentrations of a variety of molecules and use that information to vary their own activities.

Effectors can modulate enzymatic activity because enzymes can assume both active and inactive conformations: activators are positive effectors, inhibitors are negative effectors. Effectors act only at the active sites of enzymes, but also at regulatory sites, or allosteric sites, terms used to emphasize that the regulatory site is an element of the enzyme distinct from the catalytic site and to differentiate this form of regulation from competition between substrates and inhibitors at the catalytic site (Darnell, J., Lodish, H. and Baltimore, D. 1990, Molecular Cell Biology 2$^{nd}$ Edition, Scientific American Books, New York, page 63).

In the peptides of the present invention, each amino acid residue is represented by a one-letter or a three-letter designation, corresponding to the trivial name of the amino acid, in accordance with the following conventional list:

| Amino Acid | One-Letter Symbol | Three-Letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The term "QC" as used herein comprises glutaminyl cyclase (QC) and QC-like enzymes. QC and QC-like enzymes have identical or similar enzymatic activity, further defined as QC activity. In this regard, QC-like enzymes can fundamentally differ in their molecular structure from QC.

The term "QC activity" as used herein is defined as intramolecular cyclization of N-terminal glutamine residues into pyroglutamic acid (pGlu*) or of N-terminal L-homoglutamine or L-β homoglutamine to a cyclic pyro-homoglutamine derivative under liberation of ammonia. See therefore schemes 1 and 2.

Scheme 1: Cyclization of glutamine by QC

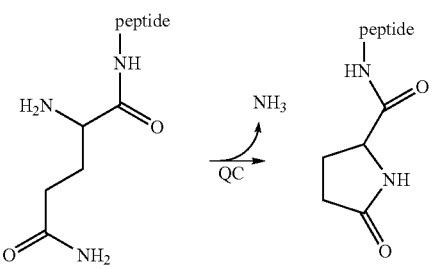

Scheme 2: Cyclization of L-homoglutamine by QC

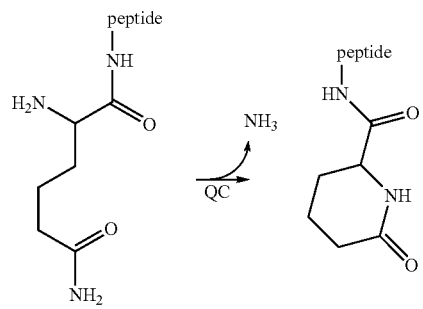

The term "EC" as used herein comprises the side activity of QC and QC-like enzymes as cyclase (EC), further defined as EC activity.

The term "EC activity" as used herein is defined as intramolecular cyclization of N-terminal glutamate residues into pyroglutamic acid (pGlu*) by QC. See therefore scheme 3.

The term "metal-dependent enzyme" as used herein is defined as enzyme(s) that require a bound metal ion in order to fulfill their catalytic function and/or require a bound metal ion in order to form the catalytically active structure.

Molecules that bind to enzymes and increase or decrease their activities are called "effectors". Effectors can modify enzymatic activity because enzymes can assume both active and inactive conformations: activators are positive effectors; inhibitors are negative effectors. Effectors bind at regulatory sites, or allosteric sites (from the Greek for "another shape"), a term used to emphasize that the regulatory site is an element of the enzyme distinct from the catalytic site and to differentiate this form of regulation from competition between substrates and inhibitors at the catalytic site.

According to the individual embodiments of the present invention, either activators or inhibitors are preferred.

Scheme 3: N-terminal cyclization of uncharged glutamyl peptides by QC (EC)

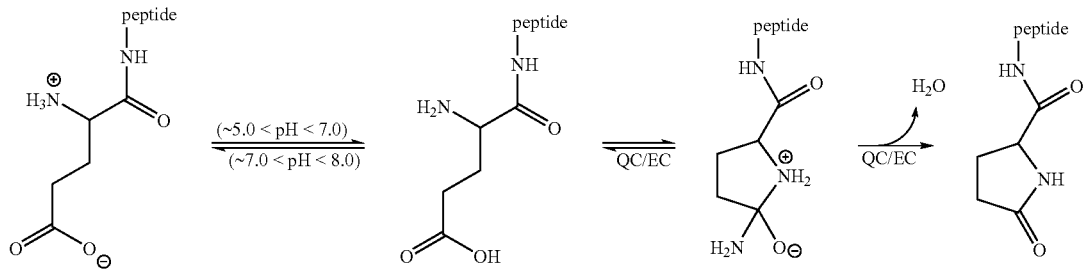

Another aspect of the present invention is the identification of new physiological substrates of QC. These were identified by performing cyclization experiments with mammalian peptides as described in example 5. Prior, human QC and papaya QC were isolated as described in example 1. The applied methods are described in example 2, and the peptide synthesis employed is outlined in example 6. The results of the study are shown in Table 1.

TABLE 1

New physiological substrates of glutaminyl cyclase

| | Human QC | | | Papaya QC | | |
|---|---|---|---|---|---|---|
| Substrate | $K_M$ (μM) | $k_{cat}$ (s$^{-1}$) | $k_{cat}$/KM (mM$^{-1}$s$^{-1}$) | $K_M$ (μM) | $k_{cat}$ (s-1) | $k_{cat}$/$K_M$ (mM$^{-1}$s$^{-1}$) |
| [Gln$^1$]-Gastrin | 31 ± 1 | 54.1 ± 0.6 | 1745.2 ± 36.9 | 34 ± 2 | 25.8 ± 0.5 | 759 ± 30 |
| [Gln$^1$]-Neurotensin | 31 ± 1 | 48.8 ± 0.4 | 1318.9 ± 24.8 | 40 ± 3 | 35.7 ± 0.9 | 893 ± 44 |
| [Gln$^1$]-FPP | 87 ± 2 | 69.6 ± 0.3 | 800.0 ± 14.9 | 232 ± 9 | 32.5 ± 0.4 | 140 ± 4 |
| [Gln$^1$]-TRH | 90 ± 4 | 82.8 ± 1.2 | 920.0 ± 27.6 | n.d. | n.d. | n.d. |
| [Gln$^1$]-GnRH | 53 ± 3 | 69.2 ± 1.1 | 1305.7 ± 53.2 | 169 ± 9 | 82.5 ± 1.9 | 488.2 ± 14.8 |
| [Gln$^3$]-glucagon(3-29) | | | * | | | * |
| [Gln$^5$]-substance P(5-11) | | | * | | | * |

(*, determined qualitatively by MALDI-TOF experiments)

All analyses were performed in the optimal range of activity and stability of either human or plant QC, as demonstrated in example 4.

The amino acid sequences of physiological active peptides having an N-terminal glutamine residue and being therefore substrates for the QC enzyme are listed in Table 2:

TABLE 2

Amino acid sequences of physiological active peptides with an N-terminal glutamine residue

| Peptide | Amino acid sequence | Function |
|---|---|---|
| Gastrin 17 Swiss-Prot: P01350 | QGPWL EEEEEAYGWM DF (amide) (SEQ ID NO: 3) | Gastrin stimulates the stomach mucosa to produce and secrete hydrochloric acid and the pancreas to secrete its digestive enzymes. It also stimulates smooth muscle contraction and increases blood circulation and water secretion in the stomach and intestine. |
| Neurotensin Swiss-Prot: P30990 | QLYENKPRRP YIL (SEQ ID NO: 4) | Neurotensin plays an endocrine or paracrine role in the regulation of fat metabolism. It causes contraction of smooth muscle. |
| FPP | QEP amide | A tripeptide related to thyrotrophin releasing hormone (TRH), is found in seminal plasma. Recent evidence obtained in vitro and in vivo showed that FPP plays an important role in regulating sperm fertility. |

TABLE 2-continued

Amino acid sequences of physiological active peptides with an N-terminal glutamine residue

| Peptide | Amino acid sequence | Function |
|---|---|---|
| TRH<br>Swiss-Prot:<br>P20396 | QHP amide | TRH functions as a regulator of the biosynthesis of TSH in the anterior pituitary gland and as a neurotransmitter/neuromodulator in the central and peripheral nervous systems. |
| GnRH<br>Swiss-Prot:<br>P01148 | QHWSYGL RP(G) amide<br>(SEQ ID NO: 5) | Stimulates the secretion of gonadotropins; it stimulates the secretion of both luteinizing and follicle-stimulating hormones. |
| CCL16<br>(small inducible cytokine A16)<br>Swiss-Prot:<br>O15467 | QPKVPEW VNTPSTCCLK YYEKVLPRRL VVGYRKALNC HLPAIIFVTK RNREVCTNPN DDWVQEYIKD PNLPLLPTRN LSTVKIITAK NGQPQLLNSQ<br>(SEQ ID NO: 6) | Shows chemotactic activity for lymphocytes and monocytes but not neutrophils. Also shows potent myelosuppressive activity, suppresses proliferation of myeloid progenitor cells. Recombinant SCYA16 shows chemotactic activity for monocytes and THP-1 monocytes, but not for resting lymphocytes and neutrophils. Induces a calcium flux in THP-1 cells that were desensitized by prior expression to RANTES. |
| CCL8 (small inducible cytokine A8)<br>Swiss-Prot:<br>P80075 | QPDSVSI PITCCFNVIN RKIPIQRIES YTRITNIQCP KEAVIFKTKR GKEVCADPKE RWVRDSMKHL DQIFQNLKP<br>(SEQ ID NO: 7) | Chemotactic factor that attracts monocytes, lymphocytes, basophils and eosinophils. May play a role in neoplasia and inflammatory host responses. This protein can bind heparin. |
| CCL2 (small inducible cytokine A2)<br>Swiss-Prot:<br>P13500 | QPDAINA PVTCCYNFTN RKISVQRLAS YRRITSSKCP KEAVIFKTIV AKEICADPKQ KWVQDSMDHL DKQTQTPKT<br>(SEQ ID NO: 8) | Chemotactic factor that attracts monocytes and basophils but not neutrophils or eosinophils. Augments monocyte anti-tumor activity. Has been implicated in the pathogenesis of diseases characterized by monocytic infiltrates, like psoriasis, rheumatoid arthritis or atherosclerosis. May be involved in the recruitment of monocytes into the arterial wall during the disease process of atherosclerosis. Binds to CCR2 and CCR4. |
| CCL18<br>(small inducible cytokine A18)<br>Swiss-Prot:<br>P55774 | QVGTNKELC CLVYTSWQIP QKFIVDYSET SPQCPKPGVI LLTKRGRQIC ADPNKKWVQK YISDLKLNA<br>(SEQ ID NO: 9) | Chemotactic factor that attracts lymphocytes but not monocytes or granulocytes. May be involved in B cell migration into B cell follicles in lymph nodes. Attracts naive T lymphocytes toward dendritic cells and activated macrophages in lymph nodes, has chemotactic activity for naive T cells, CD4+ and CD8+ T cells and thus may play a role in both humoral and cell-mediated immunity responses. |
| Fractalkine (neurotactin)<br>Swiss-Prot:<br>P78423 | QHHGVT KCNITCSKMT SKIPVALLIH YQQNQASCGK RAIILETRQH RLFCADPKEQ WVKDAMQHLD RQAAALTRNG GTFEKQIGEV KPRTTPAAGG MDESVVLEPE ATGESSSLEP TPSSQEAQRA LGTSPELPTG VTGSSGTRLP PTPKAQDGGP VGTELFRVPP VSTAATWQSS APHQPGPSLW AEAKTSEAPS TQDPSTQAST ASSPAPEENA PSEGQRVWGQ GQSPRPENSL EREEMGPVPA HTDAFQDWGP GSMAHVSVVP VSSEGTPSRE PVASGSWTPK AEEPIHATMD PQRLGVLITP VPDAQAATRR QAVGLLAFLG LLFCLGVAMF TYQSLQGCPR KMAGEMAEGL RYIPRSCGSN SYVLVPV<br>(SEQ ID NO: 10) | The soluble form is chemotactic for T cells and monocytes, but not for neutrophils. The membrane-bound form promotes adhesion of those leukocytes to endothelial cells. May play a role in regulating leukocyte adhesion and migration processes at the endothelium. Binds to cx3cr1. |
| CCL7 (small inducible cytokine A7)<br>Swiss-Prot:<br>P80098 | QPVGINT STTCCYRFIN KKIPKQRLES YRRTTSSHCP REAVIFKTKL DKEICADPTQ KWVQDFMKHL DKKTQTPKL<br>(SEQ ID NO: 11) | Chemotactic factor that attracts monocytes and eosinophils, but not neutrophils. Augments monocyte anti-tumor activity. Also induces the release of gelatinase B. This protein can bind heparin. Binds to CCR1, CCR2 and CCR3. |

TABLE 2-continued

Amino acid sequences of physiological active peptides with an N-terminal glutamine residue

| Peptide | Amino acid sequence | Function |
|---|---|---|
| Orexin A (Hypocretin-1) Swiss-Prot 043612 | QPLPDCCRQK TCSCRLYELL HGAGNHAAGI LTL (SEQ ID NO: 12) | Neuropeptide that plays a significant role in the regulation of food intake and sleep wakefulness, possibly by coordinating the complex behavioral and physiologic responses of these complementary homeostatic functions. It plays also a broader role in the homeostatic regulation of energy metabolism, autonomic function, hormonal balance and the regulation of body fluids. Orexin-A binds to both OX1R and OX2R with a high 7affinity. |
| Substance P | RPK PQQFFGLM (SEQ ID NO: 13) | Belongs to the tachykinins. Tachykinins are active peptides which excite neurons, evoke behavioral responses, are potent vasodilators and secretagogues, and contract (directly or indirectly) many smooth muscles. |

In a fourth embodiment, the peptides [Gln$^1$]Gastrin (17 and 34 amino acids in length), [Gln$^1$]Neurotensin and [Gln$^1$]FPP were identified as new physiological substrates of QC. Gastrin, Neurotensin and FPP comprise a pGlu residue in their N-terminal position. This N terminal pGlu residue was shown to be formed from N-terminal glutamine by QC catalysis for all peptides. As a result, these peptides are activated in terms of their biological function upon conversion of the N-terminal glutamine residue to pGlu.

Transepithelial transducing cells, particularly the gastrin (G) cell, co-ordinate gastric acid secretion with the arrival of food in the stomach. Recent work showed that multiple active products are generated from the gastrin precursor, and that there are multiple control points in gastrin biosynthesis. Biosynthetic precursors and intermediates (progastrin and Gly-gastrins) are putative growth factors; their products, the amidated gastrins, regulate epithelial cell proliferation, the differentiation of acid-producing parietal cells and histamine-secreting enterochromaffin-like (ECL) cells, and the expression of genes associated with histamine synthesis and storage in ECL cells, as well as acutely stimulating acid secretion. Gastrin also stimulates the production of members of the epidermal growth factor (EGF) family, which in turn inhibit parietal cell function but stimulate the growth of surface epithelial cells. Plasma gastrin concentrations are elevated in subjects with *Helicobacter pylori*, who are known to have increased risk of duodenal ulcer disease and gastric cancer (Dockray, G. J. 1999 *J Physiol* 15 315-324).

The peptide hormone gastrin, released from antral G cells, is known to stimulate the synthesis and release of histamine from ECL cells in the oxyntic mucosa via CCK-2 receptors. The mobilized histamine induces acid secretion by binding to the H(2) receptors located on parietal cells. Recent studies suggest that gastrin, in both its fully amidated and less processed forms (progastrin and glycine-extended gastrin), is also a growth factor for the gastrointestinal tract. It has been established that the major trophic effect of amidated gastrin is for the oxyntic mucosa of stomach, where it causes increased proliferation of gastric stem cells and ECL cells, resulting in increased parietal and ECL cell mass. On the other hand, the major trophic target of the less processed gastrin (e.g. glycine-extended gastrin) appears to be the colonic mucosa (Koh, T. J. and Chen, D. 2000 *Regul Pept* 9337-44).

In a fifth embodiment, the present invention provides the use of activity increasing effectors of QC for the stimulation of gastrointestinal tract cell proliferation, especially gastric mucosal cell proliferation, epithelial cell proliferation, the differentiation of acid-producing parietal cells and histamine-secreting enterochromaffin-like (ECL) cells, and the expression of genes associated with histamine synthesis and storage in ECL cells, as well as for the stimulation of acute acid secretion in mammals by maintaining or increasing the concentration of active [pGlu$^1$]-Gastrin.

In a sixth embodiment, the present invention provides the use of activity decreasing effectors of QC for the treatment of duodenal ulcer disease and gastric cancer with or w/o *Heliobacter pylori* in mammals by decreasing the conversion rate of inactive [Gln$^1$]Gastrin to active [pGlu$^1$]Gastrin. Neurotensin (NT) is a neuropeptide implicated in the pathophysiology of schizophrenia that specifically modulates neurotransmitter systems previously demonstrated to be misregulated in this disorder. Clinical studies in which cerebrospinal fluid (CSF) NT concentrations have been measured revealed a subset of schizophrenic patients with decreased CSF NT concentrations that are restored by effective antipsychotic drug treatment. Considerable evidence also exists concordant with the involvement of NT systems in the mechanism of action of antipsychotic drugs. The behavioral and biochemical effects of centrally administered NT remarkably resemble those of systemically administered antipsychotic drugs, and antipsychotic drugs increase NT neurotransmission. This concatenation of findings led to the hypothesis that NT functions as an endogenous antipsychotic. Moreover, typical and atypical antipsychotic drugs differentially alter NT neurotransmission in nigrostriatal and mesolimbic dopamine terminal regions, and these effects are predictive of side effect liability and efficacy, respectively (Binder, E. B. et al. 2001 *Biol Psychiatry* 50 856-872).

In a seventh embodiment, the present invention provides the use of activity increasing effectors of QC for the preparation of antipsychotic drugs and/or for the treatment of schizophrenia in mammals. The effectors of QC either maintain or increase the concentration of active [pGlu$^1$]neurotensin.

Fertilization promoting peptide (FPP), a tripeptide related to thyrotrophin releasing hormone (TRH), is found in seminal plasma. Recent evidence obtained in vitro and in vivo showed that FPP plays an important role in regulating sperm fertility. Specifically, FPP initially stimulates nonfertilizing (uncapacitated) spermatozoa to "switch on" and become fertile more quickly, but then arrests capacitation so that spermatozoa do not undergo spontaneous acrosome loss and therefore do not lose fertilizing potential. These responses are mimicked, and indeed augmented, by adenosine, known to regulate the adenylyl cyclase (AC)/cAMP signal transduction pathway. Both FPP and adenosine have been shown to stimulate cAMP production in uncapacitated cells but inhibit it in capacitated cells, with FPP receptors somehow interacting with adenosine receptors and G proteins to achieve regulation of AC. These events affect the tyrosine phosphorylation state of various proteins, some being important in the initial "switching on," others possibly being involved in the acrosome reaction itself. Calcitonin and angiotensin II, also found in seminal plasma, have similar effects in vitro on uncapacitated spermatozoa and can augment responses to FPP. These molecules have similar effects in vivo, affecting fertility by stimulating and then maintaining fertilizing potential. Either reductions in the availability of FPP, adenosine, calcitonin, and angiotensin II or defects in their receptors contribute to male infertility (Fraser, L. R. and Adeoya-Osiguwa, S. A. 2001 Vitam Horm 63, 1-28).

In an eight embodiment, the present invention provides the use of activity lowering effectors of QC for the preparation of fertilization prohibitive drugs and/or to reduce the fertility in mammals. The activity lowering effectors of QC decrease the concentration of active [pGlu$^1$]FPP, leading to a prevention of sperm capacitation and deactivation of sperm cells. In contrast it could be shown that activity increasing effectors of QC are able to stimulate fertility in males and to treat infertility.

In a ninth embodiment, further physiological substrates of QC were identified within the present invention. These are [Gln$^1$]CCL2, [Gln$^1$]CCL7, [Gln$^1$]CCL8, [Gln$^1$]CCL16, [Gln$^1$]CCL18 and [Gln$^1$]fractalkine. For details see Table 2. These polypeptides play an important role in pathophysiological conditions, such as suppression of proliferation of myeloid progenitor cells, neoplasia, inflammatory host responses, cancer, psoriasis, rheumatoid arthritis, atherosclerosis, humoral and cell-mediated immunity responses, leukocyte adhesion and migration processes at the endothelium.

Several cytotoxic T lymphocyte peptide-based vaccines against hepatitis B, human immunodeficiency virus and melanoma were recently studied in clinical trials. One interesting melanoma vaccine candidate alone or in combination with other tumor antigens, is the decapeptide ELA. This peptide is a Melan-A/MART-1 antigen immunodominant peptide analog, with an N-terminal glutamic acid. It has been reported that the amino group and gamma-carboxylic group of glutamic acids, as well as the amino group and gamma-carboxamide group of glutamines, condense easily to form pyroglutamic derivatives. To overcome this stability problem, several peptides of pharmaceutical interest have been developed with a pyroglutamic acid instead of N-terminal glutamine or glutamic acid, without loss of pharmacological properties. Unfortunately compared with ELA, the pyroglutamic acid derivative (PyrELA) and also the N-terminal acetyl-capped derivative (AcELA) failed to elicit cytotoxic T lymphocyte (CTL) activity. Despite the apparent minor modifications introduced in PyrELA and AcELA, these two derivatives probably have lower affinity than ELA for the specific class I major histocompatibility complex. Consequently, in order to conserve full activity of ELA, the formation of PyrELA must be avoided (Beck A. et al. 2001, J Pept Res 57(6):528-38.). Recently, it was found that also the enzyme glutaminyl cyclase (QC) is overexpressed in melanomas (Ross D. T et al., 2000, Nat Genet. 24:227-35.).

In a tenth embodiment, the present invention provides the use of effectors of QC for the preparation of a medicament for the treatment of pathophysiological conditions, such as suppression of proliferation of myeloid progenitor cells, neoplasia, inflammatory host responses, cancer, malign metastasis, melanoma, psoriasis, rheumatoid arthritis, atherosclerosis, impaired humoral and cell-mediated immunity responses, leukocyte adhesion and migration processes at the endothelium.

In an eleventh embodiment, [Gln$^1$]orexin A was identified as a physiological substrate of QC within the present invention. Orexin A is a neuropeptide that plays a significant role in the regulation of food intake and sleep-wakefulness, possibly by coordinating the complex behavioral and physiologic responses of these complementary homeostatic functions. It plays also a role in the homeostatic regulation of energy metabolism, autonomic function, hormonal balance and the regulation of body fluids.

In a twelfth embodiment, the present invention provides the use of effectors of QC for the preparation of a medicament for the treatment of impaired food intake and sleep-wakefulness, impaired homeostatic regulation of energy metabolism, impaired autonomic function, impaired hormonal balance and impaired regulation of body fluids.

Polyglutamine expansions in several proteins lead to neurodegenerative disorders, such as Parkinson disease and Kennedy's disease. The mechanism therefore remains largely unknown. The biochemical properties of polyglutamine repeats suggest one possible explanation: endolytic cleavage at a glutaminyl-glutaminyl bond followed by pyroglutamate formation may contribute to the pathogenesis through augmenting the catabolic stability, hydrophobicity, amyloidogenicity, and neurotoxicity of the polyglutaminyl proteins (Saido, T; Med Hypotheses (2000) March; 54(3):427-9). In a thirteenth embodiment, the present invention provides therefore the use of effectors of QC for the preparation of a medicament for the treatment of Parkinson disease and Huntington's disease.

In a fourteenth embodiment, the present invention provides a general way to reduce or inhibit the enzymatic activity of QC. Examples of inhibitory compounds are also provided.

Figure 19:
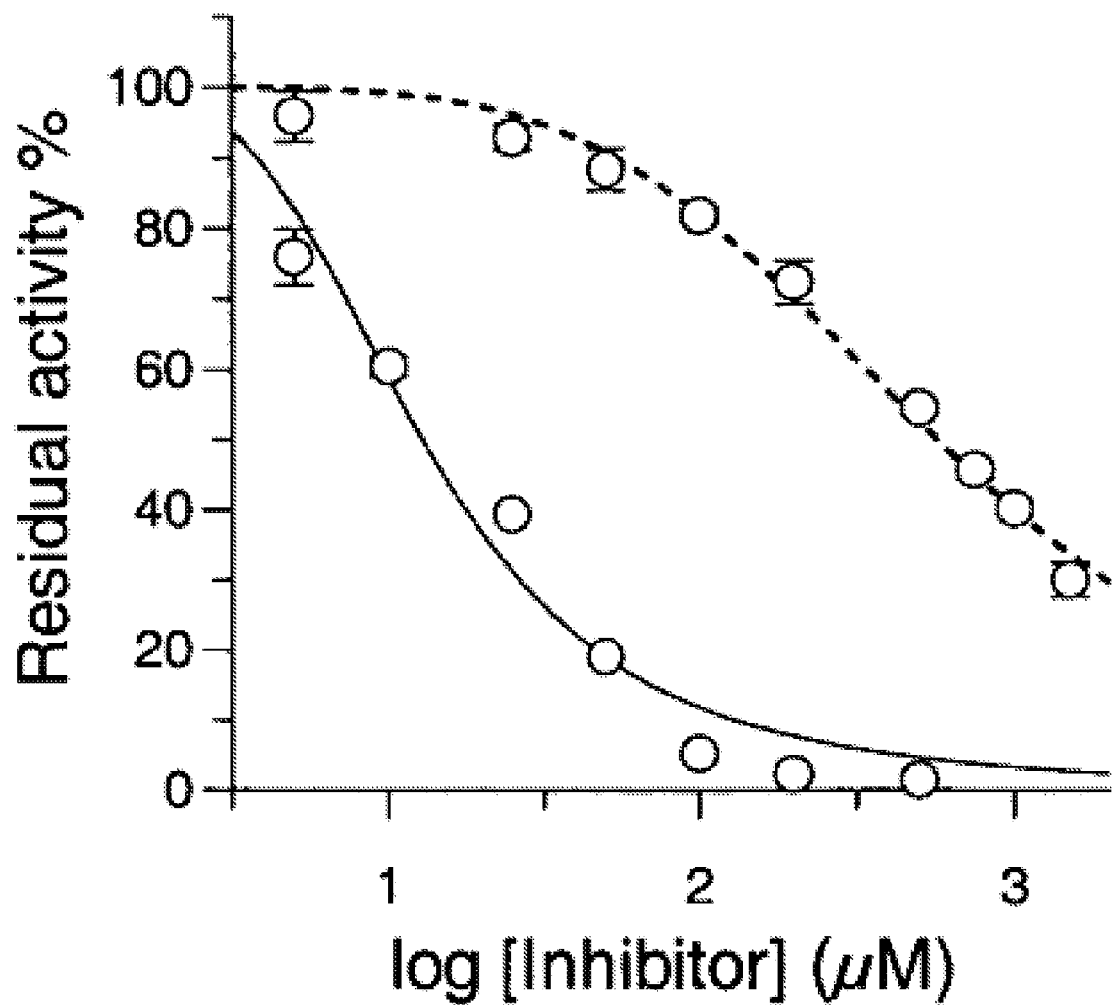
FIG. 19 shows the time-dependent inactivation of QC by the heterocyclic chelator 1,10-phenanthroline. After incubation of the QC-enzyme with the inhibitor in absence of substrate (continuous line), a reduced enzymatic activity was observed compared to samples that were not preincubated with inhibitor (dotted trace), indicating metal ion remove from the active site of QC.
Figure 20:
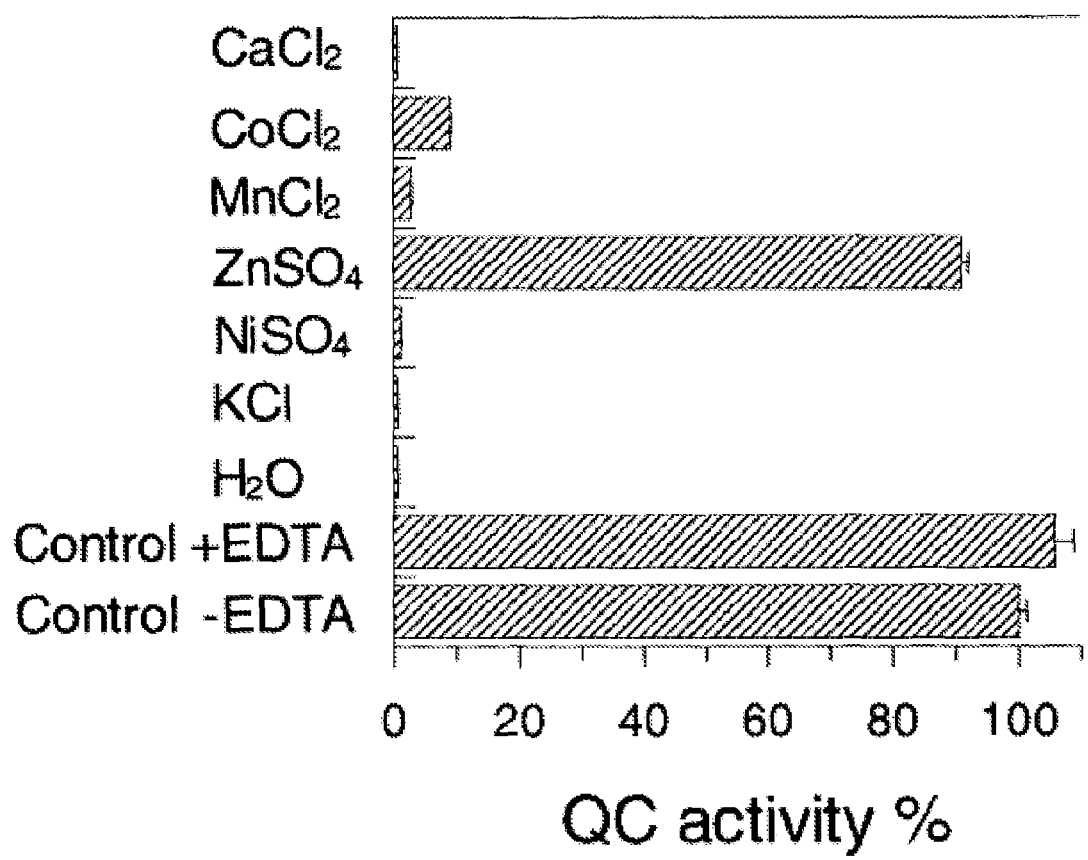
FIG. 20 shows the reactivation of human QC with monovalent- and divalent metal ions. QC was inactivated by addition of 2 mM dipicolinic acid in 50 mM Bis-Tris, pH 6.8. Subsequently, the enzyme was subjected to dialysis against 50 mM Bis-Tris, pH 6.8, containing 1.0 mM 30 EDTA. Reactivation of the enzymes was achieved by incubation of the inactivated enzyme sample with metal ions at a concentration of 0.5 mM, in presence of 0.5 mM EDTA in order to avoid an unspecific reactivation by traces of metal ions present in buffer solutions. Controls are given by enzyme samples that were not inactivated, but also dialyzed against EDTA solution as the inactivated enzyme (+EDTA) and enzyme samples that were dialyzed against buffer solutions without added EDTA (−EDTA).

Inhibition of a mammalian QC was only detected initially for 1,10-phenanthroline and reduced 6-methylpterin (Busby, W. H. J. et al. 1987 J Biol Chem 262, 8532-8536). EDTA did not inhibit QC, thus it was concluded that QC is not a metal-dependent enzyme (Busby, W. H. J. et al. 1987 J Biol Chem 262, 8532-8536, Bateman, R. C. J. et al. 2001 Biochemistry 40, 11246-11250, Booth, R. E. et al. 2004 BMC Biology 2). In the present invention, however, it is shown that human QC and other animal QCs are metal-dependent enzymes, as revealed by the inhibition characteristics of QC by 1,10-phenanthroline, dipicolinic acid, 8-hydroxy-quinoline and other chelators (FIGS. 18,19) and by the reactivation of QC by transition metal ions (FIG. 20). Finally, the metal dependence is outlined by a sequence comparison to other metal-dependent enzymes, showing a conservation of the chelating amino acid residues also in human QC (FIG. 21). The interaction of compounds with the active-site bound metal ion represents a general way to reduce or inhibit QC activity.

In the present invention it is shown that imidazole derivatives are potent inhibitors of QC. Using the continuous assay (for details see example 2), many imidazole derivatives were analyzed concerning their ability to inhibit the human QC as a member of the highly conserved mammalian QCs.

Thus, the present invention provides imidazole derivatives and histidine and its derivatives as activity reducing effectors of QC and their characteristics in terms of inhibition type and potency. Structures and Ki-values are shown in tables 3 and 4. The results are described in detail in example 7.

TABLE 3

Inhibitory constants of imidazole derivatives in the human QC catalyzed reaction. Determinations were performed at 30° C. in 0.05 M Tris-HCl pH 8.0, containing 5 mM EDTA.

| Compound | Ki-value (mM) | Structure |
| --- | --- | --- |
| core structures | | |
| imidazole | 0.103 ± 0.004 | |
| benzimidazole | 0.138 ± 0.005 | |
| N-1 derivatives | | |
| 1-benzylimidazole | 0.0071 ± 0.0003 | |
| 1-methylimidazole | 0.030 ± 0.001 | |
| 1-vinylimidazole | 0.049 ± 0.002 | |
| oxalic acid diimidazolidide | 0.078 ± 0.002 | |
| N-acetylimidazole | 0.107 ± 0.003 | |
| N-(trimethylsilyl)-imidazole | 0.167 ± 0.007 | |
| N-benzoylimidazole | 0.174 ± 0.007 | |
| 1-(2-oxo-2-phenyl-ethyl)-imidazole | 0.184 ± 0.005 | |
| 1-(3-aminopropyl)-imidazole | 0.41 ± 0.01 | |
| 1-phenylimidazole | no inhibition | |
| 1,1'-sulfonyldiimidazole | no inhibition | |
| C-4(5) derivatives | | |
| N-omega-acetylhistamine | 0.017 ± 0.001 | |
| L-histidinamide | 0.56 ± 0.04 | |
| H-His-Trp-OH | 0.60 ± 0.03 | |
| L-histidinol | 1.53 ± 0.12 | |
| L-histidine | 4.4 ± 0.2 | |
| 4-imidazole-carboxaldehyde | 7.6 ± 0.7 | |
| imidazole-4-carbonic acid methylester | 14.5 ± 0.6 | |
| L-histamine | 0.85 ± 0.04 | |
| C-4,5 derivatives | | |
| 5-hydroxymethyl-4-methyl-imidazole | 0.129 ± 0.005 | |
| 4-amino-imidazole-5-carbonic acid amide | 15.5 ± 0.5 | |
| 4,5-diphenyl-imidazole | no inhibition | |
| 4,5-dicyanoimidazole | no inhibition | |
| C-2 derivatives | | |
| 2-methyl-benzylimidazole | 0.165 ± 0.004 | |
| 2-ethyl-4-methyl-imidazole | 0.58 ± 0.04 | |
| 2-aminobenzimidazole | 1.8 ± 0.1 | |
| 2-chloro-1H-benzimidazole | no inhibition | |
| Others | | |
| 3-(1H-imidazol-1-yl)-1-(3-methylbenzo[b]thiophene-2-yl)propan-1-one | 0.0025 ± 0.0001 | (structure shown) |
| 4-[(1-methyl-1H-imidazol-5-yl)methyl]-3 propyldihydrofuran-2-(3H)-one | 0.0067 ± 0.0003 | (structure shown) |
| 4-[2-(1H-imidazol-1-yl)ethoxy]benzoic acid | 0.0034 ± 0.0001 | (structure shown) |

TABLE 3-continued

Inhibitory constants of imidazole derivatives in the human QC catalyzed reaction. Determinations were performed at 30° C. in 0.05 M Tris-HCl pH 8.0, containing 5 mM EDTA.

| Compound | Ki-value (mM) | Structure |
| --- | --- | --- |
| 3-[3-(1H-imidazol-1-yl)propyl]2-thioxoimidazolidin-4-one | 0.00041 ± 0.00001 | 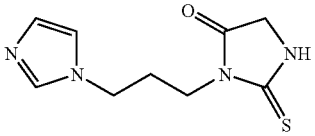 [SMILES: O=C1CNC(=S)N1CCCn1ccnc1] |
| 5-nitro-2-[2-([{3-(1H-imidazol 1-yl-)propyl}amino]carbonyl)phenyl]furamide | 0.0066 ± 0.0004 | 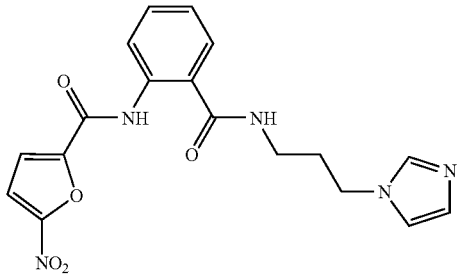 [SMILES: O=C(Nc1ccccc1C(=O)NCCCn1ccnc1)c1ccc([N+](=O)[O-])o1] |
| N-(4-chlorophenyl)-N'-[2-(1H imidazol-1-yl)ethyl]thiourea | 0.00165 ± 0.00007 | 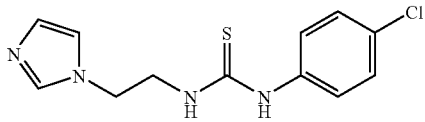 [SMILES: S=C(NCCn1ccnc1)Nc1ccc(Cl)cc1] |
| 2-[(5-imidazol-1-ylmethylpyrrolidine-2-carbonyl)-amino]-propionic acid methyl ester | 0.0322 ± 0.0007 | 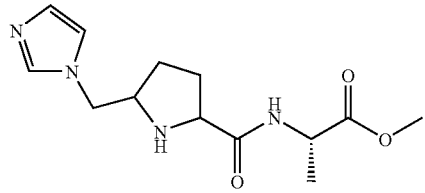 [SMILES: COC(=O)[C@H](C)NC(=O)C1CCC(Cn2ccnc2)N1] |
| 2-[(5-Imidazol-1-ylmethyl-2,3-dihydro-1H-pyrrole-2-carbonyl)amino]-propionic acid methylester | n.d. | 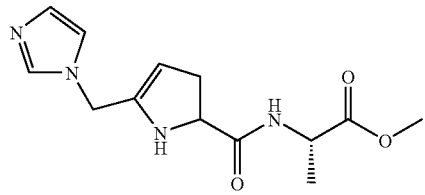 [SMILES: COC(=O)[C@H](C)NC(=O)C1CC=C(Cn2ccnc2)N1] |
| Imidazo<1.5a>pyridine | 0.0356 ± 0.0005 | 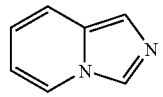 |
| Methyl (2S)-2-{[(2S)-2-amino-5- 0.164 ± 0.004 (1H-imidazol-1-ylamino)-5-oxopentanoyl]amino}-3 methylbutanoate | 0.164 ± 0.004 | 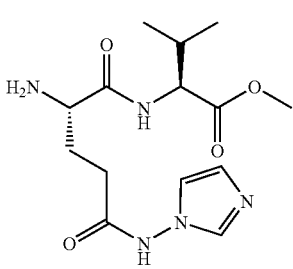 [SMILES: COC(=O)[C@@H](NC(=O)[C@@H](N)CCC(=O)Nn1ccnc1)C(C)C] |

TABLE 4

QC inhibition by L-histamine and its two biological metabolites
(also known as tele-methylhistamine).

| Compound | $K_i$ Value (mM) | Structure |
|---|---|---|
| L-histamine | 0.85 ± 0.04 | 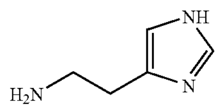 |
| 3-methyl-4-(β-aminoethyl)-imidazole | 0.120 ± 0.004 | |
| 1-methyl-4-(β-aminoethyl)-imidazole | n.i. | 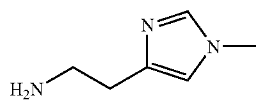 |

Surprisingly, during characterization of the enzymatic activity it was discovered that besides an N-terminal glutaminyl residue, N-terminal [β-homo-glutaminyl residues also fulfill properties as substrates of QCs from plants and mammals. The N-terminal β-homo-glutaminyl residue was converted into a five-membered lactam ring by catalysis of human and papaya QC, respectively. The results are described in example 5. The applied method is illustrated in example 2 and the peptide synthesis was performed as described in example 6.

Another preferred embodiment of the present invention comprises screening methods for effectors of QC.

A preferred screening method for identifying activity modifying effectors of QC from a group of compounds comprises the steps of:
 a) Contacting said compounds with QC under conditions which would permit binding therebetween;
 b) Adding a substrate of QC;
 c) Monitoring the conversion of the substrate or optionally measuring the residual QC activity; and
 d) Calculating changes in the substrate conversion and/or enzyme activity of QC to identify an activity modifying effector.

Another preferred screening method relates to a method for the identification and selection of effectors which interact directly or indirectly with the active-site bound metal ion of QC and comprises the following steps:
 a) Contacting said compounds with QC under conditions which would permit binding therebetween;
 b) Adding a substrate of QC which is subject to conversion by QC;
 c) Monitoring the conversion of the substrate or optionally measuring the residual QC activity; and
 d) Calculating changes in the substrate conversion and/or enzyme activity of QC wherein changes may be used to identify an activity modifying effector of QC.

Preferred for the use in the above described screening methods are mammalian QC or Papaya QC. Especially preferred is mammalian QC, since the effectors identified by these screening methods shall be used for the treatment of diseases in mammals, especially in humans.

The agents selected by the above described screening methods can work by decreasing the conversion of at least one substrate of QC (negative effectors, inhibitors), or by increasing the conversion of at least one substrate of QC (positive effectors, activators).

The compounds of the present invention can be converted into acid addition salts, especially pharmaceutically acceptable acid addition salts.

The salts of the compounds of the invention may be in the form of inorganic or organic salts.

The compounds of the present invention can be converted into and used as acid addition salts, especially pharmaceutically acceptable acid addition salts. The pharmaceutically acceptable salt generally takes a form in which a basic side chain is protonated with an inorganic or organic acid. Representative organic or inorganic acids include hydrochloric, hydrobromic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toulenesulfonic, cyclohexanesulfamic, salicylic, saccharinic or trifluoroacetic acid. All pharmaceutically acceptable acid addition salt forms of the compounds of the present invention are intended to be embraced by the scope of this invention.

In view of the close relationship between the free compounds and the compounds in the form of their salts, whenever a compound is referred to in this context, a corresponding salt is also intended, provided such is possible or appropriate under the circumstances.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms of the compounds may exist as polymorphs and as such are intended to be included in the present invention. In addition, some of the compounds may form solvates with water (i.e. hydrates) or common organic solvents, and such solvates are also intended to be encompassed within the scope of this invention.

The compounds, including their salts, can also be obtained in the form of their hydrates, or include other solvents used for their crystallization.

In a further embodiment, the present invention provides a method of preventing or treating a condition mediated by modulation of the QC enzyme activity in a subject in need thereof which comprises administering any of the compounds of the present invention or pharmaceutical compositions thereof in a quantity and dosing regimen therapeutically effective to treat the condition. Additionally, the present invention includes the use of the compounds of this invention, and their corresponding pharmaceutically acceptable acid addition salt forms, for the preparation of a medicament for the prevention or treatment of a condition mediated by modulation of the QC activity in a subject. The compound may be administered to a patient by any conventional route of administration, including, but not limited to, intravenous, oral, subcutaneous, intramuscular, intradermal, parenteral and combinations thereof.

In a further preferred form of implementation, the invention relates to pharmaceutical compositions, that is to say, medicaments, that contain at least one compound of the invention or salts thereof, optionally in combination with one or more pharmaceutically acceptable carriers and/or solvents.

The pharmaceutical compositions may, for example, be in the form of parenteral or enteral formulations and contain appropriate carriers, or they may be in the form of oral formulations that may contain appropriate carriers suitable for oral administration. Preferably, they are in the form of oral formulations.

The effectors of QC activity administered according to the invention may be employed in pharmaceutically administrable formulations or formulation complexes as inhibitors or in combination with inhibitors, substrates, pseudosubstrates, inhibitors of QC expression, binding proteins or antibodies of those enzyme proteins that reduce the QC protein concentration in mammals. The compounds of the invention make it possible to adjust treatment individually to patients and diseases, it being possible, in particular, to avoid individual intolerances, allergies and side-effects.

The compounds also exhibit differing degrees of activity as a function of time. The doctor providing treatment is thereby given the opportunity to respond differently to the individual situation of patients: he is able to adjust precisely, on the one hand, the speed of the onset of action and, on the other hand, the duration of action and especially the intensity of action.

A preferred treatment method according to the invention represents a new approach for the prevention or treatment of a condition mediated by modulation of the QC enzyme activity in mammals. It is advantageously simple, susceptible of commercial application and suitable for use, especially in the treatment of diseases that are based on unbalanced concentration of physiological active QC substrates, e.g. listed in Tables 1 and 2, in mammals and especially in human medicine.

The compounds may be advantageously administered, for example, in the form of pharmaceutical preparations that contain the active ingredient in combination with customary additives like diluents, excipients and/or carriers known from the prior art. For example, they can be administered parenterally (for example i.v. in physiological saline solution) or enterally (for example orally, formulated with customary carriers).

Depending upon their endogenous stability and their bioavailability, one or more doses of the compounds can be given per day in order to achieve the desired normalisation of the blood glucose values. For example, such a dosage range in humans may be in the range of from about 0.01 mg to 250.0 mg per day, preferably in the range of from about 0.01 to 100 mg of compound per kilogram of body weight.

By administering effectors of QC activity to a mammal it could be possible to prevent or alleviate or treat conditions selected from Alzheimer's disease, Down Syndrome, ulcer disease and gastric cancer with or w/o *Heliobacter pylori* infections, pathogenic psychotic conditions, schizophrenia, infertility, neoplasia, inflammatory host responses, cancer, psoriasis, rheumatoid arthritis, atherosclerosis, impaired humoral and cell-mediated immune responses, leukocyte adhesion and migration processes in the endothelium, impaired food intake, sleep-wakefulness, impaired homeostatic regulation of energy metabolism, impaired autonomic function, impaired hormonal balance and impaired regulation of body fluids.

Further, by administering effectors of QC activity to a mammal it could be possible to stimulate gastrointestinal tract cell proliferation, preferably proliferation of gastric mucosal cells, epithelial cells, acute acid secretion and the differentiation of acid producing parietal cells and histamine-secreting enterochromaffin-like cells.

In addition, administration of QC inhibitors to mammals may lead to a loss of sperm cell function thus suppressing male fertility. Thus, the present invention provides a method for the regulation and control of male fertility and the use of activity lowering effectors of QC for the preparation of contraceptive medicaments for males.

Furthermore, by administering effectors of QC activity to a mammal it may be possible to suppress the proliferation of myeloid progenitor cells.

The compounds used according to the invention can accordingly be converted in a manner known per se into conventional formulations, such as, for example, tablets, capsules, dragées, pills, suppositories, granules, aerosols, syrups, liquid, solid and cream-like emulsions and suspensions and solutions, using inert, non-toxic, pharmaceutically suitable carriers and additives or solvents. In each of those formulations, the therapeutically effective compounds are preferably present in a concentration of approximately from 0.1 to 80% by weight, more preferably from 1 to 50% by weight, of the total mixture, that is to say, in amounts sufficient for the mentioned dosage latitude to be obtained.

The substances can be used as medicaments in the form of dragées, capsules, bitable capsules, tablets, drops, syrups or also as suppositories or as nasal sprays.

The formulations may be advantageously prepared, for example, by extending the active ingredient with solvents and/or carriers, optionally with the use of emulsifiers and/or dispersants, it being possible, for example, in the case where water is used as diluent, for organic solvents to be optionally used as auxiliary solvents.

Examples of excipients useful in connection with the present invention include: water, non-toxic organic solvents, such as paraffins (for example natural oil fractions), vegetable oils (for example rapeseed oil, groundnut oil, sesame oil), alcohols (for example ethyl alcohol, glycerol), glycols (for example propylene glycol, polyethylene glycol); solid carriers, such as, for example, natural powdered minerals (for example highly disperse silica, silicates), sugars (for example raw sugar, lactose and dextrose); emulsifiers, such as non-ionic and anionic emulsifiers (for example polyoxyethylene fatty acid esters, polyoxyethylene fatty alcohol ethers, alkylsulphonates and arylsulphonates), dispersants (for example lignin, sulphite liquors, methylcellulose, starch and polyvinylpyrrolidone) and lubricants (for example magnesium stearate, talcum, stearic acid and sodium lauryl sulphate) and optionally flavourings.

Administration may be carried out in the usual manner, preferably enterally or parenterally, especially orally. In the case of enteral administration, tablets may contain in addition to the mentioned carriers further additives such as sodium citrate, calcium carbonate and calcium phosphate, together with various additives, such as starch, preferably potato starch, gelatin and the like. Furthermore, lubricants, such as magnesium stearate, sodium lauryl sulphate and talcum, can be used concomitantly for tabletting. In the case of aqueous suspensions and/or elixirs intended for oral administration, various taste correctives or colourings can be added to the active ingredients in addition to the above-mentioned excipients.

In the case of parenteral administration, solutions of the active ingredients using suitable liquid carriers can be employed. In general, it has been found advantageous to administer, in the case of intravenous administration, amounts of approximately from 0.01 to 2.0 mg/kg, preferably approximately from 0.01 to 1.0 mg/kg, of body weight per day to obtain effective results and, in the case of enteral administration, the dosage is approximately from 0.01 to 2 mg/kg, preferably approximately from 0.01 to 1 mg/kg, of body weight per day.

It may nevertheless be necessary in some cases to deviate from the stated amounts, depending upon the body weight of the experimental animal or the patient or upon the type of administration route, but also on the basis of the species of animal and its individual response to the medicament or the interval at which administration is carried out. Accordingly, it may be sufficient in some cases to use less than the above-mentioned minimum amount, while, in other cases, the mentioned upper limit will have to be exceeded. In cases where relatively large amounts are being administered, it may be advisable to divide those amounts into several single doses over the day. For administration in human medicine, the same dosage latitude is provided. The above remarks apply analogously in that case.

EXAMPLES OF PHARMACEUTICAL FORMULATIONS

1. Capsules containing 100 mg of a compound of the invention per capsule:

For approximately 10,000 capsules a solution of the following composition is prepared:

| compound of the invention | 1.0 kg |
|---|---|
| glycerol | 0.5 kg |
| polyethylene glycol | 3.0 kg |
| water | 0.5 kg |
| | 5.0 kg |

The solution is introduced into soft gelatin capsules in a manner known per se. The capsules are suitable for chewing or swallowing.

2. Tablets or coated tables or dragées containing 100 mg of a compound of the invention:

The following amounts refer to the preparation of 100,000 tablets:

| compound of the invention, finely ground | 10.0 kg |
|---|---|
| glucose | 4.35 kg |
| lactose | 4.35 kg |
| starch | 4.50 kg |
| cellulose, finely ground | 4.50 kg |

The above constituents are mixed and then provided with a solution prepared from

| polyvinylpyrrolidone | | 2.0 kg |
|---|---|---|
| polysorbate | | 0.1 kg |
| and water | approx. | 5.0 kg | and granulated in a manner known per se by grating the moist mass and, after the addition of 0.2 kg of magnesium stearate, drying it. The finished tablet mixture of 30.0 kg is processed to form convex tablets weighing 300 mg. Ideally, the tablets can be coated or sugar-coated in a manner known per se.

The pharmaceutical compositions defined throughout the specification advantageously contain a combination of at least one effector of QC activity and at least one DP IV inhibitor. Such pharmaceutical compositions are especially useful for the treatment of Alzheimer's Disease and Down Syndrome.

Example 1

Preparation of Human and Papaya QC

Host Strains and Media

*Pichia pastoris* strain X33 (AOX1, AOX2), used for the expression of human QC was grown, transformed and analyzed according to the manufacturer's instructions (Invitrogen). The media required for *P. pastoris*, i.e. buffered glycerol (BMGY) complex or methanol (BMMY) complex medium, and the fermentation basal salts medium were prepared according to the manufacturer's recommendations.

Molecular Cloning of Plasmid Vectors Encoding the Human QC

All cloning procedures were done applying standard molecular biology techniques. For expression in yeast, the vector pPICZB (Invitrogen) was used. The pQE-31 vector (Qiagen) was used to express the human QC in *E. coli*. The cDNA of the mature QC starting with codon 38 was fused in frame with the plasmid encoded 6× histidine tag. After amplification utilizing the primers pQCyc-1 and pQCyc-2 (Table 1) and subcloning, the fragment was inserted into the expression vector employing the restriction sites of SphI and HindIII.

Transformation of *P. pastoris* and Mini-Scale Expression

Plasmid DNA was amplified in *E. coli* JM109 and purified according to the recommendations of the manufacturer (Qiagen). In the expression plasmid used, pPICZαB, three restriction sites are provided for linearization. Since SacI and BstXI cut within the QC cDNA, PmeI was chosen for linearization. 20-30 μg plasmid DNA was linearized with PmeI, precipitated by ethanol, and dissolved in sterile, deionized water. 10 μg of the DNA was then applied for transformation of competent *P. pastoris* cells by electroporation according to the manufacturer's instructions (BioRad). Selection was done on plates containing 150 μg/ml Zeocin. One transformation using the linearized plasmid yielded several hundred transformants.

In order to test the recombinant yeast clones for QC expression, recombinants were grown for 24 h in 10 ml conical tubes containing 2 ml BMGY. Afterwards, the yeast was centrifuged and resuspended in 2 ml BMMY containing 0.5% methanol. This concentration was maintained by addition of methanol every 24 h up to 72 h. Subsequently, QC activity in the supernatant was determined. The presence of the fusion protein was confirmed by western blot analysis using an antibody directed against the 6× histidine tag (Qiagen). Clones that displayed the highest QC activity were chosen for further experiments and fermentation.

Large-Scale Expression in a Fermenter

Expression of the QC was performed in a 5 l reactor (Biostat B, B. Braun biotech), essentially as described in the "*Pichia* fermentation process guidelines" (Invitrogen). Briefly, the cells were grown in the fermentation basal salts medium supplemented with trace salts, and with glycerol as the sole carbon source (pH 5.5). During an initial batch phase for about 24 h and a subsequent fed-batch phase for about 5 h, cell mass was accumulated. Once a cell wet weight of 200 g/l was achieved, induction of QC expression was performed using methanol applying a three-step feeding profile for an entire fermentation time of approximately 60 h. Subsequently, cells were removed from the QC-containing supernatant by centrifugation at 6000×g, 4° C. for 15 min. The pH was adjusted to 6.8 by addition of NaOH, and the resultant turbid solution was centrifuged again at 37000×g, 4° C. for 40 min. In cases of continued turbidity, an additional filtration step was applied using a cellulose membrane (pore width 0.45 μm).

Purification of 6×Histidine Tagged QC Expressed in *P. Pastoris*

The His-tagged QC was first purified by immobilized metal affinity chromatography (IMAC). In a typical purification, 1000 ml of culture supernatant were applied to a $Ni^{2+}$-loaded Chelating Sepharose FF column (1.6×20 cm, Pharmacia), that was equilibrated with 50 mM phosphate buffer, pH 6.8, containing 750 mM NaCl, at a flow rate of 5 ml/min. After washing with 10 column volumes of equilibration buffer and 5 column volumes of equilibration buffer containing 5 mM histidine, the bound protein was eluted by a shift to 50 mM phosphate buffer, pH 6.8, containing 150 mM NaCl and 100 mM histidine. The resulting eluate was dialyzed against 20 mM Bis-Tris/HCl, pH 6.8, at 4° C. overnight. Subsequently, the QC was further purified by anion exchange chromatography on a Mono Q6 column (BioRad), equilibrated with dialysis buffer. The QC-containing fraction was loaded onto the column using a flow rate of 4 ml/min. The column was then washed with equilibration buffer containing 100 mM NaCl. The elution was performed by two gradients resulting in equilibration buffer containing 240 mM and 360 mM NaCl in 30 or 5 column volumes, respectively. Fractions of 6 ml were collected and the purity was analyzed by SDS-PAGE. Fractions containing homogenous QC were pooled and concentrated by ultrafiltration. For long-term storage (−20° C.), glycerol was added to a final concentration of 50%. Protein was quantified according to the methods of Bradford or Gill and von Hippel (Bradford, M. M. 1976 *Anal Biochem* 72, 248-254; Gill, S. C. and von Hippel, P. H. 1989 *Anal Biochem* 182, 319-326.).

Expression and Purification of QC in *E. Coli*

The construct encoding the QC was transformed into M15 cells (Qiagen) and grown on selective LB agar plates at 37° C. Protein expression was carried out in LB medium containing 1% glucose and 1% ethanol at room temperature. When the culture reached an $OD_{600}$ of approximately 0.8, expression was induced with 0.1 mM IPTG overnight. After one cycle of freezing and thawing, cells were lysed at 4° C. by addition of 2.5 mg/ml lysozyme in 50 mM phosphate buffer, pH 8.0, containing 300 mM NaCl and 2 mM histidine for approximately 30 min. The solution was clarified by centrifugation at 37000×g, 4° C. for 30 min, followed by a filtration applying a glass frit (DNA separation) and two additional filtration steps applying cellulose filters for crude and fine precipitates. The supernatant (approx. 500 ml) was applied onto a $Ni^{2+}$-affinity column (1.6×20 cm) at a flow rate of 1 ml/min. Elution of QC was carried out with 50 mM phosphate buffer containing 150 mM NaCl and 100 mM histidine. The QC-containing fraction was concentrated by ultrafiltration.

Purification of QC from Papaya Latex

QC from papaya latex was prepared using the BioCAD 700E (Perseptive Biosystems, Wiesbaden, Germany) with a modified version of a previously reported method (Zerhouni, S. et al. 1989 *Biochim Biophys Acta* 138, 275-290). 50 g latex was dissolved in water and centrifugated as described therein. Inactivation of proteases was performed with S-methyl methanethiosulfonate, and the resultant crude extract was dialyzed. After dialysis, the entire supernatant was loaded onto a (21×2.5 cm i.d.) SP Sepharose Fast Flow column, equilibrated with 100 mM sodium acetate buffer, pH 5.0 (flow rate 3 ml/min). Elution was performed in three steps by increasing sodium acetate buffer concentration at a flow rate of 2 ml/min. The first step was a linear gradient from 0.1 to 0.5 M acetate buffer in 0.5 column volumes. The second step was a linear increase in buffer concentration from 0.5 to 0.68 M in four column volumes. During the last elution step, one column volume of 0.85 M buffer was applied. Fractions (6 ml) containing the highest enzymatic activity were pooled. Concentration and buffer changes to 0.02 M Tris/HCl, pH 8.0 were performed via ultrafiltration (Amicon; molecular mass cut-off of the membrane 10 kDa).

Ammonium sulfate was added to the concentrated papaya enzyme, obtained from the ion exchange chromatography step to a final concentration of 2 M. This solution was applied onto a (21×2.5 cm i.d.) Butyl Sepharose 4 Fast Flow column (flow rate 1.3 ml/min), equilibrated with 2 M ammonium sulfate, 0.02 M Tris/HCl, pH 8.0. Elution was performed in three steps with decreasing concentrations of ammonium sulfate. During the first step a linear gradient from 2 to 0.6 M ammonium sulfate, 0.02 M Tris/HCl, pH 8.0 was applied for 0.5 column volumes at a flow rate of 1.3 ml/min. The second step was a linear gradient from 0.6 to 0 M ammonium sulfate, 0.02 M Tris/HCl, pH 8.0, in 5 column volumes at a flow rate of 1.5 ml/min. The last elution step was carried out by applying 0.02 M Tris/HCl at pH 8.0 for 2 column volumes at a flow rate of 1.5 ml/min. All fractions containing QC activity were pooled and concentrated by ultrafiltration. The resultant homogenous QC was stored at −70° C. Final protein concentrations were determined using the method of Bradford, compared to a standard curve obtained with bovine serum albumin.

Example 2

Assays for Glutaminyl Cyclase Activity
Fluorometric Assays

All measurements were performed with a BioAssay Reader HTS-7000Plus for microplates (Perkin Elmer) at 30° C. QC activity was evaluated fluorometrically using H-Gln-βNA. The samples consisted of 0.2 mM fluorogenic substrate, 0.25 U pyroglutamyl aminopeptidase (Unizyme, Hørsholm, Denmark) in 0.2 M Tris/HCl, pH 8.0 containing 20 mM EDTA and an appropriately diluted aliquot of QC in a final volume of 250 µl. Excitation/emission wavelengths were 320/410 nm. The assay reactions were initiated by addition of glutaminyl cyclase. QC activity was determined from a standard curve of β-naphthylamine under assay conditions. One unit is defined as the amount of QC catalyzing the formation of 1 µmol pGlu-βNA from H-Gln-βNA per minute under the described conditions.

In a second fluorometric assay, QC was activity was determined using H-Gln-AMC as substrate. Reactions were carried out at 30° C. utilizing the NOVOStar reader for microplates (BMG labtechnologies). The samples consisted of varying concentrations of the fluorogenic substrate, 0.1 U pyroglutamyl aminopeptidase (Qiagen) in 0.05 M Tris/HCl, pH 8.0 containing 5 mM EDTA and an appropriately diluted aliquot of QC in a final volume of 250 µl. Excitation/emission wavelengths were 380/460 nm. The assay reactions were initiated by addition of glutaminyl cyclase. QC activity was determined from a standard curve of 7-amino-4-methylcoumarin under assay conditions. The kinetic data were evaluated using GraFit sofware.

Spectrophotometric Assay of QC

This novel assay was used to determine the kinetic parameters for most of the QC substrates. QC activity was analyzed spectrophotometrically using a continuous method, that was derived by adapting a previous discontinuous assay (Bateman, R. C. J. 1989 *J Neurosci Methods* 30, 23-28) utilizing glutamate dehydrogenase as auxiliary enzyme. Samples consisted of the respective QC substrate, 0.3 mM NADH, 14 mM □-Ketoglutaric acid and 30 U/ml glutamate dehydrogenase in a final volume of 250 µl. Reactions were started by addition of QC and persued by monitoring of the decrease in absorbance at 340 nm for 8-15 min. Typical time courses of product formation are presented in FIG. 1.

The initial velocities were evaluated and the enzymatic activity was determined from a standard curve of ammonia under assay conditions. All samples were measured at 30° C., using either the SPECTRAFluor Plus or the Sunrise (both from TECAN) reader for microplates. Kinetic data was evaluated using GraFit software.

Inhibitor Assay

For inhibitor testing, the sample composition was the same as described above, except of the putative inhibitory compound added. For a rapid test of QC-inhibition, samples contained 4 mM of the respective inhibitor and a substrate concentration at 1 $K_M$. For detailed investigations of the inhibition and determination of $K_i$-values, influence of the inhibitor on the auxiliary enzymes was investigated first. In every case, there was no influence on either enzyme detected, thus enabling the reliable determination of the QC inhibition. The inhibitory constant was evaluated by fitting the set of progress curves to the general equation for competitive inhibition using GraFit software.

Example 3

MALDI-TOF Mass Spectrometry

Matrix-assisted laser desorption/ionization mass spectrometry was carried out using the Hewlett-Packard G2025 LD-TOF System with a linear time of flight analyzer. The instrument was equipped with a 337 nm nitrogen laser, a potential acceleration source (5 kV) and a 1.0 m flight tube. Detector operation was in the positive-ion mode and signals were recorded and filtered using LeCroy 9350M digital storage oscilloscope linked to a personal computer. Samples (5 µl) were mixed with equal volumes of the matrix solution. For matrix solution we used DHAP/DAHC, prepared by solving 30 mg 2',6'-dihydroxyacetophenone (Aldrich) and 44 mg diammonium hydrogen citrate (Fluka) in 1 ml acetonitrile/0.1% TFA in water (1/1, v/v). A small volume (≈1 µl) of the matrix-analyte-mixture was transferred to a probe tip and immediately evaporated in a vacuum chamber (Hewlett-Packard G2024A sample prep accessory) to ensure rapid and homogeneous sample crystallization.

For long-term testing of $Glu^1$-cyclization, Aβ-derived peptides were incubated in 100 µl 0.1 M sodium acetate buffer, pH 5.2 or 0.1 M Bis-Tris buffer, pH 6.5 at 30° C. Peptides were applied in 0.5 mM [Aβ3-11a] or 0.15 mM [Aβ3-21a] concentrations, and 0.2 U QC was added all 24 hours.

In case of Aβ3-21a, the assays contained 1% DMSO. At different times, samples were removed from the assay tube, peptides extracted using ZipTips (Millipore) according to the manufacturer's recommendations, mixed with matrix solution (1:1 v/v) and subsequently the mass spectra recorded. Negative controls did either contain no QC or heat deactivated enzyme. For the inhibitor studies the sample composition was the same as described above, with exception of the inhibitory compound added (5 mM benzimidazole or 2 mM 1,10-phenanthroline).

Example 4 pH Dependence

Figure 2:
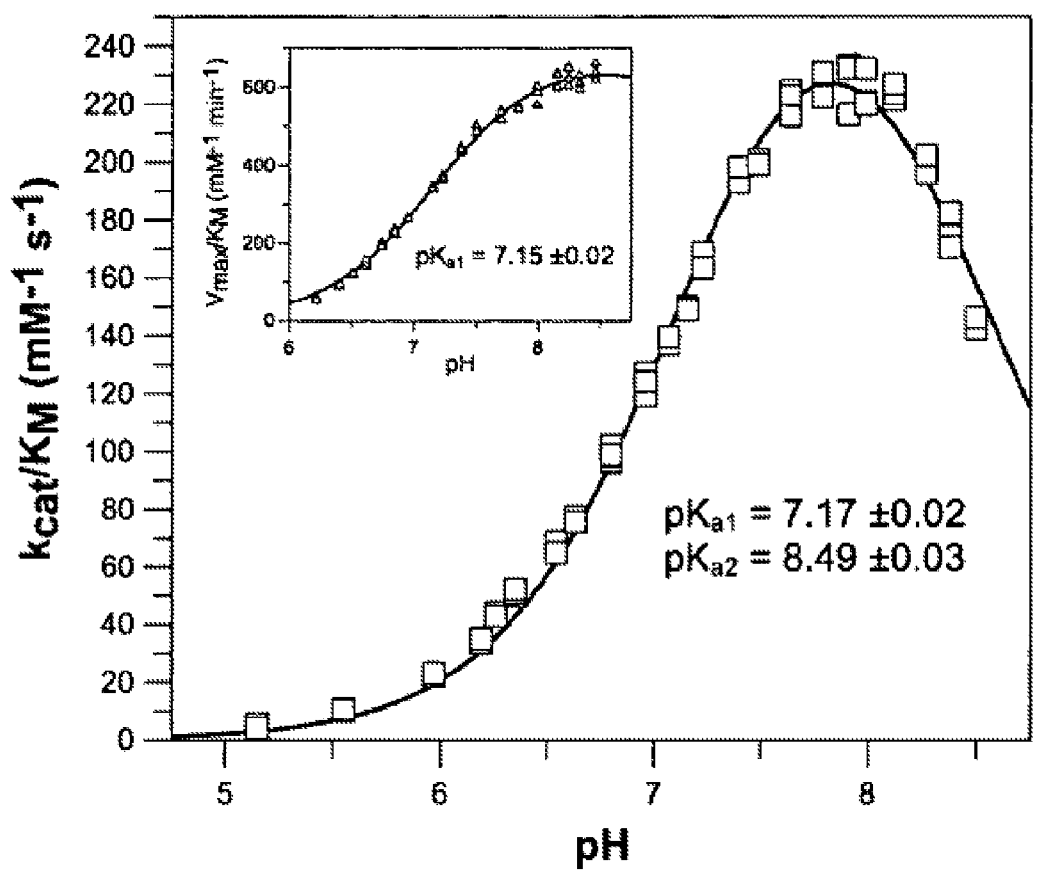
FIG. 2 shows the pH dependence of human and papaya (inset) QC, determined under first-order rate conditions using Gln-,βNA as substrate. In case of human QC, a buffer system providing a constant ionic strength according to Ellis and Morrison was used, consisting of 25 mM MES, 25 mM acetic acid and 50 mM Tris (Ellis, K. J. and Morrison, J. F. 1982 *Methods Enzymol.* 87, 405-426). Due to a slightly inhibiting effect of Tris, papaya QC was investigated using a 50 mM Mops buffer. The ionic strength was adjusted to 0.05 M by addition of NaCl. The rate profiles were evaluated by fitting to a model that is based on dissociating groups. In case of papaya QC, a pKa of 7.13±0.03 was obtained by fitting of the data to a single dissociation model.

The pH-dependence of catalysis of human and papaya QC was investigated under first-order rate conditions, thus reflecting the impact of the proton concentration on the specificity constant $k_{cat}/K_M$. For this purpose, the coupled enzymatic assay using pyroglutamyl aminopeptidase as auxiliary enzyme and Gln-βNA as substrate was used. Pyroglutamyl aminopeptidase was shown to be active and stable between pH 5.5-8.5 (Tsuru, D. et al. 1978 *J Biochem (Tokyo)* 84, 467-476). Hence, the assay enabled the study of QC catalysis in this pH-region. The rate profiles obtained were fit to classical bell shaped curves, as shown in FIG. 2. The human QC bears a very narrow pH-dependence with an optimum at about pH 7.8-8.0. The rate tended to decrease at more basic pH. This is in contrast to the rate profile observed with papaya QC, which showed no drop in activity up to pH 8.5 (FIG. 2, inset). However, both enzymes had their optimum of specificity at pH 8. Surprisingly, evaluation of the curves revealed identical $pK_a$-values in the acidic range of 7.17±0.02 and 7.15±0.02 for human and papaya QC, respectively.

The reduction of the activity of human QC at basic pH-values was obviously due to dissociation of a group with a $pK_a$ of approximately 8.5. In case of papaya QC, there was no excessive data point collection in the basic pH-range possible to enable a reliable determination of the second $pK_a$ value. This is supported by fitting of the data to a single dissociation model, resulting in an almost identical $pK_a$-value (pKa 7.13±0.03) compared to fitting the data to a double dissociation model. This indicates that both $pK_a$-values are fairly separated.

pH Stability

Figure 3:
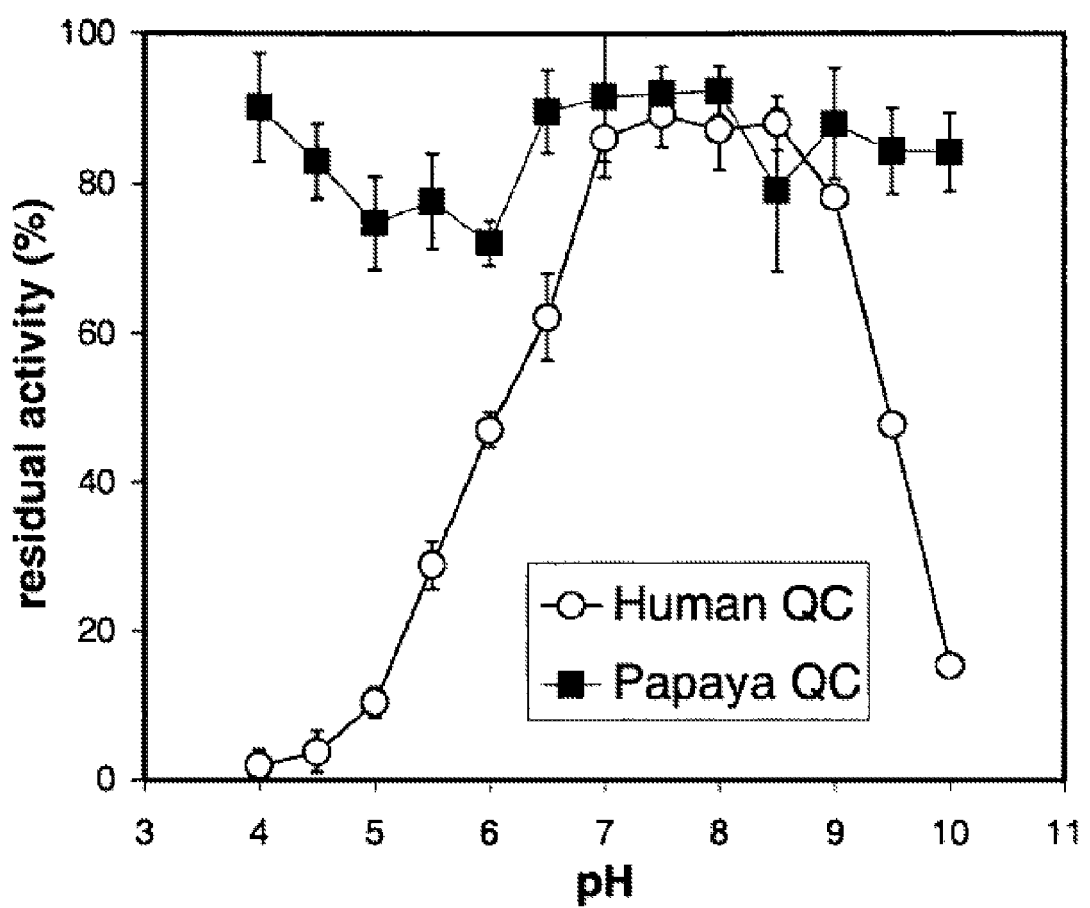
FIG. 3 shows the effect of the pH on the stability of the QC from Papaya latex and human QC. An enzyme stock solution was diluted 20-fold in 0.1 M buffer of various pH values (pH 4-7 sodium citrate, pH 7-10 sodium phosphate). Enzyme solutions were incubated at 30° C. for 30 min and subsequently enzymatic activity was analyzed according to the standard protocol.

The stability of the glutaminyl cyclases was investigated by incubating the plant and animal enzymes at 30° C. for 30 min at different pH values between pH 4-10. Afterwards, QC activity was determined under standard conditions. The results are shown in FIG. 3.

The QC from papaya latex was stable in the pH-range studied, without an obvious trend for instability in the acidic or basic range. In contrast, human QC only showed a comparable stability in the pH-range between 7 and 8.5, exhibiting a remarkable instability at pH values above pH 8.5 and below pH 6. Thus, the region around pH 8 seems to be optimal for activity and stability of plant and human QC and a suitable pH-value for performing a substrate specificity comparison of the QCs.

Example 5

Determination of Substrate Specificity of QC

Spectrophotometric Assay

The continuous spectrophotometric assay was performed as described in example 2. Accordingly, QC activity is reflected by a decrease in absorbance at 340 nm caused by the ammonia release and subsequent consumption of $NADH/H^+$ due to formation of glutamate from α-ketoglutaric acid. As shown in FIG. 1, linear progress curves were monitored and there was a linear relationship between the measured activity and the concentration of QC. Furthermore, the kinetic parameters obtained for H-Gln-Gln-OH using the continuous assay presented here (Table 1) were in good agreement with those obtained using the discontinuous method ($K_M$=175±18 µM, $k_{cat}$=21.3±0.6 $s^{-1}$). In addition, the kinetic parameters for conversion of the substrates H-Gln-Ala-OH, H-Gln-Glu-OH, H-Gln-Gln-OH, H-Gln-OtBu and H-Gln-NH2 by papaya QC shown in Table 1 correspond well to those determined using a direct method at pH 8.8 and 37° C. (Gololobov, M. Y. et al. 1996 *Biol Chem Hoppe Seyler* 377, 395-398). Hence, it is quite obvious that the novel continuous assay provides reliable results.

Di-, Tri- and Dipeptide-Surrogates

Utilizing the novel continuous assay described above, about 30 compounds were tested as potential substrates of QC from *C. papaya* and human. The results are displayed in Table 5. By comparison of the specificities it was shown, that nearly all of the short peptide substrates are more efficiently converted by papaya QC compared to the human enzyme. Interestingly, for both enzymes substrates with large hydrophobic residues in the second position are the most potent ones, as shown by the specificities of H-Gln-Tyr-Ala-OH, H-Gln-Phe-Ala-NH² and H-Gln-Trp-Ala-NH² compared to those of other tripeptides or by the reactivities of the chromophoric substrates H-Gln-AMC, H-Gln-βNA and H-Gln-Tyr-OH in comparison to dipeptide substrates. For papaya QC, this finding is in agreement with earlier results showing that the specificity is in correlation with the size of the second amino acid residue (Gololobov, M. Y. et al. 1996 *Biol Chem Hoppe Seyler* 377, 395-398). The only striking difference in specificity of the plant and animal QC was observed in case of H-Gln-OtBu. Whereas the ester was converted by papaya QC with similar specificity compared to dipeptide substrates, it was converted about one order of magnitude slower by human QC.

Oligopeptides

Besides several dipeptides and tripeptides, a number of oligopeptides was tested upon conversion by papaya and human QC (Table 5). Interestingly, the overall difference in the specificities between human and plant QC for a set of tetrapeptides was not that large as it was observed for dipeptide and tripeptide substrates. This indicates that the amino acids in the $3^{rd}$ and $4^{th}$ position still affect the kinetic behavior especially of human QC. An exception, however, comprise the peptides with a proline residue in the second amino acid position which show noticeably reduced $k_{cat}/K_M$ values in a set of tetrapeptides of the structure H-Gln-$X_{aa}$-Tyr-Phe-NH² (Table 5). The reduction in specificity was more pronounced for human QC, leading to an approximately 8-fold difference in the $k_{cat}/K_M$-value as compared to papaya QC.

Slightly reduced specificities of human QC were also observed for conversion of substrates with a positively charged amino acid C-terminal of glutamine, as indicated by the specificities for H-Gln-Arg-Tyr-Phe-NH² (SEQ ID NO: 14), H-Gln-Arg-Tyr-Phe-NH² (SEQ ID NO: 14) and H-Gln-Lys-Arg-Leu-NH² (SEQ ID NO: 15) as compared to other tetrapeptides. Apparently, the reduced specificity was mainly due to a smaller turnover number. This effect was not the case for the plant enzyme.

TABLE 5

Kinetic evaluation of peptide substrates of human and Papaya QC

| Substrate | Human QC | | | | Papaya QC | | | |
|---|---|---|---|---|---|---|---|---|
| | $K_M$ (μM) | $k_{cat}$ (s⁻¹) | $K_i^*$ (mM) | $k_{cat}/K_M$ (mM⁻¹s⁻¹) | $K_M$ (μM) | $k_{cat}$ (s⁻¹) | $K_i^*$ (mM) | $k_{cat}/K_M$ (mM⁻¹s⁻¹) |
| H-Gln-OH | n.r. | n.r. | n.d. | n.r. | n.d. | n.d. | n.d. | 0.23 ± 0.1 |
| H-Gln-AMC | 54 ± 2 | 5.3 ± 0.1 | n.d. | 98 ± 2 | 42 ± 1 | 39.4 ± 0.4 | n.d. | 938 ± 13 |
| H-Gln-βNA | 70 ± 3 | 20.6 ± 0.5 | 1.21 ± 0.07 | 294 ± 6 | 38 ± 3 | 51.4 ± 1.4 | 1.20 ± 0.08 | 1353 ± 70 |
| H-Gln-OtBu | 1235 ± 74 | 6.7 ± 0.2 | n.i. | 5.4 ± 0.2 | 223 ± 9 | 49.4 ± 0.6 | n.i. | 222 ± 6 |
| H-Gln-NH₂ | 409 ± 40 | 12.8 ± 0.5 | n.i. | 31 t2 | 433 ± 13 | 44.8 ± 0.4 | n.i. | 103 ± 2 |
| H-Gln-Gly-OH | 247 ± 10 | 13.2 ± 0.2 | n.i. | 53 ± 1 | 641 ± 20 | 45.8 ± 0.4 | n.i. | 71 ± 2 |
| H-Gln-Ala-OH | 232 ± 5 | 57.2 ± 0.4 | n.i. | 247 ± 4 | 158 ± 8 | 69.8 ± 1.0 | n.i. | 442 ± 16 |
| H-Gln-Gln-OH | 148 ± 5 | 20.7 ± 0.2 | n.i. | 140 ± 2 | 44 ± 3 | 43.2 ± 0.7 | n.i. | 982 ± 51 |
| H-Gln-Glu-OH | 359 ± 10 | 24.7 ± 0.2 | n.i. | 58 ± 1 | 106 ± 5 | 50.3 ± 0.6 | n.i. | 475 ± 17 |
| H-Gln-Val-OH | 196 ± 5 | 17.2 ± 0.1 | n.i. | 88 ± 2 | n.d. | n.d. | n.i. | n.d. |
| H-Gln-Tyr-OH | 211 ± 5 | 94 ± 1 | n.i. | 446 ± 6 | n.d. | n.d. | n.i. | n.d. |
| H-Gln-Glu-Tyr-NH2 | 79 ± 2 | 45.1 ± 0.4 | n.i. | 524 ± 8 | 103 ± 4 | 53.6 ± 0.7 | n.i. | 520 ± 13 |
| H-Gln-Gly-Pro-OH | 130 ± 5 | 25.3 ± 0.2 | n.i. | 195 ± 7 | 333 ± 15 | 41.7 ± 0.5 | n.i. | 125 ± 4 |
| H-Gln-Tyr-Ala-OH | 101 ± 4 | 125 ± 1 | n.i. | 930 ± 27 | 63 ± 3 | 104.0 ± 1.0 | n.i. | 1650 ± 63 |
| H-Gln-Phe-Ala-NH₂ | 69 ± 3 | 109 ± 1 | n.i. | 1811 ± 64 | 111 ± 5 | 132.1 ± 0.6 | n.i. | 1190 ± 48 |
| H-Gln-Trp-Ala-NH₂ | 50 ± 2 | 47.0 ± 0.7 | n.i. | 940 ± 24 | 78 ± 5 | 151.8 ± 2.6 | n.i. | 1946 ± 91 |
| H-Gln-Arg-Gly-Ile-NH2 (SEQ ID NO: 16) | 143 ± 4 | 33.5 ± 0.4 | n.i. | 234 ± 4 | 123 ± 10 | 49.2 ± 1.7 | n.i. | 400 ± 19 |
| H-Gln-Asn-Gly-Ile-NH₂ (SEQ ID NO: 17) | 172 ± 5 | 56.6 ± 0.5 | n.i. | 329 ± 7 | 153 ± 9 | 51.4 ± 0.9 | n.i. | 336 ± 14 |
| H-Gln-Ser-Tyr-Phe-NH₂ (SEQ ID NO: 18) | 55 ± 3 | 52.8 ± 0.8 | n.i. | 960 ± 38 | 135 ± 6 | 64.9 ± 1.0 | n.i. | 481 ± 14 |
| H-Gln-Arg-Tyr-Phe-NH₂ (SEQ ID NO: 14) | 55 ± 2 | 29.6 ± 0.3 | n.i. | 538 ± 14 | 124 ± 6 | 48.9 ± 0.7 | n.i. | 394 ± 13 |
| H-Gln-Pro-Tyr-Phe-NH₂ (SEQ ID NO: 19) | 1889 ± 152 | 31.7 ± 1.2 | n.i. | 17 ± 1 | 149 ± 14 | 18.8 ± 0.6 | n.i. | 126 ± 8 |
| H-Gln-His-Tyr-Phe-NH₂ (SEQ ID NO: 20) | 68 ± 3 | 55.4 ± 0.7 | n.i. | 815 ± 26 | 92 ± 7 | 75.9 ± 1.4 | n.i. | 825 ± 48 |
| H-Gln-Gln-Tyr-Phe-NH₂ (SEQ ID NO: 21) | 41 ± 2 | 41.4 ± 0.4 | n.i. | 1010 ± 40 | 45 ± 2 | 52.9 ± 0.7 | n.i. | 1176 ± 37 |
| H-Gln-Glu-Tyr-Phe-NH₂ (SEQ ID NO: 22) | 47 ± 4 | 46 ± 1 | | 979 ± 62 | 100 ± 4 | 54.6 ± 0.6 | n.i. | 546 ± 16 |
| H-Gln-Glu-Ala-Ala-NH₂ (SEQ ID NO: 23) | 77 ± 4 | 46 ± 1 | n.i. | 597 ± 18 | 102 ± 4 | 53.7 ± 0.6 | n.i. | 526 ± 15 |

TABLE 5-continued

Kinetic evaluation of peptide substrates of human and Papaya QC

| | Human QC | | | | Papaya QC | | | |
|---|---|---|---|---|---|---|---|---|
| Substrate | $K_M$ (µM) | $k_{cat}$ (s$^{-1}$) | $K_i$* (mM) | $k_{cat}/K_M$ (mM$^{-1}$s$^{-1}$) | $K_M$ (µM) | $k_{cat}$ (s$^{-1}$) | $K_i$* (mM) | $k_{cat}/K_M$ (mM$^{-1}$s$^{-1}$) |
| H-Gln-Glu-Tyr-Ala-NH$_2$ (SEQ ID NO: 24) | 69 ± 2 | 42.1 ± 0.4 | n.i. | 610 ± 12 | 113 ± 5 | 44.7 ± 0.5 | n.i. | 396 ± 13 |
| H-Gln-Glu-Ala-Phe-NH$_2$ (SEQ ID NO: 25) | 39 ± 3 | 39 ± 1 | n.i. | 1000 ± 51 | 81 ± 3 | 48.5 ± 0.45 | n.i. | 599 ± 17 |
| H-Gln-Glu-Asp-Leu-NH$_2$ (SEQ ID NO: 26) | 55 ± 2 | 45.8 ± 0.5 | n.i. | 833 ± 21 | 107 ± 6 | 58.5 ± 0.4 | n.i. | 547 ± 27 |
| H-Gln-Lys-Arg-Leu-NH$_2$ (SEQ ID NO: 15) | 54 ± 3 | 33.4 ± 0.5 | n.i. | 619 ± 25 | 118 ± 6 | 48.2 ± 0.8 | n.i. | 408 ± 14 |

(n.r., not reactive; n.i., no inhibition; n.d., not determined; *for substrate inhibition)

Figure 4:
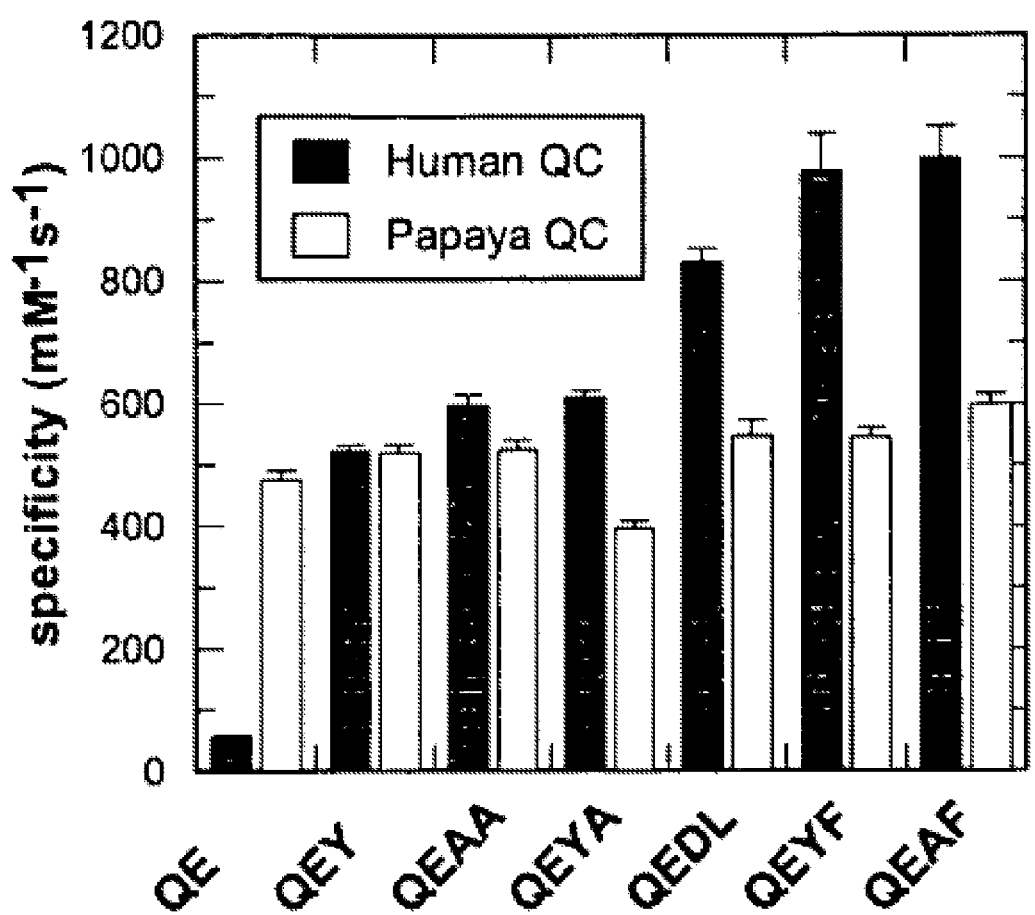
FIG. 4 shows the comparison of the specificity constant $k_{cat}/K_M$ for a set of substrates containing glutamate in the second amino acid position (peptides are disclosed as SEQ ID NOS 23, 24, 26, 22, and 25, respectively in order of appearance from left to right). Whereas an increase in specificity of human QC was detected from the di- to the tetrapeptides, no change was observed in case of papaya QC. The data presented here is a replot of the parameters given in Table 3.

The results obtained with the tetrapeptides give also rise to another conclusion. As already pointed out, papaya QC showed a higher selectivity for dipeptides. For some of the tetrapeptides, however, higher specificity-constants were observed with human QC, as shown in FIG. 4 providing a plot of the data given in Table 5, for a set of peptides containing glutamate in the second amino acid position. Furthermore, as the chain length increases from di- to tetrapeptides, the selectivity of human QC increases, in contrast to the results obtained with papaya QC. Additionally, the highest selectivity of human QC was recorded for the peptides containing bulky hydrophobic residues in the 3$^{rd}$ and 4$^{th}$ amino acid position, which indicate hydrophobic interactions with the enzyme. By comparison of the kinetic parameters for the respective peptides, the changes seem to be mainly due to lower KM-values, the turnover numbers for conversion of the peptides were found to be similar. Thus, the higher selectivity of human QC for longer peptides is considered to be the result of tighter binding of the more hydrophobic substrates to the enzyme.

The differences between human and plant QC observed with peptides containing hydrophobic amino acids in the 3$^{rd}$ and 4$^{th}$ position becomes also evident by a comparison of the specificity constants of the enzymes towards H-Gln-Arg-Gly-Ile-NH$_2$ (SEQ ID NO: 16) and H-Gln-Arg-Tyr-Phe-NH$_2$ (SEQ ID NO: 14) or H-Gln-Gln-OH and H-Gln-Gln-Tyr-Phe-OH. (SEQ ID NO: 21)

Human QC was also found to be more selective for homologous substrates containing N-terminal Gln and an increasing number of C-terminal Ala residues (Table 6). While the selectivity of human QC increased with substrate length, there was no such a trend with the papaya QC. Since human QC was less specific for a peptide containing a Ser residue in the sequence, also the nature of the side chain seems to be of importance (table 6).

TABLE 6

Influence of substrate length on the activity of human and Papaya QC

| | Human QC | | | Papaya QC | | |
|---|---|---|---|---|---|---|
| Substrate | $K_M$ (µM) | $k_{cat}$ (s$^{-1}$) | $k_{cat}/K_M$ (mM$^{-1}$ s$^{-1}$) | $K_M$ (µM) | $k_{cat}$ (s$^{-1}$) | $k_{cat}/K_M$ (mM$^{-1}$ s$^{-1}$) |
| H-Gln-Ala-NH$_2$ | 155 ± 9 | 40.1 ± 0.9 | 259 ± 9 | 212 ± 21 | 62.8 ± 3.0 | 296 ± 15 |
| H-Gln-Ala-Ala-NH$_2$ | 87 ± 3 | 76.3 ± 0.7 | 877 ± 22 | 164 ± 6 | 83.2 ± 1.0 | 507 ± 12 |
| H-Gln-Ala-Ala-Ala-Ala-NH$_2$ (SEQ ID NO: 27) | 65 ± 3 | 60.5 ± 0.7 | 1174 ± 43 | 197 ± 8 | 74.6 ± 1.0 | 379 ± 10 |
| H-Gln-Ala-Ala-Ser-Ala-Ala-NH$_2$ (SEQ ID NO: 28) | 79 ± 6 | 55.3 ± 1.6 | 700 ± 33 | 216 ± 6 | 78.5 ± 1.0 | 363 ± 5 |

Influence of Ionic Strength on Catalysis

Another parameter that was investigated concerning its influence on the substrate specificity was ionic strength. For that purpose, the kinetic parameters for cyclization of several substrates were determined in presence and absence of 0.5 M KCl (Table 7). Surprisingly, the selectivity for substrates with uncharged backbone did not change significantly by addition of the salt in case of QC from papaya latex and human QC. The specificity constants of the human QC for H-Gln-Ala-OH and H-Gln-Glu-OH, however, decreased by addition of KCl. As indicated by the individual kinetic parameters, this effect was due to an increasing $K_M$ and an only slightly decreasing $k_{cat}$-value. In case of papaya QC, there was no effect on either parameter detected. The effect seemed not to be due to the negatively charged substrate as such, since unchanged parameters were found for the negatively charged peptide H-Gln-Glu-Asp-Leu-NH$_2$ (SEQ ID NO: 26). An interesting effect of the salt addition was found for the positively charged substrates H-Gln-Arg-Gly-Ile-NH$_2$ (SEQ ID NO: 16) and H-Gln-Lys-Arg-Leu-NH$_2$(SEQ ID NO: 15). In case of plant and human QC, a positive effect on catalysis was determined mainly due to a smaller KM value and a slightly higher turnover number.

TABLE 7

Influence of ionic strength on catalysis of human and Papaya QC

| | Substrate | $K_M$ (mM) | $k_{cat}$ (s$^{-1}$) | $k_{cat}/K_M$ (mM$^{-1}$s$^{-1}$) | $K_i$ (mM) | $K_M$ (mM) | $k_{cat}$ (s$^{-1}$) | $k_{cat}/K_M$ (mM$^{-1}$s$^{-1}$) | $K_i$ (mM) |
|---|---|---|---|---|---|---|---|---|---|
| | | \multicolumn{4}{c}{0.05 M Tricine-NaOH, pH 8.0} | \multicolumn{4}{c}{0.05 M Tricine-NaOH, pH 8.0, 0.5 M KCl} |
| Papaya QC | H-Gln-NH$_2$ | 0.434 ± 0.015 | 43.4 ± 0.4 | 100 ± 3 | n.i. | 0.446 ± 0.010 | 45.2 ± 0.3 | 101 ± 2 | n.i. |
| | H-Gln-βNA | 0.036 ± 0.002 | 48.8 ± 1.0 | 1356 ± 50 | 1.14 ± 0.05 | 0.032 ± 0.002 | 47.2 ± 0.8 | 1475 ± 70 | 1.33 ± 0.07 |
| | H-Gln-Ala-OH | 0.137 ± 0.007 | 69.7 ± .9 | 509 ± 19 | n.i. | 0.143 ± 0.005 | 68.1 ± 0.6 | 480 ± 12 | n.i. |
| | H-Gln-Glu-OH | 0.098 ± 0.005 | 45.0 ± 0.5 | 459 ± 18 | n.i. | 0.094 ± 0.003 | 44.4 ± 0.3 | 472 ± 12 | n.i. |
| | H-Gln-Trp-Ala-NH$_2$ | 0.079 ± 0.005 | 138 ± 3 | 1747 ± 73 | n.i. | 0.072 ± 0.004 | 133 ± 3 | 1847 ± 61 | n.i. |
| | H-Gln-Arg-Gly-Ile-NH$_2$ (SEQ ID NO: 16) | 0.106 ± 0.008 | 52.9 ± 1.2 | 499 ± 26 | n.i. | 0.065 ± 0.005 | 48.4 ± 1.0 | 745 ± 42 | n.i. |
| | H-Gln-Lys-Arg-Leu-NH$_2$ (SEQ ID NO: 15) | 0.102 ± 0.007 | 50 ± 1 | 493 ± 22 | n.i. | 0.053 ± 0.002 | 58.1 ± 0.7 | 1096 ± 28 | n.i. |
| | H-Gln-Glu-Asp-Leu-NH$_2$ (SEQ ID NO: 26) | 0.109 ± 0.005 | 52.4 ± 0.7 | 481 ± 16 | n.i. | 0.094 ± 0.003 | 53.6 ± 0.5 | 570 ± 13 | n.i. |
| | | \multicolumn{4}{c}{0.05 M Tris-HCl, pH 8.0} | \multicolumn{4}{c}{0.05 M Tris-HCl, pH 8.0, 0.5 M KCl} |
| Human QC | H-Gln-NH$_2$ | 0.442 ± 0.030 | 12.8 ± 0.3 | 29 ± 1 | n.i. | 0.401 ± 0.014 | 12.2 ± 0.1 | 30 ± 1 | n.i. |
| | H-Gln-βNA | 0.076 ± 0.004 | 21.7 ± 0.5 | 285 ± 8 | 1.39 ± 0.08 | 0.063 ± 0.003 | 20.0 ± 0.4 | 318 ± 9 | 0.97 ± 0.04 |
| | H-Gln-Ala-OH | 0.269 ± 0.007 | 54.4 ± 0.5 | 202 ± 3 | n.i. | 0.357 ± 0.012 | 47.6 ± 0.6 | 133 ± 3 | n.i. |
| | H-Gln-Glu-OH | 0.373 ± 0.015 | 21.4 ± 0.3 | 57 ± 2 | n.i. | 0.607 ± 0.036 | 18.9 ± 0.5 | 31 ± 1 | n.i. |
| | H-Gln-Trp-Ala-NH$_2$ | 0.054 ± 0.003 | 50.8 ± 0.6 | 941 ± 41 | n.i. | 0.056 ± 0.002 | 50.0 ± 0.4 | 893 ± 25 | n.i. |
| | H-Gln-Arg-Gly-Ile-NH$_2$ (SEQ ID NO: 16) | 0.166 ± 0.013 | 31 ± 1 | 187 ± 9 | n.i. | 0.091 ± 0.005 | 29.8 ± 0.5 | 327 ± 12 | n.i. |
| | H-Gln-Lys-Arg-Leu-NH$_2$ (SEQ ID NO: 15) | 0.051 ± 0.003 | 29.4 ± 0.5 | 577 ± 24 | n.i. | 0.034 ± 0.001 | 31.6 ± 0.3 | 929 ± 19 | n.i. |
| | H-Gln-Glu-Asp-Leu-NH$_2$ (SEQ ID NO: 26) | 0.060 ± 0.002 | 46.6 ± 0.5 | 777 ± 18 | n.i. | 0.061 ± 0.002 | 45.6 ± 0.5 | 748 ± 16 | n.i. |

Physiological Substrates

In earlier studies, conversion of [Gln$^1$]-TRH and [Gln$^1$]-GnRH by QC was already shown for the QC from bovine and porcine pituitary (Busby, W. H. J. et al. 1987 *J Biol Chem* 262, 8532-8536; Fischer, W. H. and Spiess, J. 1987 *Proc Natl Acad Sci U S A* 84, 3628-3632). In addition to these already investigated pituitary hormones, three potential physiological substrates of human QC were synthesized and tested upon conversion, namely [Gln$^1$]Gastrin, [Gln$^1$]Neurotensin, and [Gln$^1$]FPP. The kinetic parameters for their conversion are listed in Table 1. Interestingly, the glutaminyl peptides are converted to the respective pyroglutamyl peptides with increasing specificity constants depending on their size, i.e., the first largest peptide pro-gastrin with 17 amino acids followed by pro-neurotensin, pro-GnRH, pro-TRH and pro-FPP. These findings correspond to the data obtained with the synthetic peptides.

Surprisingly, the longer substrates are also converted with higher selectivity by the plant enzyme, a result that contrasts in part with the findings for the shorter oligopeptides. Possibly, there are secondary binding interactions between substrate and enzyme far distant from the active site.

Peptides Comprising Modified Amino Acids

In order to further investigate the specificity and selectivity of the QCs, peptides were synthesized comprising either a modified N-terminal glutaminyl residue or a modified amino acid in the second position. The conversion of these peptides was investigated qualitatively utilizing MALDI-TOF mass spectrometry (see also example 3). Due to the cyclization of the glutaminyl residue or its analog, respectively, a mass difference of the substrate and the product of catalysis is detected. In cases of ammonia liberation of one mole per mole of substrate, the conversion was also analyzed quantitatively using the spectrophotometric assay.

Figure 5:
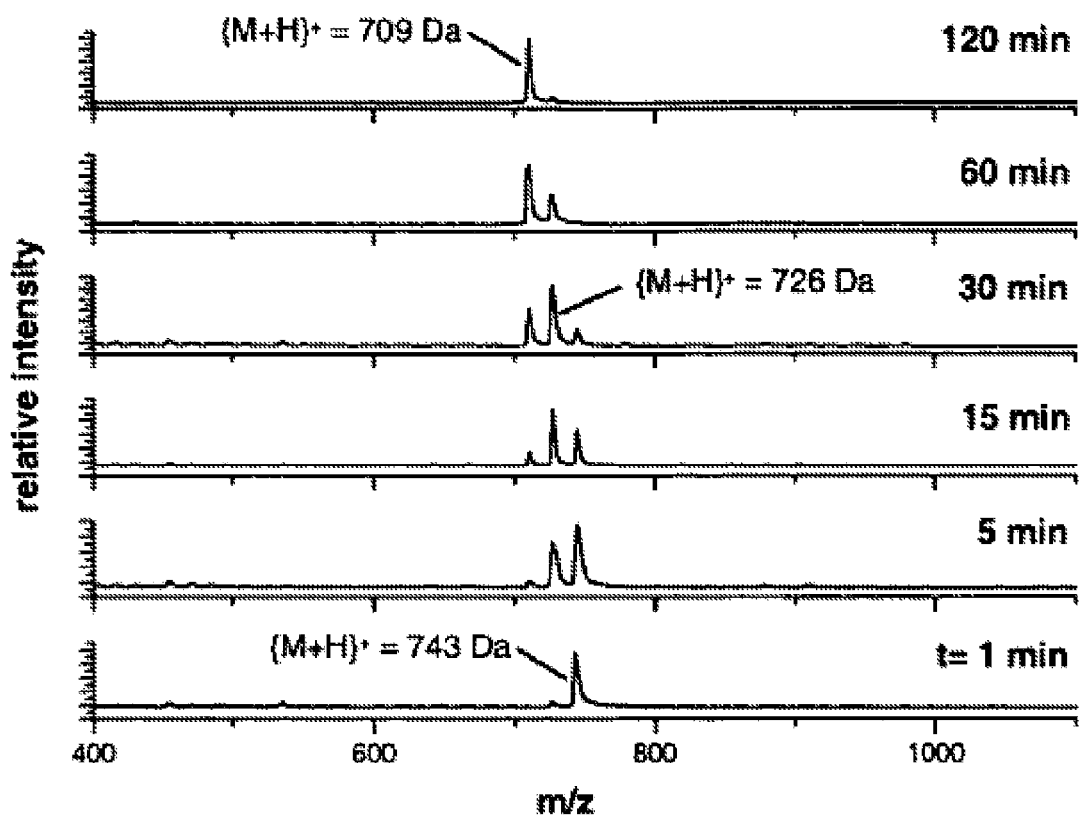
FIG. 5 shows the formation of pGlu-Lys(pGlu)-Arg-Leu-Ala-NH$^2$ from H-Gln-Lys(Gln)-Arg-Leu-Ala-NH$^2$, catalyzed by human QC. Substrate conversion is monitored by a time-dependent change in the m/z ratio due to the expulsion of ammonia. The sample composition was 0.5 mM substrate, 38 nM QC in 40 mM Tris/HCI, pH 7.7. At the times indicated, samples were removed from the assay tube, mixed with matrix solution (1:1 v/v) and subsequently the mass spectra recorded. A very similar dependence was observed in case of papaya QC.

H-Gln-Lys(Gln)-Arg-Leu-Ala-NH$_2$. This N-terminally branched peptide, comprising two glutaminyl residues at the N-terminus that are bound to a lysyl residue via a peptide- and partial isopeptide bond, was converted by human (FIG. 5) and papaya QC (not shown) in an apparently identical manner. Both glutaminyl residues were converted into pyroglutamic acid, without any detectable preference for a distinct residue, as indicated by the consistent substrate conversion (FIG. 5). Thus, the selectivity of the QCs for the differently bound glutaminyl residues differs not fundamentally.

Figure 6:
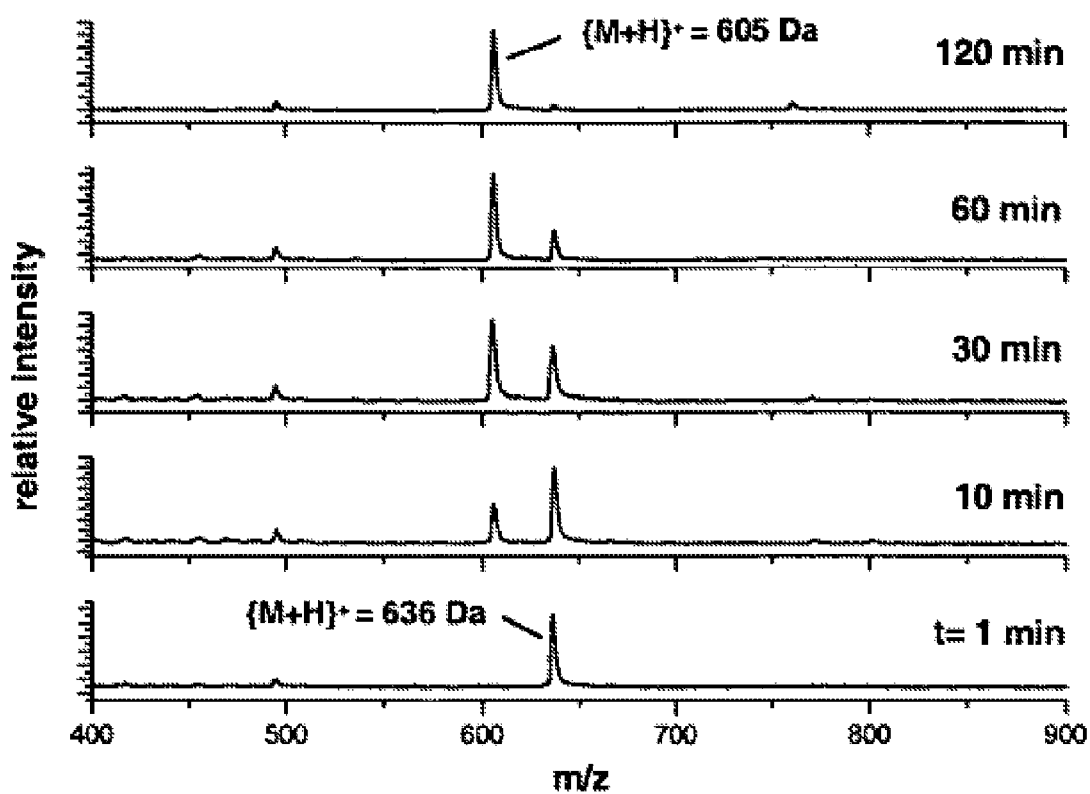
FIG. 6 shows the formation of pGlu-Phe-Lys-Ala-Glu-NH$^2$ (SEQ ID NO: 1) from H-Gln(NMe)-Phe-Lys-Ala-Glu-NH$^2$ (SEQ ID NO: 2) catalyzed by papaya QC. Substrate conversion is monitored by a time-dependent in the m/z ratio due to the expulsion of methylamine. The sample composition was 0.5 mM substrate, 0.65 µM papaya QC in 40 mM Tris/HCI, pH 7.7. At the times indicated, samples were removed from the assay tube, mixed with matrix solution (1:1 v/v) and subsequently the mass spectra recorded. No substrate conversion was observed in samples without papaya QC or by applying up to 1.5 µM human QC to the substrate (not shown).

H-Gln(NMe)-Phe-Lys-Ala-Glu-NH$_2$. (SEQ ID NO: 2) The methylated glutaminyl residue was only converted into a pyroglutamyl residue by papaya QC (FIG. 6). Additionally, an inhibition of the human QC by the peptide was not detected, indicating that the methylated residue is not recognized by human QC.

H-Glu(OMe)-βNA and H-Glu-βNA. Neither of these compounds were converted by papaya or human QC. These fluorogenic substrates were analyzed fluorometrically, utilizing pyroglutamyl aminopeptidase as auxiliary enzyme. The O-methylated glutamate residue, however, showed a remarkable instability in both, Tris and Tricine buffers tending to a non-enzymatically catalyzed cyclization. Furthermore, activity of both QCs against H-Gln-AMC as substrate was not inhibited by the longer peptides H-Glu(OMe)-Phe-Lys-Arg-Leu-Ala-NH$_2$ (SEQ ID NO: 29) or H-Glu-Phe-Lys-Arg-Leu-Ala-NH$_2$ (SEQ ID NO: 30), indicating that glutamic acid or derivates are not recognized by both QC forms. Furthermore, the result implies that not only the negative charge of the glutamic acid residue is the reason for the repulsion of the peptide from the active site.

H-Gln-cyclo(Nε-Lys-Arg-Pro-Ala-Gly-Phe) (SEQ ID NO: 51). The conversion of H-Gln-cyclo(Nε-Lys-Arg-Pro-Ala-Gly-Phe) (SEQ ID NO: 51), which contains an intramolecular partial isopeptide bond was analyzed quantitatively, revealing K$_M$-values of 240±14 µM and 133±5 µM for human and papaya QC, respectively. Due to the higher turnover number of conversion by papaya QC (49.4±0.6 s$^{-1}$) compared to human QC (22.8±0.6 s$^{-1}$), the plant enzyme exhibits with 372±9 mM$^{-1}$ min$^{-1}$ an approximately 4-fold higher k$_{cat}$/K$_M$-value than the human QC. Thus, the specificity constant is in case of the papaya QC only slightly smaller compared to substrates having a similar size, such as H-Gln-Ala-Ala-Ser-Ala-Ala-NH$_2$ (SEQ ID NO: 28). The k$_{cat}$/K$_M$-value for human QC, however, was found with 95±3 mM$^{-1}$ s$^{-1}$ to be approximately one order of magnitude smaller in comparison with substrates of similar size (Table 5).

H-βhomoGln-Phe-Lys-Arg-Leu-Ala-NH$_2$ (SEQ ID NO: 29). The N-terminal β-homoglutaminyl residue was converted into a five-membered lactam ring by catalysis of human and papaya QC, respectively. The concomitant liberation of ammonia was analyzed spectrophotometrically and by MALDI-tof analysis as described before. There was no liberation of ammonia detected when QC was omitted or boiled, indicating a specific catalysis of the cyclization. Interestingly, the QC from C. papaya (K$_M$=3.1±0.3 mM, k$_{cat}$=4.0±0.4 s$^{-1}$) and human (K$_M$=2.5±0.2 mM, k$_{cat}$=3.5±0.1 s$^{-1}$) catalyze the conversion of this peptide with almost identical k$_{cat}$/K$_M$ values of 1.4±0.1 and 1.3±0.1 mM$^{-1}$s$^{-1}$, respectively. Thus, the cyclization of the β-homoglutamine residue is catalyzed with an approximately 1000-fold reduced efficiency compared to peptides of similar size containing a glutaminyl residue at their N-terminus. This shows that the constitution of the α-carbon of the substrate is important for substrate recognition by the QC forms, but not essential. The essential requirement for being a substrate is a γ-amide group and an unprotonated N-terminal amino group in distance and angle prone for cyclization, a requirement that is fulfilled by N-terminal glutaminyl and βhomo-glutaminyl residues.

Example 6

Synthesis of the QC Substrates

Oligopeptides.

Peptides were synthesized semiautomatically in 0.5 mmol scale using a peptide synthesizer (Labortec SP650, Bachem, Switzerland) as previously described (Schilling, S. et al. 2002 Biochemistry 41, 10849-10857). Longer peptides were synthesized in 25 µmol scale using the automated Symphony peptide synthesizer (Rainin Instrument Co.) as described (Manhart, S. et al. 2003 Biochemistry 42, 3081-3088). For all peptide couplings modified Fmoc-protocols of solid-phase peptide synthesis were employed using 2-(1H-Benzotriazole-1-yl)-1,1,3,3,-tetramethyluronium tetrafluoroborate (TBTU; Novabiochem)/base (diisopropyl ethylamine or N-methyl-morpholine; Merck) or in case of difficult couplings N-[(Dimethylamino)-1H-1,2,3,-triazolo[4,5-b]pyridin-1-ylmethylene]-N-methylmethanamminium hexafluorophosphate N-oxide (4,5) (HATU; Applied Biosystems)/diisopropyl ethylamine as activating reagents were used. After cleavage from the resin by trifluoroacetic acid (TFA; Merck) containing cocktail, the crude peptides were purified by preparative HPLC with acid free solvents in order to avoid further cyclization of the N-terminal glutamine. Preparative HPLC was performed with a linear gradient of acetonitrile (Merck) in water (5-40% or 65% acetonitrile over 40 min) on a 250-21 Luna RP18 column (Phenomenex). To confirm peptide purity and identity analytical HPLC and ESI-MS was employed.

Glu(NH—NH$_2$)-Ser-Pro-Thr-Ala-NH$_2$(SEQ ID NO: 32). The linear precursor peptide (Fmoc-Glu-Ser-Pro-Thr-Ala-NH$_2$) (SEQ ID NO: 33) was synthesized according to standard Fmoc-procedures (Schilling, S. et al. 2002 Biochemistry 41, 10849-10857) on Rink amide MBHA resin (Novabiochem). After cleavage of the Fmoc-protected peptide from the resin, the peptide was precipitated with diethyl ether (Merck), filtered and dried. HMBA-AM resin (1.16 mmol/g, Novabiochem) was used for coupling of the γ-carboxylic acid group of glutamic acid of the precursor peptide (3 eq.) in dichloromethane (DCM, Merck). Dicyclohexylcarbodiimide (DCC, Serva) (4 eq.) and dimethylaminopyridine (DMAP, Aldrich) (0.1 eq) were used as coupling reagents. After 12 hours the resin was filtered, washed with DCM and the reaction was repeated. After deprotection of the N-terminal Fmoc-group by employing 20% piperidine in DMF (3×5 min) the peptide resin was treated with a 5% hydrazine solution (20 ml/g) for 1.5 hours. The resin was filtered and washed with dimethylformamide (DMF, Roth, Germany) and TFA. Following evaporation, the crude peptide was precipitated with ether giving 76% yield.

H-Gln-Lys(Gln)-Arg-Leu-Ala-NH$_2$. The linear peptide was synthesized according to standard Fmoc/tBu-procedure on Rink amide MBHA (Schilling, S. et al. 2002 Biochemistry 41, 10849-10857) using Fmoc-Lys(Fmoc)-OH as penultimate amino acid coupling. After deprotection of the two amino protecting groups of lysine with 20% piperidine (Merck) in DMF, 4 eq. Fmoc-Gln(Trt)-OH were coupled. Standard cleavage procedure resulted in 95% yield.

H-Gln(NMe)-Phe-Lys-Ala-Glu-NH$_2$. (SEQ ID NO: 2) Fmoc-Gln(NMe)—OH was synthesized starting from Fmoc-Glu-OtBu loaded on Fmoc-MI-AM (Novabiochem) resin. After swelling with DCM, the resin (0.5 g) was washed with DMF and deprotected with 20% piperidine solution in DMF. The resin was given into 5 ml DMF and 5 eq. Fmoc-Glu-OtBu, 5 eq. HATU and 10 eq. DIPEA were added subsequently and shaken for 6 hours. After filtration and washing, the product was cleaved according to standard TFA cleavage conditions. The peptide H-Gln(NMe)-Phe-Lys-Ala-Glu-NH$_2$ (SEQ ID NO: 2) was synthesized as described (Schilling, S. et al. 2002 Biochemistry 41, 10849-10857). Fmoc-Gln (NMe)—OH was coupled with HATU/DIPEA overnight. Standard cleavage procedure resulted in 78% of the crude peptide.

H-Glu(OMe)-β-naphthylamide, H-Gln-Val-OH, H-Gln-Tyr-OH. Boc-protected dipeptides were synthesized applying standard mixed anhydride procedure by using isobutyl chlorocarbonate (Merck). The C-terminal methylesters Boc-Gln-Tyr-OMe and Boc-Gln-Val-OMe were saponified by 1N NaOH in dioxane. The Boc-protected peptides were deprotected by HCl/dioxane solution for 10 min. After evaporation the residue was crystallized with several solvents giving 60-70% of a solid compound.

H-Gln-cyclo(Nε-Lys-Arg-Pro-Ala-Gly-Phe) (SEQ ID NO: 51). The linear precursor Boc-Gln(Trt)-Lys-Arg(Pmc)-Ala-Gly-Phe-OH (SEQ ID NO: 34) was synthesized on acid sensitive 2-chlorotrityl resin. Coupling was carried out using a standard protocol of Fmoc/tBu-strategy using Fmoc-Lys (Mtt)-OH. After cleavage with 3% TFA solution in DCM (10 times 5 min), the solution was neutralized with 10% pyridine (Merck) in methanol (MeOH; Merck), washed 3 times with DCM and MeOH, evaporated to 5% of the volume and the crude peptide was precipitated with ice cold water. Following, the crude peptide was cyclized using DCC/1-hydroxybenzotriazole (HOBt; Aldrich) activation. The crude peptide was dissolved in dry dichloromethane (0.2 mmol/50 ml), 0.2 mmol N-methylmorpholine and 0.4 mmol 1-hydroxybenzotriazole were added. This solution was added dropwise to a solution of 0.4 mmol dicyclohexylcarbodiimide in 250 ml dichloromethane at 0° C. The reaction was completed by stirring overnight at room temperature. After filtration of N,N'-dicyclohexylurea, the solvent was removed by evaporation. The residue was dissolved in ethyl acetate and washed several times with 1N HCl, saturated solution of $NaHCO_3$ and water. The solution was dried over anhydrous $Na_2SO_4$, filtered and evaporated to dryness in vacuo.

Example 7

Characterization of Effectors of QC

Imidazole Derivatives

Imidazole and benzimidazole derivatives carrying substituents in different positions of the 5-membered ring were tested as inhibitors of QC (Table 3). The constitution of the numbers refers to the imidazole ring. The applied methods are described in example 2.

C-4(5) and C-4,5 Derivatives.

The compounds carrying substitutions in either in the constitutionally equivalent 4- or 5-position of the imidazole ring or in both positions showed a diminished potency for inhibition of human QC. The only exception, however, comprised N-ω-acetylated histamine that proved to be one of the most potent inhibitory compounds. Small substituents in these positions had only little effect on binding as indicated by the similar inhibition constant of 5-hydroxymethyl-4-methylimidazole compared to imidazole. Larger and more bulky groups attached to these sites diminished or abolished binding of the compound by the enzyme. Some of the other substituents tested are known to exert negative inductive or mesomeric effects that are capable to reduce the electron density in the imidazole ring, which also contributes to poorer binding constants. The difference in the $K_i$ values of L-histidine and histidinamide also indicate some influence of the charge on binding. Evidence for electrostatic repulsion of charged substrates were already shown in the substrate specificity studies, i.e. glutaminamide was readily converted to products by human QC, but no reactivity was observed for free glutamine as substrate.

C-2 Derivatives.

All derivatives tested inhibited QC more weakly as imidazole. Any substitution bigger than a proton hinders proper QC-binding. Only due to the methyl group in 2-methyl-benzimidazole, the inhibition constant drops about one order of magnitude. A very similar relation was shown by comparison of the Ki-values for benzimidazole and 2-amino-benzimidazole. Additionally, the results indicate that the influence is not related to electronic alterations.

N-1 Derivatives.

Among the imidazole derivatives tested on inhibition of human QC, most compounds that had improved Ki-values compared to imidazole showed alterations at one nitrogen atom. These compounds also contained one of the most effective QC inhibitors, 1-benzylimidazole. Interestingly, only little alterations of this structure led to a loss of inhibitory quality, as can be seen for 1-benzoylimidazole and phenylimidazole, which was inactive under the experimental conditions. Also in this case, the observed changes seemed not to be only caused by a reduced electron density of the imidazole ring due to the negative mesomeric effect of the Phenyl group, because also the bulky trimethyl-silyl group, exhibiting a positive inductive effect showed reduced binding compared to other residues. Interestingly, one of the less effective compounds of this group was 1-aminopropyl-imidazole. The small efficacy of this compound is caused by the basic amino group, since the sterically similar compounds 1-methylimidazole and 1-vinylimidazole showed improved binding to the active site. Thus, the positively charged amino group accounts for the smaller Ki-value, a result that is corroborated by a comparison of the Ki-values of N-ω-acetylated histamine (Table 3) and histamin (Table 4).

Effect of 3,4 and 3,5 Derivatization.

The imidazole derivatives that contained substituents in positions 4(5) or both were shown to have a restricted efficiency for binding to the enzyme. The effect of the specific substitutions were specified by comparison of the inhibitory constants of L-histamine and the two intermediates in the biological degradation of histamine, 3-methyl-4-histamine and 3-methyl-5-histamine (Table 4). L-Histamine revealed a $K_i$ value that was about one order of magnitude smaller compared to its acetylated counterpart. Methylation of one nitrogen resulted in a considerable improvement of efficacy in case of 3-methyl-4-histamine. Methylation leading to 3-methyl-5-histamine, however, resulted in a complete loss of inhibitory activity. Thus, the observed effect seems to be mainly caused by a sterical hindrance of binding due to the derivatisation of the carbon adjacent to the basic nitrogen. Presumably, the basic nitrogen plays a key role for binding to the enzyme.

Example 8

Formation of A β3-40/42 Derivatives

The measurements were carried out with two short N-terminal peptide sequences of Aβ3-40/42, [Gln³]-Aβ1-11 (sequence: DAQFRHDSGYE) (SEQ ID NO: 35) and [Gln³] Aβ3-11, which contain a glutamine instead of an glutamic acid residue in the third position. Cleavage by DP IV and cyclization of the N-terminal glutamine residue by QC of the two peptides was tested using MALDI-TOF mass spectrometry. Measurements were carried out using purified DP IV (porcine kidney) or crude porcine pituitary homogenate as sources of QC as well as for both enzymes for measurements of consecutive catalysis.

Results

1. Formation of [Gln³]Aβ3-11a from [Gln³]Aβ1-11a Catalysed by DPIV and its Prevention by the DP IV-Inhibitor Val-Pyrrolidide (Val-Pyrr)

Figure 7:
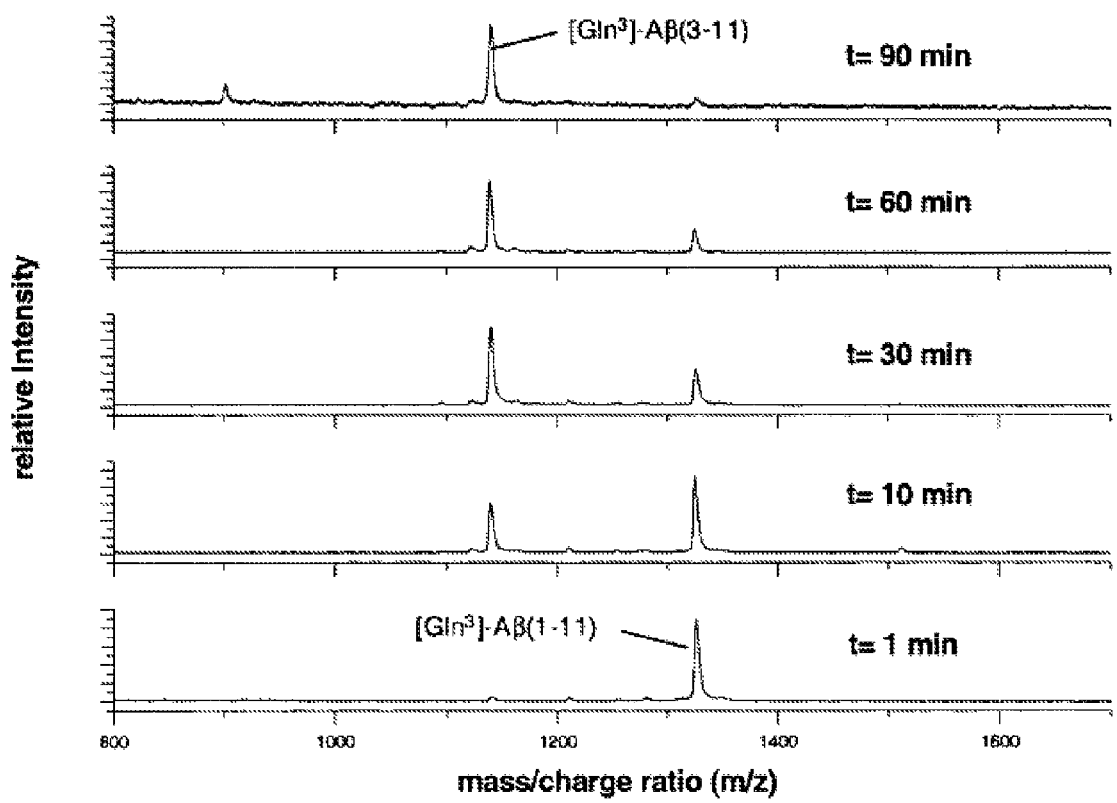
FIG. 7 shows the formation of [Gln$^3$]-Aβ3-11 from [Gln$^3$] Aβ1-11 catalysed by DPIV. At the times indicated, samples were removed, from the assay tube, mixed with matrix solution (1:1 v/v) and subsequently the mass spectra recorded.
Figure 8:
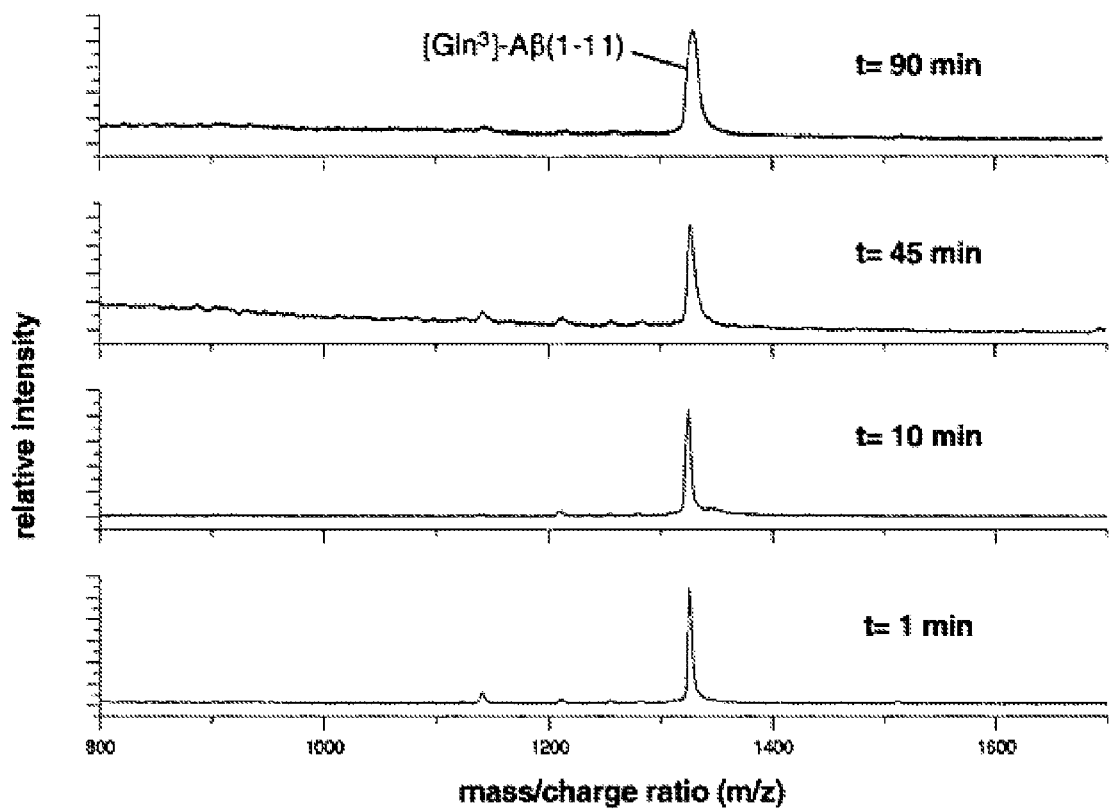
FIG. 8 shows the prevention of the cleavage of [Gln$^3$]Aβ1-11 by the DP IV-inhibitor Val-Pyrrolidide (Val-Pyrr). At the times indicated, samples were removed from the assay tube, mixed with matrix solution (1:1 v/v) and subsequently the mass spectra recorded.

DPIV or DPIV-like activity is cleaving [Gln³]Aβ1-11a under formation of [Gln³]Aβ3-11a (FIG. 7). The residue in the third position is uncovered by this cleavage and becomes therefore accessible for modification by other enzymes, i.e. QC. As expected, catalysis can be completely prevented by Val-Pyrr (FIG. 8).

2. Formation of [pGlu³]Aβ3-11a from [Gln³]Aβ3-11a by Catalysis of QC in Pituitary Homogenate and Prevention by 1,10-Phenanthroline Glutaminyl cyclase present in the homogenate of porcine pituitary catalyzes conversion of [Gln³]Aβ3-11a to [pGlu³]Aβ3-11a (FIG. 9). Formation of [pGlu³]Aβ3-11a was inhibited by addition of 1,10-phenanthroline (FIG. 10).

Figure 11:
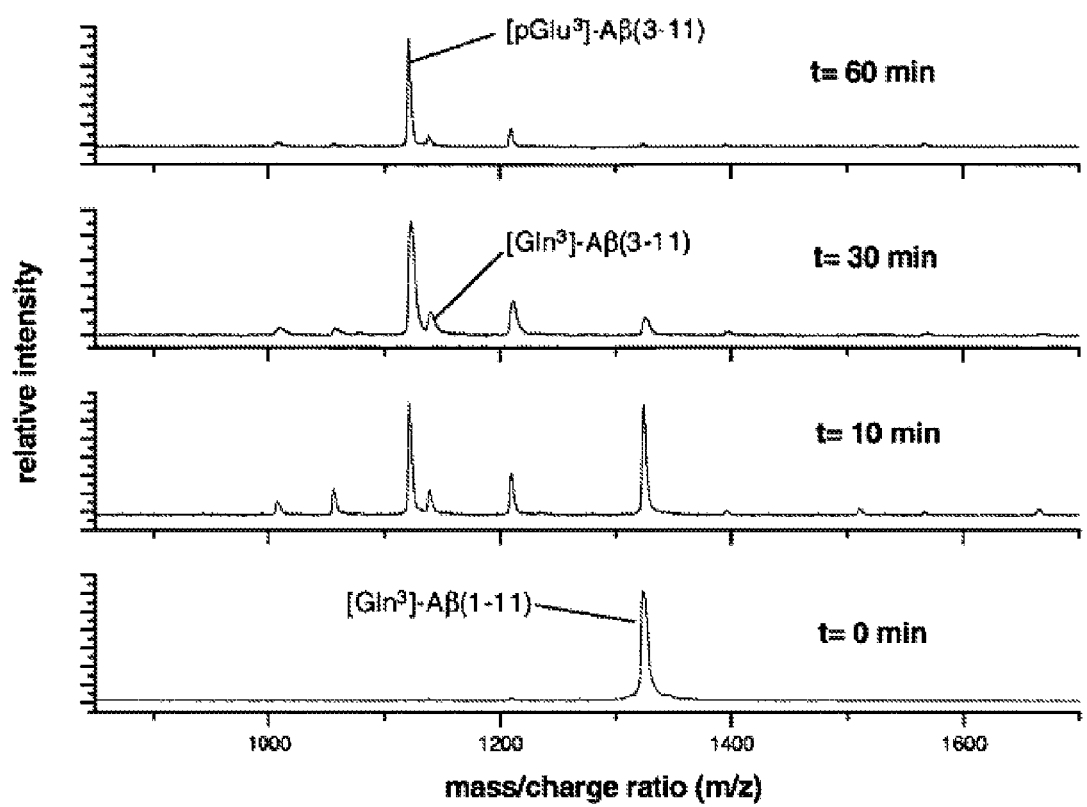
FIG. 11 shows the formation of [pGlu$^3$]Af 3-11 from [Gln$^3$]Aβ1-11 after consecutive catalysis by DP IV and QC. At the times indicated, samples were removed from the assay tube, mixed with matrix solution (1:1 v/v) and subsequently the mass spectra recorded.
Figure 12:
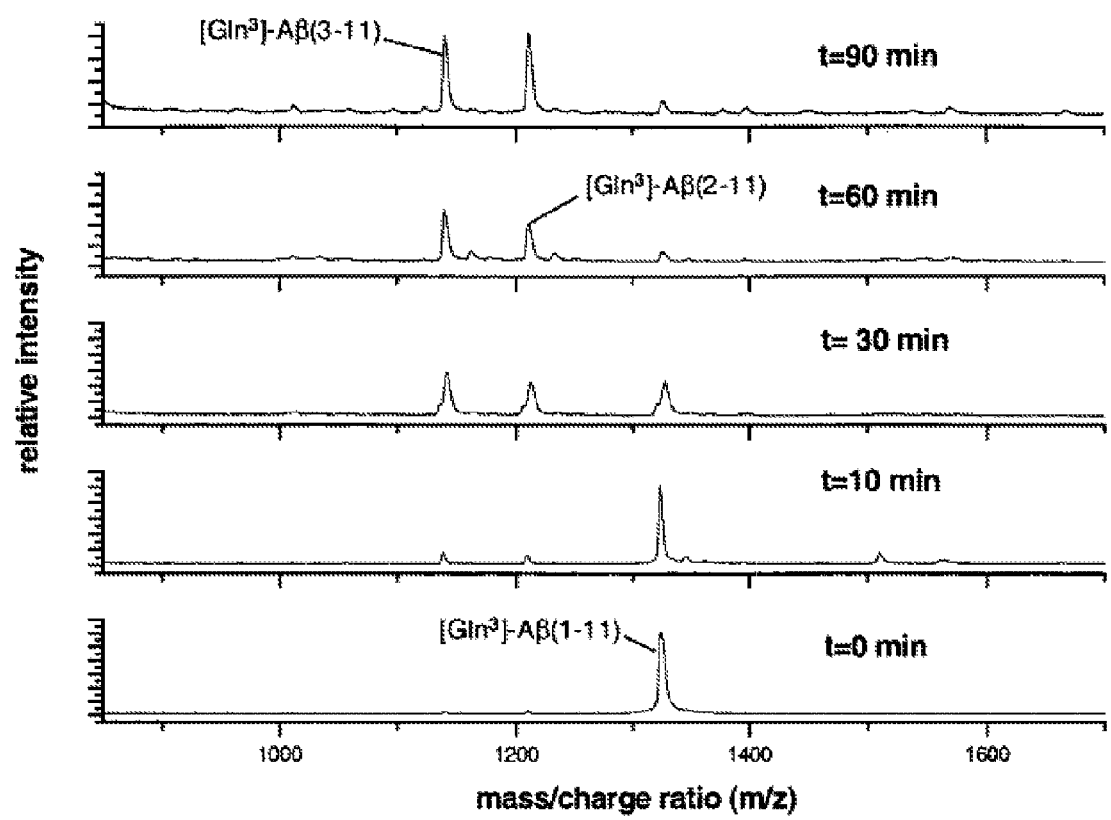
FIG. 12 shows the inhibition of [pGlu$^3$]Aβ3-11 formation from [Gln$^3$]Aβ1-11 by the QC inhibitor 1,10-phenanthroline in the presence of catalytically active DP IV and QC. At the times indicated, samples were removed from the assay tube, mixed with matrix solution (1:1 v/v) and subsequently the mass spectra recorded.
Figure 13:
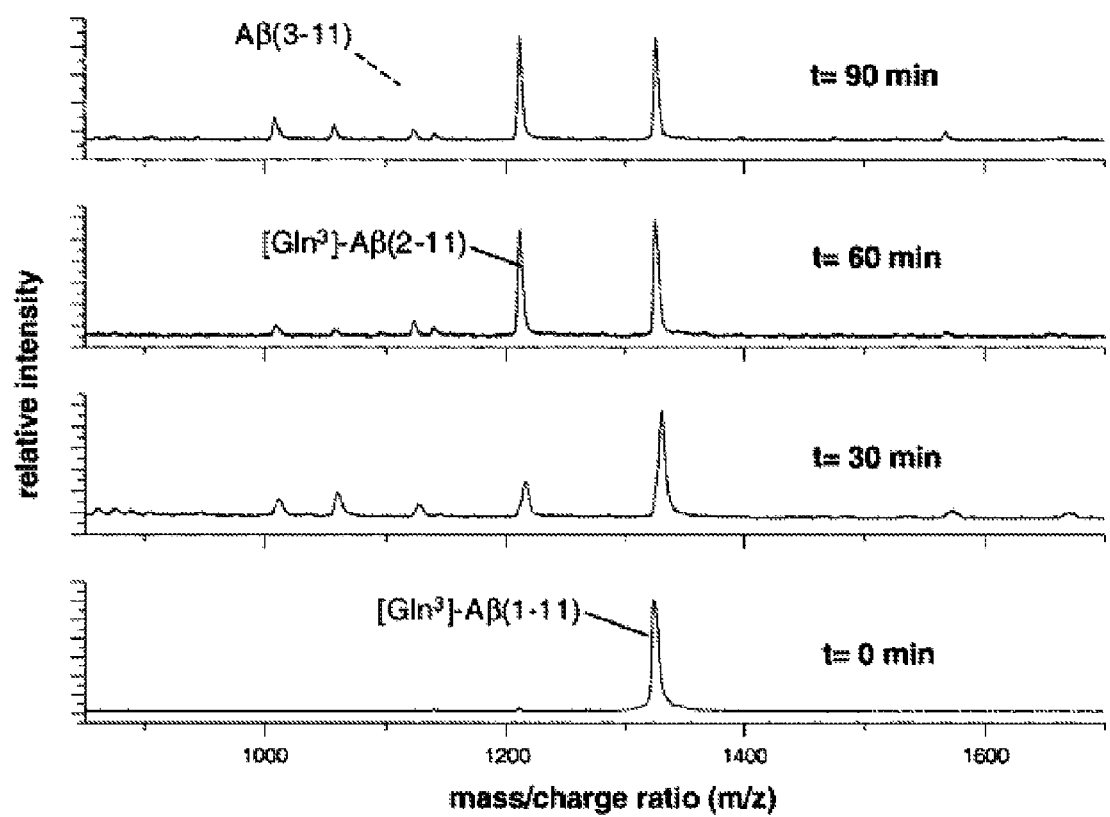
FIG. 13 shows the reduction of [pGlu$^3$]Aβ3-11 formation from [Gln$^3$]Aβ1-11 by the DP IV inhibitor Val-Pyrr in the presence of catalytically active DP IV and QC. At the times indicated, samples were removed from the assay mixture, mixed with matrix solution (1:1 v/v) and subsequently the mass spectra recorded.

3. Consecutive Catalysis of DPIV and QC Resulting in Formation of [pGlu³]Aβ3-11a and Prevention by Val-Pyrr and 1,10-Phenanthroline Formation of [pGlu³]Aβ3-11a from [Gln³]Aβ1-11a takes place after consecutive catalysis by DP IV and QC, measured in crude homogenate of porcine pituitary with added DPIV from porcine kidney (FIG. 11). [pGlu³]Aβ3-11a was not formed when the QC-inhibitor 1,10-phenanthroline (FIG. 12) or the DP IV-inhibitor Val-Pyrr was added (FIG. 13). The slight appearance of [pGlu³]Aβ3-11a is due to aminopeptidase cleavage and following cyclization of the glutamine residue, also indicated by formation of [Gln³]Aβ2-11a.

4. Formation of [pGlu³]Aβ3-11a in Crude Pituitary Homogenate by Catalysis of Aminopeptidase(s)

Figure 14:
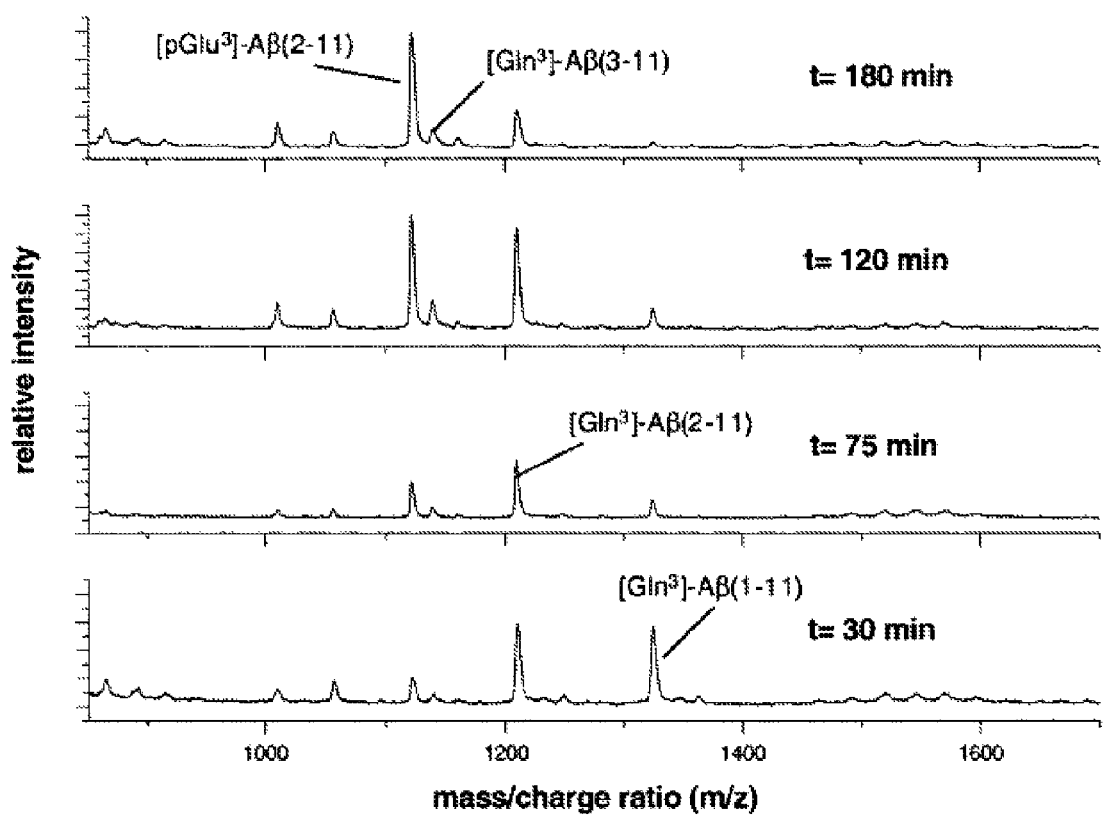
FIG. 14 shows the formation of [pGlu³]Aβ-peptide3-11 from [Gln³]Aβ1-11 after consecutive catalysis by aminopeptidase(s) and QC that are present in porcine pituitary homogenate. At the times indicated, samples were removed from the assay tube, mixed with matrix solution (1:1 v/v) and subsequently the mass spectra recorded.

Due to the formation of [pGlu³]Aβ3-11a that was not dependent on DPIV catalysis, degradation of [Gln³]Aβ1-11a was investigated in crude pituitary homogenate without added DPIV (FIG. 14). As expected from the data in section 4, formation of [pGlu³]Aβ3-11a was observed. The data show that the degradation of [Gln³]Aβ1-11a may also be catalyzed by aminopeptidase(s), resulting in [pGlu³]Aβ3-11a. Hence, the results show that pyroglutamyl formation is an endpoint of N-terminal peptide degradation in this tissue, further supporting the role of QC in plaque formation.

Example 9

Turnover of [Gln³]A☐3-11a; 3-21a and 3-40 by Recombinant Human QC

All [Gln³]Aβ derived peptides tested were efficiently converted by human QC into the corresponding pyroglutamyl forms (Table 8). Due to the poor solubility of [Gln³]Aβ3-21a and [Gln³]Aβ3-40 in aqueous solution, the determinations were carried out in presence of 1% DMSO. The better solubility of [Gln³]Aβ3-11a, however, allowed the kinetic analysis of the QC-catalyzed turnover in presence and absence of DMSO (Table 8). Taken together, the investigation of the Aβ peptides as QC-substrates with chain-length of 8, 18 and 37 amino acids (see Table 8) confirmed the observation that human QC-activity increases with the length of its substrates. Accordingly, Gln1-gastrin, Gln1-neurotensin, Gln1-GnRH are among the best QC-substrates taking the specificity constants into account. Similarly, [Gln³]Aβ3-40 and glucagon, the largest QC-substrates investigated thus far, exhibited high second order rate constants (449 mM⁻¹s⁻¹ and 526 mM⁻¹s⁻¹ respectively) even in presence of 1% DMSO (Table 8).

Interestingly, the kinetic parameters for the conversion of the investigated amyloid peptides did not change dramatically with increasing size, suggesting only moderate effects of the C-terminal part of Aβ on QC catalysis. Therefore, due to better solubility and experimental handling, the further investigations concerning N-terminal aminopeptidase processing of these peptides were performed using the smaller fragments of A[INSERT SYMBOL], [Gln³]Aβ1-11a, [Gln³]Aβ3-11a and Aβ3-11a.

TABLE 8

Kinetic parameters for conversion of N-terminally Gln-containing peptides by recombinant human QC in buffer solution containing 1% DMSO

| Peptide | $K_M$ (μM) | $k_{cat}$ (s⁻¹) | $k_{cat}/K_M$ (mM⁻¹s⁻¹) |
|---|---|---|---|
| [Gln³]Aβ3-11a | 87 ± 3# | 55 ± 1# | 632 ± 10# |
| [Gln³]Aβ3-11a | 155 ± 4 | 41.4 ± 0.4 | 267 ± 4 |
| [Gln³]Aβ3-21a | 162 ± 12 | 62 ± 3 | 383 ± 10 |
| [Gln³]Aβ3-40 | 89 ± 10 | 40 ± 2 | 449 ± 28 |
| Glucagon (3-29) | 19 ± 1 | 10.0 ± 0.2 | 526 ± 17 |

Determined in absence of DMSO

Example 10

Turnover of Aβ3-11a and Aβ3-21a by Recombinant Human QC

Figure 15A:
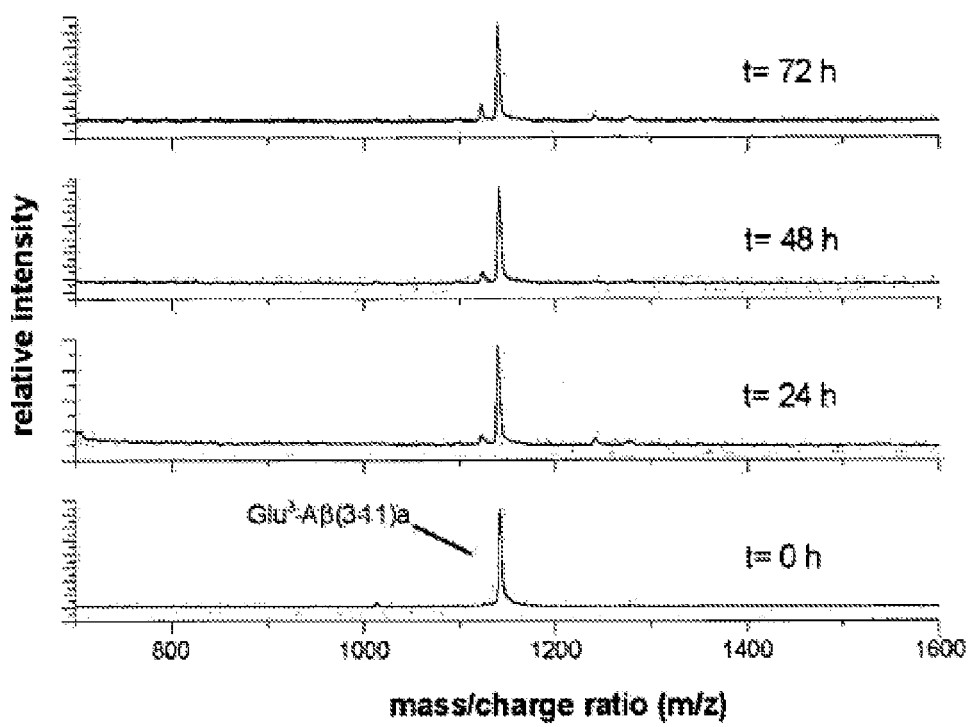
FIGS. 15 A and B show Mass spectra of Aβ3-11a and Aβ3-21a incubated with recombinant human QC, that was boiled for 10 min before use. C and D show Mass spectra of Aβ3-11 and Aβ3-21a in presence of active human QC resulting in the formation of [pGlu³]A(33-11a and [pGlu³]Aβ3-21a, respectively. E and F show Mass spectra of Aβ3-11a and Aβ3-21a in presence of active QC and 5 mM Benzimidazole suppressing the formation of [pGlu3]formation.
Figure 15B:
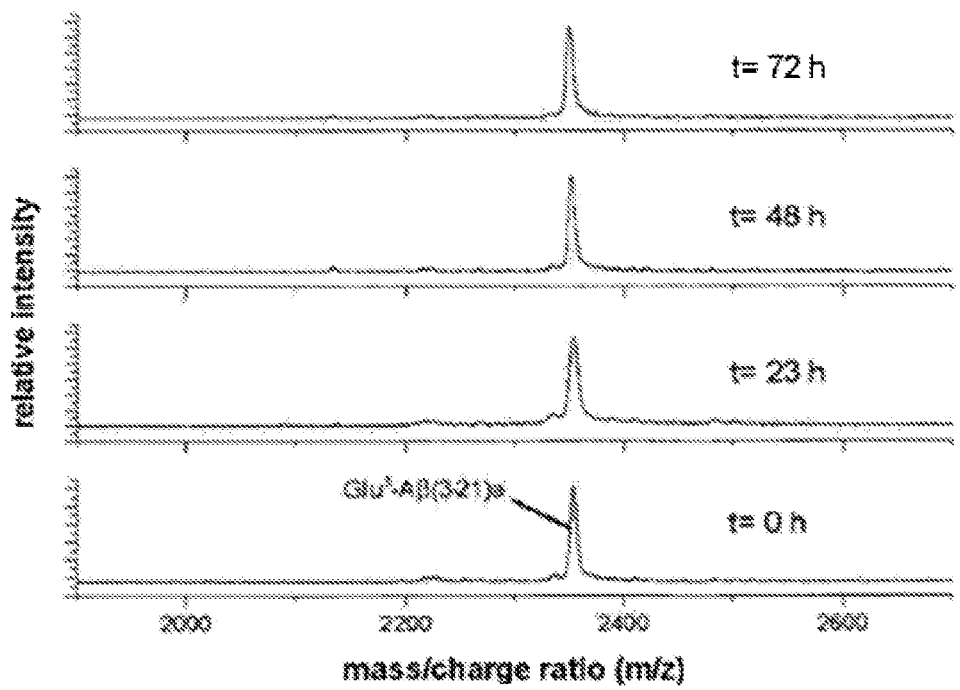
Figure 15C:
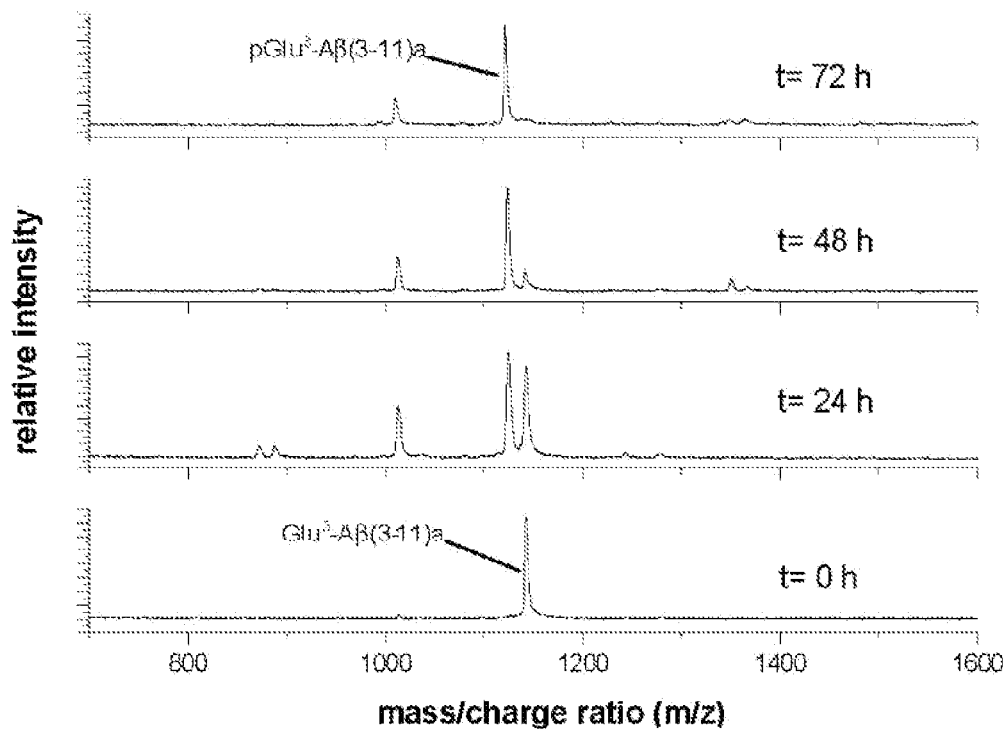
Figure 15D:
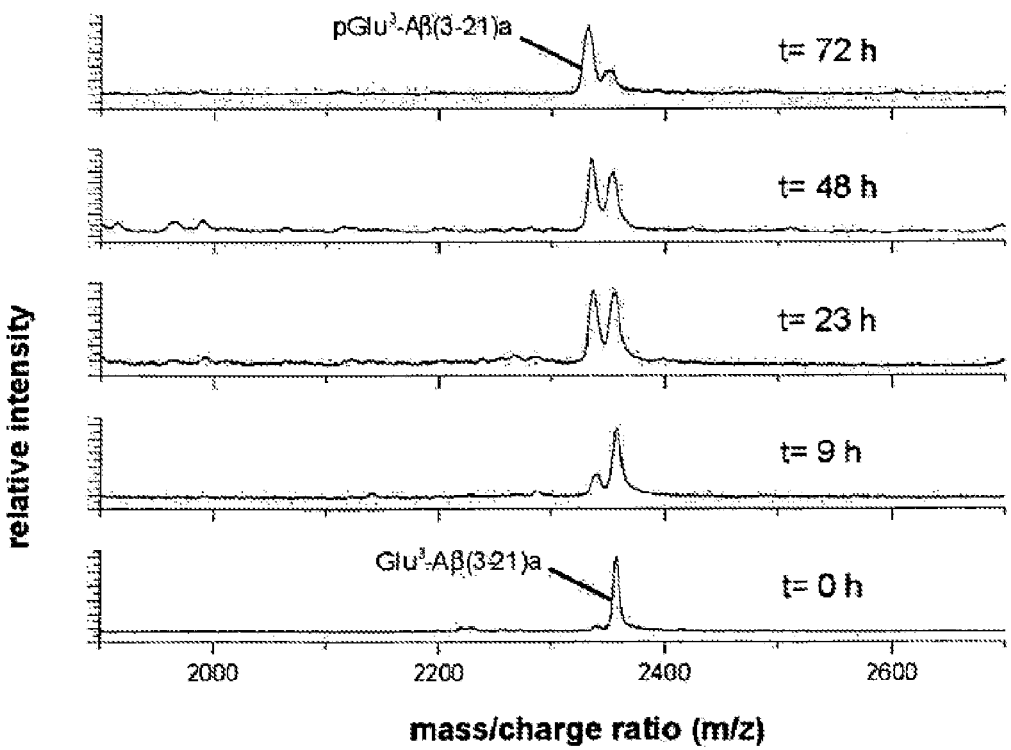
Figure 15E:
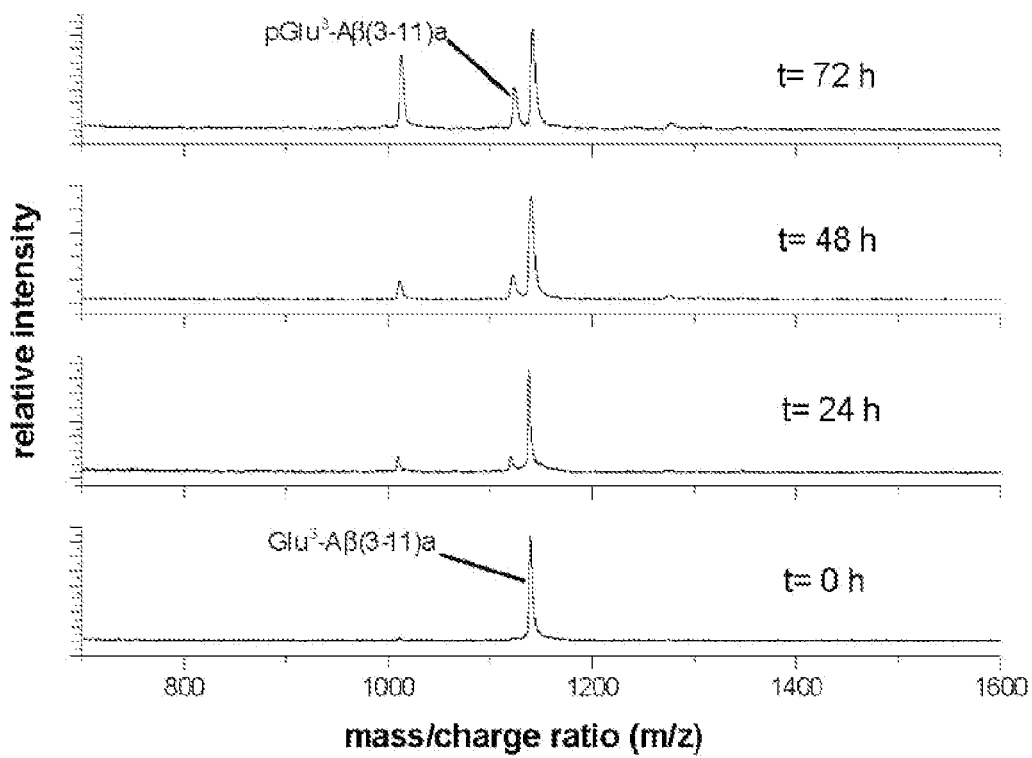
Figure 15F:
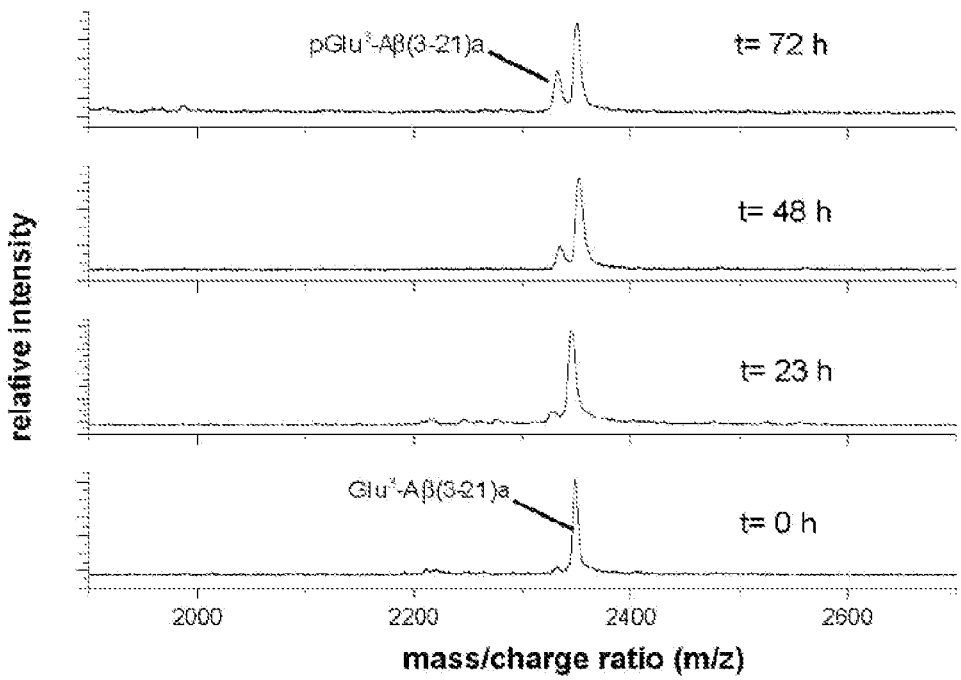

The incubation of Aβ3-11a and Aβ3-21a in presence of QC revealed that in contrast to previous work, glutamate-containing peptides can also serve as QC-substrates (FIGS. 15C and D). The QC-catalyzed formation of [pGlu³]Aβ3-11a and [pGlu³]Aβ3-21a was investigated at pH 5.2 and 6.5, respectively. If the QC-inhibitor benzimidazole was added to the solution before starting the assay by addition of QC, substrate conversion resulting in [pGlu³]Aβ3-11a or [pGlu³]Aβ3-21a was suppressed (FIGS. 15E and F). If QC was boiled before addition, formation of the pGlu-peptides was negligible (FIGS. 15A and B).

Example 11 pH-Dependency of the Papaya QC-Catalyzed Cyclization of Gln-βNA and Glu-βNA

Figure 16:
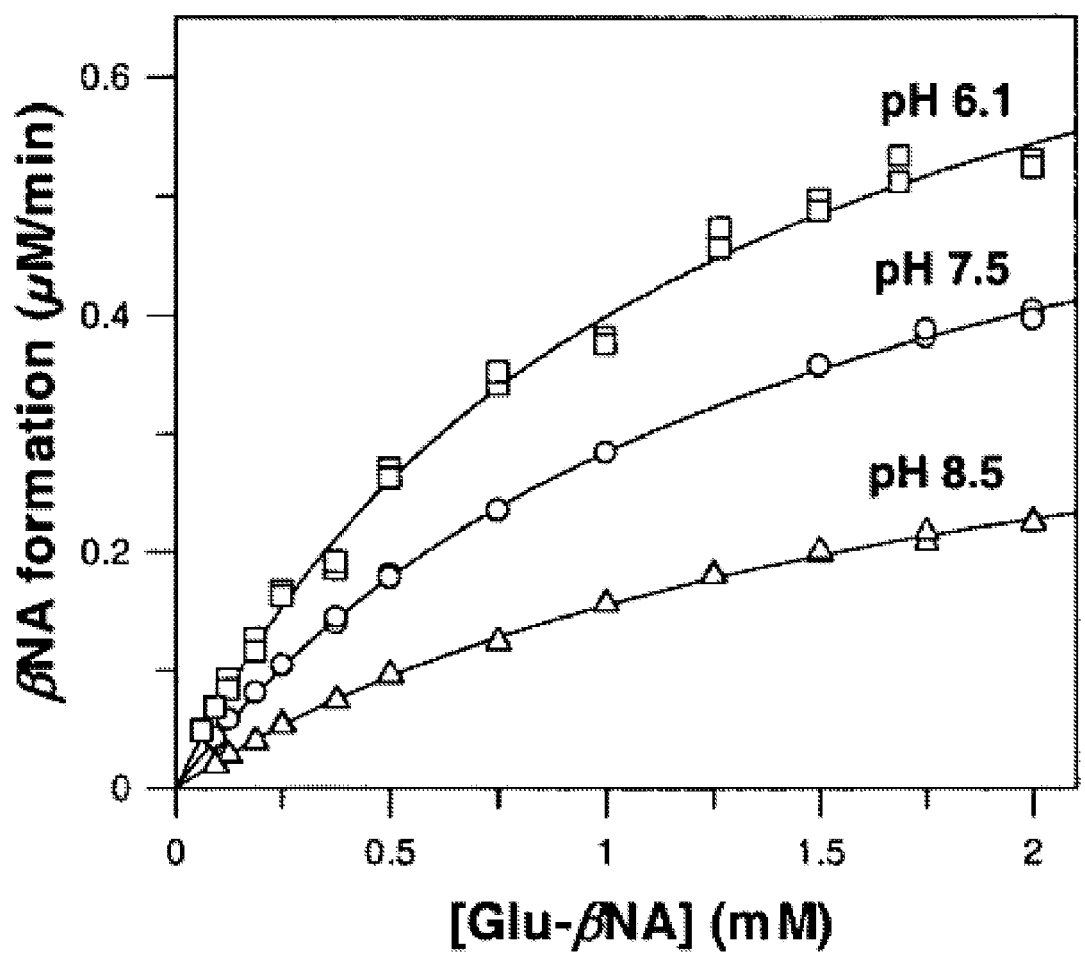
FIG. 16 shows reaction rates of papaya QC-catalyzed Glu-βNA-conversion plotted against the substrate concentration. The initial rates were measured in 0.1 M pyrophosphate buffer, pH 6.1 (squares), 0.1 M phosphate buffer, pH 7.5 (circles) and 0.1 M borate buffer, pH 8.5 (triangles). The kinetic parameters were as follows: $K_M$=1.13±0.07 mM, $k_{cat}$=1.13±0.04 min$^{-1}$ (pH 6.1); $K_M$=1.45±0.03 mM, $k_{cat}$=0.92±0.01 min–1 (pH 7.5); $K_M$=1.76±0.06 mM, $k_{cat}$=0.56±0.01 min$^{-1}$ (pH 8.5).

Papaya QC converted Glu-βNA in a concentration range up to 2 mM (which was limited by substrate solubility) in accordance with Michaelis-Menten kinetics (FIG. 16). Inspection of turnover versus substrate concentration diagrams for the QC-catalyzed conversion of Glu-βNA, studied between pH 6.1 and 8.5, revealed that for this Glu-substrate both parameters, $K_M$ and $k_{cat}$, changed in a pH-dependent manner (FIG. 16). This is in contrast to the previously described QC-catalyzed glutamine cyclization, for which only changes in KM were observed over the given pH range (Gololobov, M. Y., Song, I., Wang, W., and Bateman, R. C. (1994) *Arch Biochem Biophys* 309, 300-307).

Subsequently, to study the impact of the proton concentration during Glu- and Gln-cyclization, the pH-dependence of cyclization of Glu-βNA and Gln-βNA under first-order rate-law conditions (i.e. substrate concentrations far below $K_M$-values) was investigated (FIG. 17). The cyclization of glutamine has a pH-optimum at pH 8.0, in contrast to the cyclization of glutamic acid which showed a pH-optimum of pH 6.0. While the specificity constants at the respective pH-optima differ approximately 80,000-fold, the ratio of QC versus EC activity around pH 6.0, is only about 8,000.

The nonenzymatic pGlu-formation from Gln-βNA investigated at pH 6.0, was followed for 4 weeks and revealed a first-order rate constant of $1.2*10^{-7}$ s⁻¹. However, during the same time period, no pGlu-βNA was formed from Glu-βNA, allowing to estimate a limiting rate constant for turnover of $1.0*10^{-9}$ s⁻¹.

Example 12

Enzyme Inactivation/Reactivation Procedures

An aliquot of human QC (0.1-0.5 mg, 1 mg/ml) was inactivated overnight by dialysis against a 3000-fold excess of 5 mM 1,10-phenanthroline or 5 mM dipicolinic acid in 0.05 M Bis-Tris/HCl, pH 6.8. Subsequently, the inactivating agent was carefully removed by dialysis (3 cycles, 2000-fold excess) of the samples against 0.05 M Bis-Tris/HCl, pH 6.8, containing 1 mM EDTA. Reactivation experiments were performed at room temperature for 15 minutes using $Zn^{++}$, $Mn^{++}$, $Ni^{++}$, $Ca^{++}$, $K^+$ and $Co^{++}$ ions at concentrations of 1.0, 0.5, 0.25 mM in 0.025 M Bis-Tris, pH 6.8 containing 0.5 mM EDTA. QC activity assays were performed in 0.05 M Tris/HCl, pH 8.0, containing 2 mM EDTA, in order to avoid a rapid reactivation by traces of metal ions present in buffer solutions.

Figure 18:
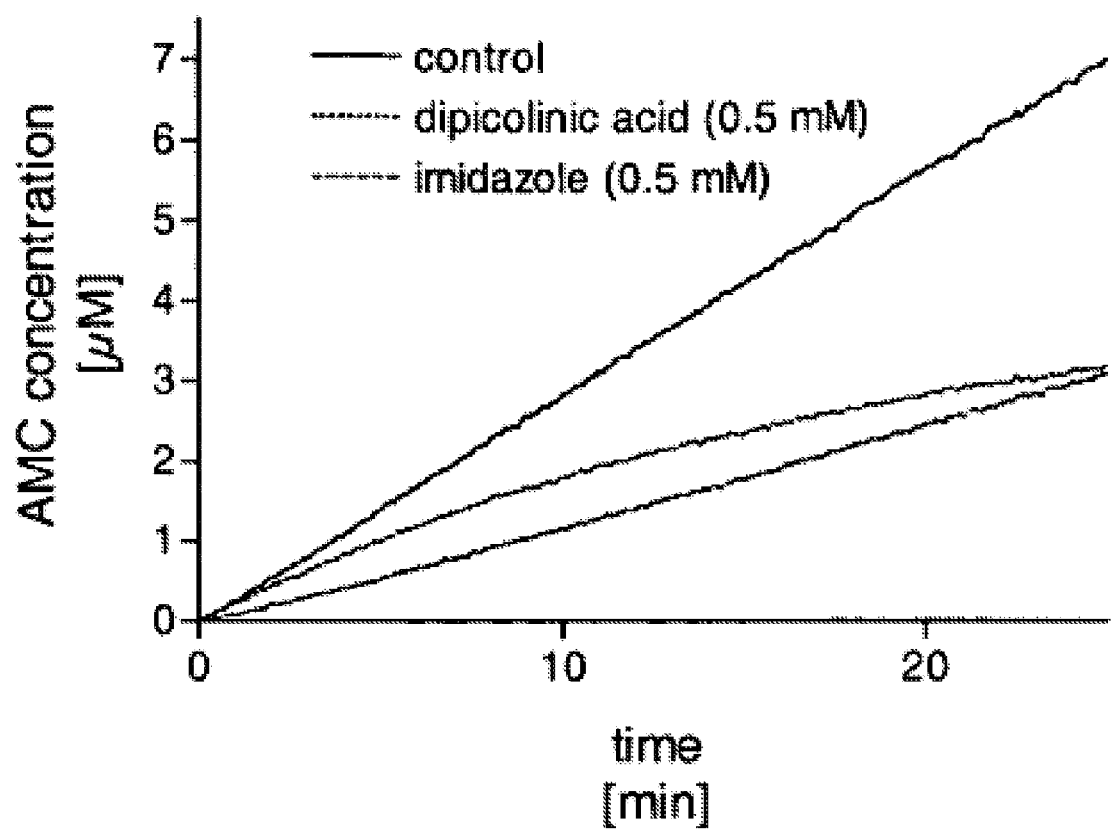
FIG. 18 shows progress curves of human QC-catalyzed cyclization of H-Gln-AMC in presence of imidazole, dipicolinic acid and in absence of an inhibitory compound. The hyperbolic shape of the curve in presence of dipicolinic acid indicates metal ion remove from the active site of QC.

The inhibition of porcine QC by 1,10-phenanthroline has already been described (Busby, W. H. J. et al. 1987 *J Biol Chem* 262, 8532-8536, Bateman, R. C. J. et al. 2001 *Biochemistry* 40). However, the fact that EDTA has been shown to have an activating effect on QC catalysis suggested that inhibition by phenanthroline is not due to metal chelation (Busby, W. H. J. et al. 1987 *J Biol Chem* 262, 8532-8536, Bateman, R. C. J. et al. 2001 *Biochemistry* 40). Also, in addition to being inhibited by 1,10-phenanthroline, human QC catalyzed substrate cyclization was abolished in presence of dipicolinic acid and 8-hydroxyquinoline, other inhibitors of metalloenzymes. These chelators inhibited QC in a competitive and time-dependent manner, i.e., already competitively inhibited initial activity was found to be further reduced after prolonged incubation with the compounds (FIG. 18,19). Interestingly, EDTA did not show remarkable inhibition regardless of incubation time or under any conditions.

Human QC was almost completely inactivated after extensive dialysis against 5 mM 1,10-phenanthroline or 5 mM dipicolinic acid. After repeated dialysis overnight against chelator-free buffer solutions, QC activity was partially reactivated up to 50-60%. However, when dialyzed against buffers containing 1 mM EDTA, no reactivation was observed.

Near-total restoration of QC activity after inactivation by either dipicolinic acid or 1,10-phenanthroline was achieved by incubating the protein for 10 minutes with 0.5 mM ZnSO4 in presence of 0.5 mM EDTA (FIG. 20). Partial restoration of QC activity was similarly obtained using $Co^{++}$ and $Mn^{++}$ ions for reactivation. Even in the presence of 0.25 mM $Zn^{++}$ a reactivation up to 25% of the original activity was possible. No reactivation was observed applying $Ni^{++}$, $Ca^{++}$ or $K^+$ ions. Similarly, incubation of fully active QC with these ions had no effect on the enzyme activity.

---

What is claimed is:

1. A screening method for the identification and selection of inhibitors of glutaminyl cyclase comprising the following steps:
   a) combining at least one candidate compound, a human glutaminyl cyclase, and a substrate of glutaminyl cyclase to form a reaction mixture;
   b) monitoring conversion of the substrate and/or measuring the residual glutaminyl cyclase activity; and
   c) calculating changes in the substrate conversion and/or enzyme activity of glutaminyl cyclase to identify inhibition of glutaminyl cyclase;
   wherein
      said substrate of glutaminyl cyclase comprises an N-terminal glutamate residue, and
      said substrate of glutaminyl cyclase comprises Aβ3-40/42.

2. The screening method according to claim 1, wherein combining at least one candidate compound, glutaminyl cyclase, and a substrate of glutaminyl cyclase to form a reaction mixture comprises contacting the at least one candidate compound with glutaminyl cyclase under conditions which would permit binding there between.

3. The screening method according to claim 2, wherein combining at least one candidate compound, glutaminyl cyclase, and a substrate of glutaminyl cyclase to form a reaction mixture comprises contacting the at least one candidate compound with glutaminyl cyclase under conditions which would permit binding there between; and adding a substrate of glutaminyl cyclase.

4. The screening method according to claim 1, wherein calculating changes in the substrate conversion and/or enzyme activity of glutaminyl cyclase comprises calculating an inhibitor constant (Ki) for the at least one candidate compound.

5. The screening method according to claim 1, further comprising selecting a candidate compound that decreases the conversion of the substrate and/or decreases the activity of glutaminyl cyclase.

6. The screening method according to claim 5, further comprising selecting a candidate compound that inhibits the conversion of an N-terminal glutamic acid residue to a pyroglutamic acid residue of the Aβ3-40/42 substrate of glutaminyl cyclase.

7. The screening method according to claim 5, wherein the selected candidate compound is a competitive inhibitor of glutaminyl cyclase.

8. The method according to claim 7, wherein the selected candidate compound has an inhibitor constant ($K_i$) value of about 0.0071 mM or below.

9. The method according to claim 8, wherein the selected candidate compound has a $K_i$-value in the range of from about 0.00041 mM to about 0.0071 mM.

10. The screening method according to claim 5, wherein the selected candidate compound binds to an active-site bound metal ion of glutaminyl cyclase.

11. The screening method according to claim 1, wherein the at least one candidate compound is a peptide, imidazole derivative, or L-histamine derivative.

12. The screening method according to claim 11, wherein the imidazole derivative is substituted at the N-1 nitrogen atom of the imidazole residue.

13. The screening method according to claim 1, wherein the substrate of glutaminyl cyclase is Aβ3-40/42.

14. The method of claim 1, wherein monitoring the conversion of the substrate comprises fluorometrically monitoring the conversion of the substrate.

15. The method of claim 1, wherein measuring the residual glutaminyl cyclase activity comprises spectrophotmetrically determining glutaminyl cyclase activity.

16. A screening method for the identification and selection of inhibitors of glutaminyl cyclase comprising the following steps:
   a) combining at least one candidate compound, a human glutaminyl cyclase, and a substrate of glutaminyl cyclase to form a reaction mixture;
   b) monitoring conversion of the substrate and/or measuring the residual glutaminyl cyclase activity; and
   c) calculating changes in the substrate conversion and/or enzyme activity of glutaminyl cyclase to identify inhibition of glutaminyl cyclase;
   d) selecting a candidate compound that inhibits the conversion of an N-terminal glutamic acid residue to a pyroglutamic acid residue of the substrate of glutaminyl cyclase,
   wherein
      the substrate of glutaminyl cyclase is Aβ3-40/42, and
      the selected candidate compound is a competitive inhibitor of glutaminyl cyclase with an inhibitor constant (Ki) value in the range of from about 0.00041 mM to about 0.0071 mM.

* * * * *

SEQUENCE LISTING

```
<160> NUMBER OF SEQ ID NOS: 51

<210> SEQ ID NO 1
<211> LENGTH: 5
<212> TYPE: PRT
<213> ORGANISM: Artificial Sequence
<220> FEATURE:
<223> OTHER INFORMATION: Description of Artifical Sequence: Synthetic
      peptide
<220> FEATURE:
<221> NAME/KEY: MOD_RES
<222> LOCATION: (1)..(1)
<223> OTHER INFORMATION: pGlu
<220> FEATURE:
<221> NAME/KEY: MISC_FEATURE
<222> LOCATION: (5)..(5)
<223> OTHER INFORMATION: C-term amidated

<400> SEQUENCE: 1

Glu Phe Lys Ala Glu
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln(NMe)
<220> FEATURE:
<221> NAME/KEY: MISC_FEATURE
<222> LOCATION: (5)..(5)
<223> OTHER INFORMATION: C-term amidated

<400> SEQUENCE: 2

Gln Phe Lys Ala Glu
1               5
```

<210> SEQ ID NO 3
<211> LENGTH: 17
<212> TYPE: PRT
<213> ORGANISM: Homo sapiens
<220> FEATURE:
<221> NAME/KEY: MISC_FEATURE
<222> LOCATION: (17)..(17)
<223> OTHER INFORMATION: C-term amidated

<400> SEQUENCE: 3

```
Gln Gly Pro Trp Leu Glu Glu Glu Glu Ala Tyr Gly Trp Met Asp
1               5                   10                  15

Phe
```

<210> SEQ ID NO 4
<211> LENGTH: 13
<212> TYPE: PRT
<213> ORGANISM: Homo sapiens

<400> SEQUENCE: 4

```
Gln Leu Tyr Glu Asn Lys Pro Arg Arg Pro Tyr Ile Leu
1               5                   10
```

<210> SEQ ID NO 5
<211> LENGTH: 10
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: C-term amidated

<400> SEQUENCE: 5

```
Gln His Trp Ser Tyr Gly Leu Arg Pro Gly
1               5                   10
```

<210> SEQ ID NO 6
<211> LENGTH: 97
<212> TYPE: PRT
<213> ORGANISM: Homo sapiens

<400> SEQUENCE: 6

```
Gln Pro Lys Val Pro Glu Trp Val Asn Thr Pro Ser Thr Cys Cys Leu
1               5                   10                  15

Lys Tyr Tyr Glu Lys Val Leu Pro Arg Arg Leu Val Val Gly Tyr Arg
                20                  25                  30

Lys Ala Leu Asn Cys His Leu Pro Ala Ile Ile Phe Val Thr Lys Arg
                35                  40                  45

Asn Arg Glu Val Cys Thr Asn Pro Asn Asp Asp Trp Val Gln Glu Tyr
            50                  55                  60

Ile Lys Asp Pro Asn Leu Pro Leu Leu Pro Thr Arg Asn Leu Ser Thr
65                  70                  75                  80

Val Lys Ile Ile Thr Ala Lys Asn Gly Gln Pro Gln Leu Leu Asn Ser
                    85                  90                  95

Gln
```

<210> SEQ ID NO 7
<211> LENGTH: 76
<212> TYPE: PRT
<213> ORGANISM: Homo sapiens

<400> SEQUENCE: 7

```
Gln Pro Asp Ser Val Ser Ile Pro Ile Thr Cys Cys Phe Asn Val Ile
```

```
                1               5                   10                  15
Asn Arg Lys Ile Pro Ile Gln Arg Leu Glu Ser Tyr Thr Arg Ile Thr
                20                  25                  30

Asn Ile Gln Cys Pro Lys Glu Ala Val Ile Phe Lys Thr Lys Arg Gly
                35                  40                  45

Lys Glu Val Cys Ala Asp Pro Lys Glu Arg Trp Val Arg Asp Ser Met
    50                  55                  60

Lys His Leu Asp Gln Ile Phe Gln Asn Leu Lys Pro
65                  70                  75
```

<210> SEQ ID NO 8
<211> LENGTH: 76
<212> TYPE: PRT
<213> ORGANISM: Homo sapiens

<400> SEQUENCE: 8

```
Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
                20                  25                  30

Ser Ser Lys Cys Pro Lys Glu Ala Val Ile Phe Lys Thr Ile Val Ala
                35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr
65                  70                  75
```

<210> SEQ ID NO 9
<211> LENGTH: 68
<212> TYPE: PRT
<213> ORGANISM: Homo sapiens

<400> SEQUENCE: 9

```
Gln Val Gly Thr Asn Lys Glu Leu Cys Cys Leu Val Tyr Thr Ser Trp
1               5                   10                  15

Gln Ile Pro Gln Lys Phe Ile Val Asp Tyr Ser Glu Thr Ser Pro Gln
                20                  25                  30

Cys Pro Lys Pro Gly Val Ile Leu Leu Thr Lys Arg Gly Arg Gln Ile
                35                  40                  45

Cys Ala Asp Pro Asn Lys Lys Trp Val Gln Lys Tyr Ile Ser Asp Leu
    50                  55                  60

Lys Leu Asn Ala
65
```

<210> SEQ ID NO 10
<211> LENGTH: 373
<212> TYPE: PRT
<213> ORGANISM: Homo sapiens

<400> SEQUENCE: 10

```
Gln His His Gly Val Thr Lys Cys Asn Ile Thr Cys Ser Lys Met Thr
1               5                   10                  15

Ser Lys Ile Pro Val Ala Leu Leu Ile His Tyr Gln Gln Asn Gln Ala
                20                  25                  30

Ser Cys Gly Lys Arg Ala Ile Ile Leu Glu Thr Arg Gln His Arg Leu
                35                  40                  45

Phe Cys Ala Asp Pro Lys Glu Gln Trp Val Lys Asp Ala Met Gln His
    50                  55                  60
```

Leu Asp Arg Gln Ala Ala Ala Leu Thr Arg Asn Gly Gly Thr Phe Glu
 65                  70                  75                  80

Lys Gln Ile Gly Glu Val Lys Pro Arg Thr Thr Pro Ala Ala Gly Gly
                 85                  90                  95

Met Asp Glu Ser Val Val Leu Glu Pro Glu Ala Thr Gly Glu Ser Ser
            100                 105                 110

Ser Leu Glu Pro Thr Pro Ser Ser Gln Glu Ala Gln Arg Ala Leu Gly
        115                 120                 125

Thr Ser Pro Glu Leu Pro Thr Gly Val Thr Gly Ser Ser Gly Thr Arg
    130                 135                 140

Leu Pro Pro Thr Pro Lys Ala Gln Asp Gly Gly Pro Val Gly Thr Glu
145                 150                 155                 160

Leu Phe Arg Val Pro Pro Val Ser Thr Ala Ala Thr Trp Gln Ser Ser
                165                 170                 175

Ala Pro His Gln Pro Gly Pro Ser Leu Trp Ala Glu Ala Lys Thr Ser
            180                 185                 190

Glu Ala Pro Ser Thr Gln Asp Pro Ser Thr Gln Ala Ser Thr Ala Ser
        195                 200                 205

Ser Pro Ala Pro Glu Glu Asn Ala Pro Ser Gly Gln Arg Val Trp
    210                 215                 220

Gly Gln Gly Gln Ser Pro Arg Pro Glu Asn Ser Leu Glu Arg Glu Glu
225                 230                 235                 240

Met Gly Pro Val Pro Ala His Thr Asp Ala Phe Gln Asp Trp Gly Pro
                245                 250                 255

Gly Ser Met Ala His Val Ser Val Val Pro Val Ser Ser Glu Gly Thr
            260                 265                 270

Pro Ser Arg Glu Pro Val Ala Ser Gly Ser Trp Thr Pro Lys Ala Glu
        275                 280                 285

Glu Pro Ile His Ala Thr Met Asp Pro Gln Arg Leu Gly Val Leu Ile
    290                 295                 300

Thr Pro Val Pro Asp Ala Gln Ala Ala Thr Arg Arg Gln Ala Val Gly
305                 310                 315                 320

Leu Leu Ala Phe Leu Gly Leu Leu Phe Cys Leu Gly Val Ala Met Phe
                325                 330                 335

Thr Tyr Gln Ser Leu Gln Gly Cys Pro Arg Lys Met Ala Gly Glu Met
            340                 345                 350

Ala Glu Gly Leu Arg Tyr Ile Pro Arg Ser Cys Gly Ser Asn Ser Tyr
        355                 360                 365

Val Leu Val Pro Val
    370

<210> SEQ ID NO 11
<211> LENGTH: 76
<212> TYPE: PRT
<213> ORGANISM: Homo sapiens

<400> SEQUENCE: 11

Gln Pro Val Gly Ile Asn Thr Ser Thr Thr Cys Cys Tyr Arg Phe Ile
1               5                   10                  15

Asn Lys Lys Ile Pro Lys Gln Arg Leu Glu Ser Tyr Arg Arg Thr Thr
            20                  25                  30

Ser Ser His Cys Pro Arg Glu Ala Val Ile Phe Lys Thr Lys Leu Asp
        35                  40                  45

Lys Glu Ile Cys Ala Asp Pro Thr Gln Lys Trp Val Gln Asp Phe Met
    50                  55                  60

```
Lys His Leu Asp Lys Lys Thr Gln Thr Pro Lys Leu
 65                  70                  75

<210> SEQ ID NO 12
<211> LENGTH: 33
<212> TYPE: PRT
<213> ORGANISM: Homo sapiens

<400> SEQUENCE: 12

Gln Pro Leu Pro Asp Cys Cys Arg Gln Lys Thr Cys Ser Cys Arg Leu
 1               5                  10                  15

Tyr Glu Leu Leu His Gly Ala Gly Asn His Ala Ala Gly Ile Leu Thr
             20                  25                  30

Leu

<210> SEQ ID NO 13
<211> LENGTH: 11
<212> TYPE: PRT
<213> ORGANISM: Homo sapiens

<400> SEQUENCE: 13

Arg Pro Lys Pro Gln Gln Phe Phe Gly Leu Met
 1               5                  10

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(4)
<223> OTHER INFORMATION: C-term amidated

<400> SEQUENCE: 14

Gln Arg Tyr Phe
 1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(4)
<223> OTHER INFORMATION: C-term amidated

<400> SEQUENCE: 15

Gln Lys Arg Leu
 1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(4)
<223> OTHER INFORMATION: C-term amidated

<400> SEQUENCE: 16
```

Gln Arg Gly Ile
1

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(4)
<223> OTHER INFORMATION: C-term amidated

<400> SEQUENCE: 17

Gln Asn Gly Ile
1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(4)
<223> OTHER INFORMATION: C-term amidated

<400> SEQUENCE: 18

Gln Ser Tyr Phe
1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(4)
<223> OTHER INFORMATION: C-term amidated

<400> SEQUENCE: 19

Gln Pro Tyr Phe
1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(4)
<223> OTHER INFORMATION: C-term amidated

<400> SEQUENCE: 20

Gln His Tyr Phe
1

<210> SEQ ID NO 21
<211> LENGTH: 4
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(4)
<223> OTHER INFORMATION: C-term amidated

<400> SEQUENCE: 21

Gln Gln Tyr Phe
1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(4)
<223> OTHER INFORMATION: C-term amidated

<400> SEQUENCE: 22

Gln Glu Tyr Phe
1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(4)
<223> OTHER INFORMATION: C-term amidated

<400> SEQUENCE: 23

Gln Glu Ala Ala
1

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(4)
<223> OTHER INFORMATION: C-term amidated

<400> SEQUENCE: 24

Gln Glu Tyr Ala
1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(4)
<223> OTHER INFORMATION: C-term amidated
```

```
<400> SEQUENCE: 25

Gln Glu Ala Phe
1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (4)..(4)
<223> OTHER INFORMATION: C-term amidated

<400> SEQUENCE: 26

Gln Glu Asp Leu
1

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (5)..(5)
<223> OTHER INFORMATION: C-term amidated

<400> SEQUENCE: 27

Gln Ala Ala Ala Ala
1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (6)..(6)
<223> OTHER INFORMATION: C-term amidated

<400> SEQUENCE: 28

Gln Ala Ala Ser Ala Ala
1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu(OMe)
<220> FEATURE:
<221> NAME/KEY: MISC_FEATURE
<222> LOCATION: (6)..(6)
<223> OTHER INFORMATION: C-term amidated

<400> SEQUENCE: 29

Glu Phe Lys Arg Leu Ala
```

```
1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (6)..(6)
<223> OTHER INFORMATION: C-term amidated

<400> SEQUENCE: 30

Glu Phe Lys Arg Leu Ala
1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-homoGln
<220> FEATURE:
<221> NAME/KEY: MISC_FEATURE
<222> LOCATION: (6)..(6)
<223> OTHER INFORMATION: C-term amidated

<400> SEQUENCE: 31

Gln Phe Lys Arg Leu Ala
1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu(NH-NH2)
<220> FEATURE:
<221> NAME/KEY: MISC_FEATURE
<222> LOCATION: (5)..(5)
<223> OTHER INFORMATION: C-term amidated

<400> SEQUENCE: 32

Glu Ser Pro Thr Ala
1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (5)..(5)
<223> OTHER INFORMATION: C-term amidated

<400> SEQUENCE: 33

Glu Ser Pro Thr Ala
```

-continued

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln(Trt)
<220> FEATURE:
<221> NAME/KEY: MOD_RES
<222> LOCATION: (3)..(3)
<223> OTHER INFORMATION: Arg(Pmc)

<400> SEQUENCE: 34

Gln Lys Arg Ala Gly Phe
1               5

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asp Ala Gln Phe Arg His Asp Ser Gly Tyr Glu
1               5                   10

<210> SEQ ID NO 36
<211> LENGTH: 361
<212> TYPE: PRT
<213> ORGANISM: Homo sapiens

<400> SEQUENCE: 36

Met Ala Gly Gly Arg His Arg Arg Val Val Gly Thr Leu His Leu Leu
1               5                   10                  15

Leu Leu Val Ala Ala Leu Pro Trp Ala Ser Arg Gly Val Ser Pro Ser
            20                  25                  30

Ala Ser Ala Trp Pro Glu Glu Lys Asn Tyr His Gln Pro Ala Ile Leu
        35                  40                  45

Asn Ser Ser Ala Leu Arg Gln Ile Ala Glu Gly Thr Ser Ile Ser Glu
    50                  55                  60

Met Trp Gln Asn Asp Leu Gln Pro Leu Leu Ile Glu Arg Tyr Pro Gly
65                  70                  75                  80

Ser Pro Gly Ser Tyr Ala Ala Arg Gln His Ile Met Gln Arg Ile Gln
                85                  90                  95

Arg Leu Gln Ala Asp Trp Val Leu Glu Ile Asp Thr Phe Leu Ser Gln
            100                 105                 110

Thr Pro Tyr Gly Tyr Arg Ser Phe Ser Asn Ile Ile Ser Thr Leu Asn
        115                 120                 125

Pro Thr Ala Lys Arg His Leu Val Leu Ala Cys His Tyr Asp Ser Lys
    130                 135                 140

Tyr Phe Ser His Trp Asn Asn Arg Val Phe Val Gly Ala Thr Asp Ser
145                 150                 155                 160

Ala Val Pro Cys Ala Met Met Leu Glu Leu Ala Arg Ala Leu Asp Lys
                165                 170                 175

Lys Leu Leu Ser Leu Lys Thr Val Ser Asp Ser Lys Pro Asp Leu Ser

```
                180                 185                 190
Leu Gln Leu Ile Phe Phe Asp Gly Glu Glu Ala Phe Leu His Trp Ser
        195                 200                 205

Pro Gln Asp Ser Leu Tyr Gly Ser Arg His Leu Ala Ala Lys Met Ala
210                 215                 220

Ser Thr Pro His Pro Pro Gly Ala Arg Gly Thr Ser Gln Leu His Gly
225                 230                 235                 240

Met Asp Leu Leu Val Leu Leu Asp Leu Ile Gly Ala Pro Asn Pro Thr
                245                 250                 255

Phe Pro Asn Phe Phe Pro Asn Ser Ala Arg Trp Phe Glu Arg Leu Gln
        260                 265                 270

Ala Ile Glu His Glu Leu His Glu Leu Gly Leu Leu Lys Asp His Ser
        275                 280                 285

Leu Glu Gly Arg Tyr Phe Gln Asn Tyr Ser Tyr Gly Gly Val Ile Gln
        290                 295                 300

Asp Asp His Ile Pro Phe Leu Arg Arg Gly Val Pro Val Leu His Leu
305                 310                 315                 320

Ile Pro Ser Pro Phe Pro Glu Val Trp His Thr Met Asp Asp Asn Glu
                325                 330                 335

Glu Asn Leu Asp Glu Ser Thr Ile Asp Asn Leu Asn Lys Ile Leu Gln
        340                 345                 350

Val Phe Val Leu Glu Tyr Leu His Leu
        355                 360

<210> SEQ ID NO 37
<211> LENGTH: 284
<212> TYPE: PRT
<213> ORGANISM: Streptomyces griseus

<400> SEQUENCE: 37

Ala Pro Asp Ile Pro Leu Ala Asn Val Lys Ala His Leu Thr Gln Leu
1               5                   10                  15

Ser Thr Ile Ala Ala Asn Asn Gly Gly Asn Arg Ala His Gly Arg Pro
            20                  25                  30

Gly Tyr Lys Ala Ser Val Asp Tyr Val Lys Ala Lys Leu Asp Ala Ala
        35                  40                  45

Gly Tyr Thr Thr Thr Leu Gln Gln Phe Thr Ser Gly Gly Ala Thr Gly
    50                  55                  60

Tyr Asn Leu Ile Ala Asn Trp Pro Gly Gly Asp Pro Asn Lys Val Leu
65                  70                  75                  80

Met Ala Gly Ala His Leu Asp Ser Val Ser Ser Gly Ala Gly Ile Asn
                85                  90                  95

Asp Asn Gly Ser Gly Ser Ala Ala Val Leu Glu Thr Ala Leu Ala Val
            100                 105                 110

Ser Arg Ala Gly Tyr Gln Pro Asp Lys His Leu Arg Phe Ala Trp Trp
        115                 120                 125

Gly Ala Glu Glu Leu Gly Leu Ile Gly Ser Lys Phe Tyr Val Asn Asn
    130                 135                 140

Leu Pro Ser Ala Asp Arg Ser Lys Leu Ala Gly Tyr Leu Asn Phe Asp
145                 150                 155                 160

Met Ile Gly Ser Pro Asn Pro Gly Tyr Phe Val Tyr Asp Asp Asp Pro
                165                 170                 175

Val Ile Glu Lys Thr Phe Lys Asn Tyr Phe Ala Gly Leu Asn Val Pro
            180                 185                 190

Thr Glu Ile Glu Thr Glu Gly Asp Gly Arg Ser Asp His Ala Pro Phe
```

```
                195                 200                 205
Lys Asn Val Gly Val Pro Val Gly Gly Leu Phe Thr Gly Ala Gly Tyr
    210                 215                 220

Thr Lys Ser Ala Ala Gln Ala Gln Lys Trp Gly Gly Thr Ala Gly Gln
225                 230                 235                 240

Ala Phe Asp Arg Cys Tyr His Ser Ser Cys Asp Ser Leu Ser Asn Ile
                245                 250                 255

Asn Asp Thr Ala Leu Asp Arg Asn Ser Asp Ala Ala His Ala Ile
                260                 265                 270

Trp Thr Leu Ser Ser Gly Thr Gly Glu Pro Pro Thr
    275                 280

<210> SEQ ID NO 38
<211> LENGTH: 314
<212> TYPE: PRT
<213> ORGANISM: Homo sapiens

<400> SEQUENCE: 38

Ala Asn Glu Tyr Ala Tyr Arg Arg Gly Ile Ala Glu Ala Val Gly Leu
1               5                   10                  15

Pro Ser Ile Pro Val His Pro Ile Gly Tyr Tyr Asp Ala Gln Lys Leu
                20                  25                  30

Leu Glu Lys Met Gly Gly Ser Ala Pro Pro Asp Ser Ser Trp Arg Gly
            35                  40                  45

Ser Leu Lys Val Pro Tyr Asn Val Gly Pro Gly Phe Thr Gly Asn Phe
    50                  55                  60

Ser Thr Gln Lys Val Lys Met His Ile His Ser Thr Asn Glu Val Thr
65                  70                  75                  80

Arg Ile Tyr Asn Val Ile Gly Thr Leu Arg Gly Ala Val Glu Pro Asp
                85                  90                  95

Arg Tyr Val Ile Leu Gly Gly His Arg Asp Ser Trp Val Phe Gly Gly
                100                 105                 110

Ile Asp Pro Gln Ser Gly Ala Ala Val Val His Glu Ile Val Arg Ser
            115                 120                 125

Phe Gly Thr Leu Lys Lys Glu Gly Trp Arg Pro Arg Arg Thr Ile Leu
130                 135                 140

Phe Ala Ser Trp Asp Ala Glu Glu Phe Gly Leu Leu Gly Ser Thr Glu
145                 150                 155                 160

Trp Ala Glu Glu Asn Ser Arg Leu Leu Gln Glu Arg Gly Val Ala Tyr
                165                 170                 175

Ile Asn Ala Asp Ser Ser Ile Glu Gly Asn Tyr Thr Leu Arg Val Asp
            180                 185                 190

Cys Thr Pro Leu Met Tyr Ser Leu Val His Asn Leu Thr Lys Glu Leu
        195                 200                 205

Lys Ser Pro Asp Glu Gly Phe Glu Gly Lys Ser Leu Tyr Glu Ser Trp
    210                 215                 220

Thr Lys Lys Ser Pro Ser Pro Glu Phe Ser Gly Met Pro Arg Ile Ser
225                 230                 235                 240

Lys Leu Gly Ser Gly Asn Asp Phe Glu Val Phe Phe Gln Arg Leu Gly
                245                 250                 255

Ile Ala Ser Gly Arg Ala Arg Tyr Thr Lys Asn Trp Glu Thr Asn Lys
            260                 265                 270

Phe Ser Gly Tyr Pro Leu Tyr His Ser Val Tyr Glu Thr Tyr Glu Leu
        275                 280                 285

Val Glu Lys Phe Tyr Asp Pro Met Phe Lys Tyr His Leu Thr Val Ala
```

```
            290                 295                 300
Gln Val Arg Gly Gly Met Val Phe Glu Leu
305                 310

<210> SEQ ID NO 39
<211> LENGTH: 42
<212> TYPE: PRT
<213> ORGANISM: Artificial Sequence
<220> FEATURE:
<223> OTHER INFORMATION: A(beta)1-42

<400> SEQUENCE: 39

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 40
<211> LENGTH: 40
<212> TYPE: PRT
<213> ORGANISM: Artificial Sequence
<220> FEATURE:
<223> OTHER INFORMATION: A(beta)1-40

<400> SEQUENCE: 40

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 41
<211> LENGTH: 40
<212> TYPE: PRT
<213> ORGANISM: Artificial Sequence
<220> FEATURE:
<223> OTHER INFORMATION: A(beta)3-42

<400> SEQUENCE: 41

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val Ile Ala
        35                  40

<210> SEQ ID NO 42
<211> LENGTH: 38
<212> TYPE: PRT
<213> ORGANISM: Artificial Sequence
<220> FEATURE:
<223> OTHER INFORMATION: A(beta)3-40

<400> SEQUENCE: 42

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val
        35
```

<210> SEQ ID NO 43
<211> LENGTH: 11
<212> TYPE: PRT
<213> ORGANISM: Artificial Sequence
<220> FEATURE:
<223> OTHER INFORMATION: A(beta)1-11a
<220> FEATURE:
<221> NAME/KEY: MISC_FEATURE
<222> LOCATION: (11)..(11)
<223> OTHER INFORMATION: C-term amidated

<400> SEQUENCE: 43

Asp Ala Glu Phe Arg His Asp Ser Gly Tyr Glu
1               5                   10

<210> SEQ ID NO 44
<211> LENGTH: 9
<212> TYPE: PRT
<213> ORGANISM: Artificial Sequence
<220> FEATURE:
<223> OTHER INFORMATION: A(beta)3-11a
<220> FEATURE:
<221> NAME/KEY: MISC_FEATURE
<222> LOCATION: (9)..(9)
<223> OTHER INFORMATION: C-term amidated

<400> SEQUENCE: 44

Glu Phe Arg His Asp Ser Gly Tyr Glu
1               5

<210> SEQ ID NO 45
<211> LENGTH: 21
<212> TYPE: PRT
<213> ORGANISM: Artificial Sequence
<220> FEATURE:
<223> OTHER INFORMATION: A(beta)1-21a
<220> FEATURE:
<221> NAME/KEY: MISC_FEATURE
<222> LOCATION: (21)..(21)
<223> OTHER INFORMATION: C-term amidated

<400> SEQUENCE: 45

Asp Ala Glu Phe Arg His Asp Ser Gly Tyr Glu Val His His Gln Lys
1               5                   10                  15

Leu Val Phe Phe Ala
            20

<210> SEQ ID NO 46
<211> LENGTH: 19
<212> TYPE: PRT
<213> ORGANISM: Artificial Sequence
<220> FEATURE:
<223> OTHER INFORMATION: A(beta)3-21a
<220> FEATURE:
<221> NAME/KEY: MISC_FEATURE
<222> LOCATION: (19)..(19)
<223> OTHER INFORMATION: C-term amidated

<400> SEQUENCE: 46

Glu Phe Arg His Asp Ser Gly Tyr Glu Val His His Gln Lys Leu Val
1               5                   10                  15

Phe Phe Ala

<210> SEQ ID NO 47
<211> LENGTH: 38
<212> TYPE: PRT
<213> ORGANISM: Artificial Sequence
<220> FEATURE:

```
<223> OTHER INFORMATION: Gln(3)-A(beta)3-40

<400> SEQUENCE: 47

Gln Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val
        35

<210> SEQ ID NO 48
<211> LENGTH: 19
<212> TYPE: PRT
<213> ORGANISM: Artificial Sequence
<220> FEATURE:
<223> OTHER INFORMATION: Gln(3)-A(beta)3-21a
<220> FEATURE:
<221> NAME/KEY: MISC_FEATURE
<222> LOCATION: (19)..(19)
<223> OTHER INFORMATION: C-term amidated

<400> SEQUENCE: 48

Gln Phe Arg His Asp Ser Gly Tyr Glu Val His His Gln Lys Leu Val
1               5                   10                  15

Phe Phe Ala

<210> SEQ ID NO 49
<211> LENGTH: 11
<212> TYPE: PRT
<213> ORGANISM: Artificial Sequence
<220> FEATURE:
<223> OTHER INFORMATION: Gln(3)-A(beta)-1-11a
<220> FEATURE:
<221> NAME/KEY: MISC_FEATURE
<222> LOCATION: (11)..(11)
<223> OTHER INFORMATION: C-term amidated

<400> SEQUENCE: 49

Asp Ala Gln Phe Arg His Asp Ser Gly Tyr Glu
1               5                   10

<210> SEQ ID NO 50
<211> LENGTH: 9
<212> TYPE: PRT
<213> ORGANISM: Artificial Sequence
<220> FEATURE:
<223> OTHER INFORMATION: Gln(3)-A(beta)3-11a
<220> FEATURE:
<221> NAME/KEY: MISC_FEATURE
<222> LOCATION: (9)..(9)
<223> OTHER INFORMATION: C-term amidated

<400> SEQUENCE: 50

Gln Phe Arg His Asp Ser Gly Tyr Glu
1               5

<210> SEQ ID NO 51
<211> LENGTH: 7
<212> TYPE: PRT
<213> ORGANISM: Artificial Sequence
<220> FEATURE:
<223> OTHER INFORMATION: cyclic peptide sequence
<220> FEATURE:
<221> NAME/KEY: MISC_FEATURE
<222> LOCATION: (2)..(7)
<223> OTHER INFORMATION: cyclic peptide
```

```
<400> SEQUENCE: 51

Gln Lys Arg Pro Ala Gly Phe
1               5
```